(12) United States Patent
Wang et al.

(10) Patent No.: US 6,174,874 B1
(45) Date of Patent: *Jan. 16, 2001

(54) PHOSPHONIC ACIDS DERIVATIVES AS INHIBITORS OF PROTEIN TYROSINE PHOSPHATE 1B (PTP-1B)

(75) Inventors: Zhaoyin Wang, Pierrefonds; Claude Dufresne, Dollard-des-Ormeaux; Yves Leblanc, Kirkland; Chun Sing Li, Dollard-des-Ormeaux; Jacques Y. Gauthier, Laval; Cheuk K. Lau, Ile Bizard; Michel Therien, Laval; Patrick Roy, Dollard des Ormeaux, all of (CA)

(73) Assignee: Merck Frosst Canada & Co., Kirkland (CA)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/398,356

(22) Filed: Sep. 17, 1999

Related U.S. Application Data

(60) Provisional application No. 60/101,164, filed on Sep. 21, 1998, and provisional application No. 60/127,420, filed on Apr. 1, 1999.

(51) Int. Cl.[7] .......................... A61K 31/663; C07F 9/38; C07F 9/6518; C07F 9/653; C07F 9/6541
(52) U.S. Cl. ................................ 514/80; 514/86; 514/92; 514/107; 514/120; 514/121; 514/125; 514/129; 544/243; 548/113; 548/119; 560/9; 560/37; 560/55; 560/60; 562/11; 562/20; 562/23; 562/24
(58) Field of Search ............................ 544/243; 548/119; 560/55; 562/20; 514/80, 86, 107, 121

(56) References Cited

FOREIGN PATENT DOCUMENTS

WO97/40017    10/1997   (WO) .
WO 98/20156   5/1998    (WO) .

OTHER PUBLICATIONS

Taylor et al., Bioorg. Med. Chem., 6(9), 1457–1468, 1998.*
Ahmad, et al., J. Biol.Chem. 270: 20503–20508, 1995.
Bin, et al, Tetrahedron, NL, Elsevier Science Publishers, Amsterdam, vol. 52, NO. 30, pp. 9963–9970.
Calan, et al, Bioorganic & Medicinal Chem. Letters, GB, Oxford, vol. 8, No. 5, pp. 515–520.
Charbonneau, et al, Proc. Natl. Acad, Sci. USA 86:5252–5256, 1989.
Fishcer, et al., Science 253:401–406, 1991.
Goldstein, Receptor 3:1–15, 1993.
Kotoris, et al., J. Org. Chem. 63, pp. 8052–8057, 1998.
Kotoris, et al., Bioorg. Med. Chem. vol. 8, pp. 3275–3280, 1998.
Seely, et al., Diabetes 45: 1379–1385, 1996.
Taylor, et al., Bioorg. Med. Chem., vol. 6, p. 2235, 1998.
Taylor, et al., Tetrahedron Letters, vol. 8, No. 45, pp. 8089–8092, 1996.
Taylor, et al., Tetrahedron, No. 54, pp. 1691–1714, 1998.
Wang, et al., Bioorg. Med. Chem., Let. 8(4) 345–350, 1998.
White, et al., J. Biol. Chem. 269: 11–4, 1994.
Yokomatsu, et al., Tetrahedron, NL, Elsevier Science Publishers, Amsterdam, vol. 54, No. 32, pp. 9341–9356.

* cited by examiner

*Primary Examiner*—Fiona T. Powers
(74) *Attorney, Agent, or Firm*—James L. McGinnis; David L. Rose; Richard C. Billups

(57) ABSTRACT

The invention encompasses the novel class of compounds represented by formula I which are inhibitors of the PTP-1B enzyme.

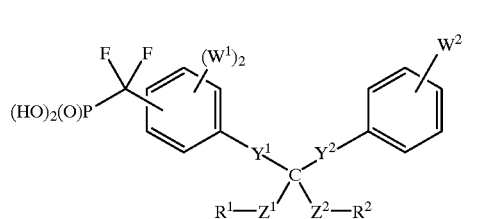

The invention also encompasses pharmaceutical compositions and methods of treating or preventing PTP-1B mediated diseases.

23 Claims, No Drawings

PHOSPHONIC ACIDS DERIVATIVES AS INHIBITORS OF PROTEIN TYROSINE PHOSPHATE 1B (PTP-1B)

CROSS REFERENCE TO RELATED APPLICATIONS

This application is based on, and claims priority from, Provisional Application Ser. Nos. 60/101,164, filed Sep. 21, 1998 and 60/127,420, filed Apr. 1, 1999, which are hereby incorporated by reference in their entirety.

BACKGROUND OF THE INVENTION

This invention relates to a novel class of phosphonic acid derivatives as inhibitors of PTP-1B.

Protein tyrosine phosphates as (Peptizes) are a large family of transmembrane or intracellular enzymes that dephosphorylate substrates involved in a variety of regulatory processes (Fischer et al., 1991, Science 253:401–406). Protein tyrosine phosphatase-1B (PTP-1B) is a ~50 kd intracellular protein present in abundant amounts in various human tissues (Charbonneau et al., 1989, Proc. Natl. Acad. Sci. USA 86:5252–5256; Goldstein, 1993, Receptor 3:1–15).

Determining which proteins are substrates of PTP-1B has been of considerable interest. One substrate which has aroused especial interest is the insulin receptor. The binding of insulin to its receptor results in autophosphorylation of the receptor, most notably on tyrosines 1146, 1150, and 1151 in the kinase catalytic domain (White & Kahn, 1994, J. Biol. Chem. 269:1–4). This causes activation of the insulin receptor tyrosine kinase, which phosphorylates the various insulin receptor substrate (IRS) proteins that propagate the insulin signaling event further downstream to mediate insulin's various biological effects.

Seely et al., 1996, Diabetes 45:1379–1385 (Seely) studied the relationship of PTP-1B and the insulin receptor in vitro. Seely constructed a glutathione S-transferase (GST) fusion protein of PTP-1B that had a point mutation in the PTP-1B catalytic domain. Although catalytically inactive, this fusion protein was able to bind to the insulin receptor, as demonstrated by its ability to precipitate the insulin receptor from purified receptor preparations and from whole cell lysates derived from cells expressing the insulin receptor.

Ahmad et al., 1995, J. Biol. Chem. 270:20503–20508 used osmotic loading to introduce PTP-1B neutralizing antibodies into rat KRC-7 hepatoma cells. The presence of the antibody in the cells resulted in an increase of 42% and 38%, respectively, in insulin stimulated DNA synthesis and phosphatidyinositol 3' kinase activity. Insulin receptor autophosphorylation and insulin receptor substrate-1 tyrosine phosphorylation were increased 2.2 and 2.0-fold, respectively, in the antibody-loaded cells. The antibody-loaded cells also showed a 57% increase in insulin stimulated insulin receptor kinase activity toward exogenous peptide substrates.

Thus, inhibitors of PTP-1B improve insulin-sensitivity and have utility in preventing or treating Type 1 and Type 2 diabetes, improving glucose tolerance and insulin-sensitivity when there is insulin-resistance. Also, the compounds are useful in treating or preventing obesity. In addition, the compounds are of use in treating or preventing cancer, neurodegenerative diseases and the like.

SUMMARY OF THE INVENTION

A compound represented by formula I:

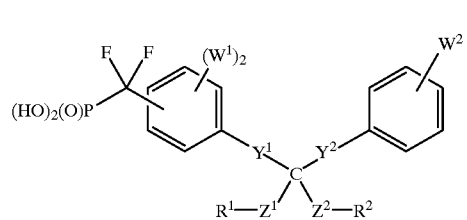

or a pharmaceutically acceptable salt thereof, wherein:

$R^1$ is selected from the group consisting of: $C_{1-10}$alkyl $(R^a)_{0-7}$, $C_{2-10}$alkenyl$(R^a)_{0-7}$, Aryl$(R^a)_{0-7}$ and Het $(R^a)_{0-7}$;

$R^2$ is selected from the group consisting of $C_{1-6}$alkyl $(R^a)_{0-7}$, Aryl$(R^a)_{0-7}$ and Het$(R^a)_{0-7}$.

When present, each $R^a$ independently represents a member selected from the group consisting of: Aryl, OH, halo, $CO_2H$, $CO_2C_{1-6}$alkyl, $OC_{1-10}$alkyl, $S(O)_yC_{1-6}$alkyl, $S(O)_y NR^{3'}R^{4'}$, Het and —$P(O)(OH)_2$;

$Y^1$ and $Y^2$ represent —$(CR^3R^4)_a$—X—$(CR^3R^4)_b$— wherein a and b are integers 0–1 such that the sum of a and b equals 0, 1 or 2, X represents a bond, O, $S(O)_y$, $NR^{3'}$, C(O), OC(O), C(O)O, C(O)$NR^{3'}$, $NR^{3'}C(O)$ or —CH=CH—, and $R^3$ and $R^4$ are independently H, halo, $C_{1-10}$alkyl or halo$C_{1-10}$alkyl, or $R^3$ and $R^4$ taken together with any intervening atoms represent a 3–7 membered ring;

$R^{3'}$ is selected from the group consisting of: H, $C_{1-6}$alkyl, halo$C_{1-6}$alkyl, OH, $C(O)C_{1-6}$ alkyl, C(O)Aryl, C(O)Het, $C(O)C_{1-6}$ haloalkyl, Aryl and Het;

$Z^1$ and $Z^2$ represent —$(CR^3R^4)_a$—X—$(CR^3R^4)_b$— wherein X, a, b, $R^3$ and $R^4$ are as defined, or $Z^1$ and $Z^2$ are taken in conjunction with $R^1$ and $R^2$ and represent in combination

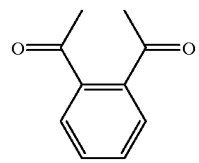

wherein $R^1$ and $R^2$ represent carbonyl groups, or —$CH_2NR^1C(O)NR^2CH_2$—, with $R^1$ and $R^2$ as originally defined;

$W^1$ and $W^2$ are each independently selected from the group consisting of: H, OH, CN, halo, $OC_{1-6}$alkyl $(R^a)_{0-7}$, $S(O)_yC_{1-6}$alkyl$(R^a)_{0-7}$, with y equal to 0–2, $S(O)_3H$, CN, $C_{1-6}$alkyl$(R^a)_{0-7}$, $N_3$, $CO_2H$, $CO_2C_{1-6}$alkyl$(R^a)_{0-7}$, $CO_2C_{2-6}$ alkenyl$(R^a)_{0-7}$, $C(O)C_{1-6}$alkyl $(R^a)_{0-7}$, $C(O)NR^{3'}R^{4'}$, $S(O)_yNR^{3'}R^{4'}$, $NR^{3'}R^{4'}$ and Het, wherein $R^{3'}$ is as defined above and $R^{4'}$ is selected from the group consisting of: H, $C_{1-6}$alkyl, halo$C_{1-6}$alkyl, Aryl and Het, or the two $W^1$ groups taken in combination represent a fused phenyl ring;

Aryl represents a 6–14 membered aromatic ring system;

and Het represents a 5–10 membered aromatic ring system containing 1–4 heteroatoms, 0–4 of which are N atoms and 0–1 of which are O or $S(O)_y$ wherein y is as previously defined, and 0–2 carbonyl groups.

DETAILED DESCRIPTION OF THE INVENTION

In one aspect of the invention, a compound is disclosed represented by formula I:

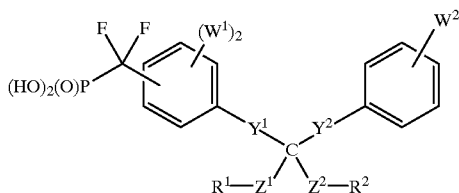

or a pharmaceutically acceptable salt thereof, wherein:

$R^1$ is selected from the group consisting of: $C_{1-10}$alkyl $(R^a)_{0-7}$, $C_{2-10}$alkenyl$(R^a)_{0-7}$, Aryl$(R^a)_{0-7}$ and Het $(R^a)_{0-7}$;

$R^2$ is selected from the group consisting of $C_{1-6}$alkyl $(R^a)_{0-7}$, Aryl$(R^a)_{0-7}$ and Het$(R^a)_{0-7}$, when present, each $R^a$ independently represents a member selected from the group consisting of: Aryl, OH, halo, $CO_2H$, $CO_2C_{1-6}$alkyl, $OC_{1-10}$alkyl, $S(O)_yC_{1-6}$alkyl, $S(O)_yNR^{3'}R^{4'}$, Het and —P(O)(OH)$_2$;

$Y^1$ and $Y^2$ represent —(CR$^3$R$^4$)$_a$—X—(CR$^3$R$^4$)$_b$— wherein a and b are integers 0–1 such that the sum of a and b equals 0, 1 or 2, X represents a bond, O, $S(O)_y$, NR$^{3'}$, C(O), OC(O), C(O)O, C(O)NR$^{3'}$, NR$^{3'}$C(O) or —CH=CH—, and R$^3$ and R$^4$ are independently H, halo, $C_{1-10}$alkyl or halo$C_{1-10}$alkyl, or R$^3$ and R$^4$ taken together with any intervening atoms represent a 3–7 membered ring;

$R^{3'}$ is selected from the group consisting of: H, $C_{1-6}$alkyl, halo$C_{1-6}$alkyl, OH, C(O)$C_{1-6}$ alkyl, C(O)Aryl, C(O) Het, C(O)$C_{1-6}$ haloalkyl, Aryl and Het;

$R^{4'}$ is selected from the group consisting of: H, $C_{1-6}$alkyl, halo$C_{1-6}$alkyl, Aryl and Het;

$Z^1$ and $Z^2$ each represent —(CR$^3$R$^4$)$_a$—X—(CR$^3$R$^4$)$_b$— wherein X, a, b, R$^3$ and R$^4$ are as defined and are defined independently for Z$^1$ and Z$^2$, or Z$^1$ and Z$^2$ are taken in conjunction with R$^1$ and R$^2$ and represent in combination

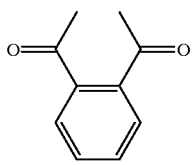

wherein R$^1$ and R$^2$ represent carbonyl groups, or Z$^1$ and Z$^2$ together are —CH$_2$NR$^1$C(O)NR$^2$CH$_2$—, with R$^1$ and R$^2$ as originally defined;

$W^1$ and $W^2$ are each independently selected from the group consisting of: H, OH, CN, halo, $OC_{1-6}$alkyl $(R^a)_{0-7}$, $S(O)_yC_{1-6}$alkyl$(R^a)_{0-7}$, with y equal to 0–2, $S(O)_3H$, CN, $C_{1-6}$alkyl$(R^a)_{0-7}$, N$_3$, $CO_2H$, $CO_2C_{1-6}$alkyl$(R^a)_{0-7}$, $CO_2C_{2-6}$ alkenyl$(R^a)_{0-7}$, $C(O)C_{1-6}$alkyl $(R^a)_{0-7}$, C(O)NR$^{3'}$R$^{4'}$, $S(O)_yNR^{3'}R^{4'}$, NR$^{3'}$R$^{4'}$ and Het, wherein R$^{3'}$ and R$^{4'}$ are as defined above, or the two W$^1$ groups taken in combination represent a fused phenyl ring;

Aryl represents a 6–14 membered aromatic ring system;

and Het represents a 5–10 membered aromatic ring system containing 1–4 heteroatoms, 0–4 of which are N atoms and 0–1 of which are O or $S(O)_y$ wherein y is as previously defined, and 0–2 carbonyl groups.

In another aspect of the invention that is of particular interest, W$^1$ and W$^2$ are independently selected from the group consisting of:

(a) hydrogen,
(b) halo,
(c) $OC_{1-6}$alkyl$(R^a)_{0-7}$,
(d) $SC_{1-6}$alkyl$(R^a)_{0-7}$,
(e) $C_{1-6}$alkyl$(R^a)_{0-7}$,
(f) $CO_2H$,
(g) $CO_2$—$C_{1-6}$alkyl$(R^a)_{0-7}$,
(h) OH,
(l) N(R$^{3'}$)(R$^{4'}$) and
(m) $C(O)C_{1-6}$alkyl$(R^a)_{0-7}$, Within this subset, all other variables are as originally defined.

More preferably, each W$^1$ represents H, and W$^2$ represents $C_{1-6}$alkyl$(R^a)_{0-7}$, and most preferably W$^2$ represents —CF$_2$—PO$_3$H$_2$. Within this aspect of the invention, all other variables are as described with respect to formula I.

In another aspect of the invention that is of particular interest, Het is selected from the group consisting of:

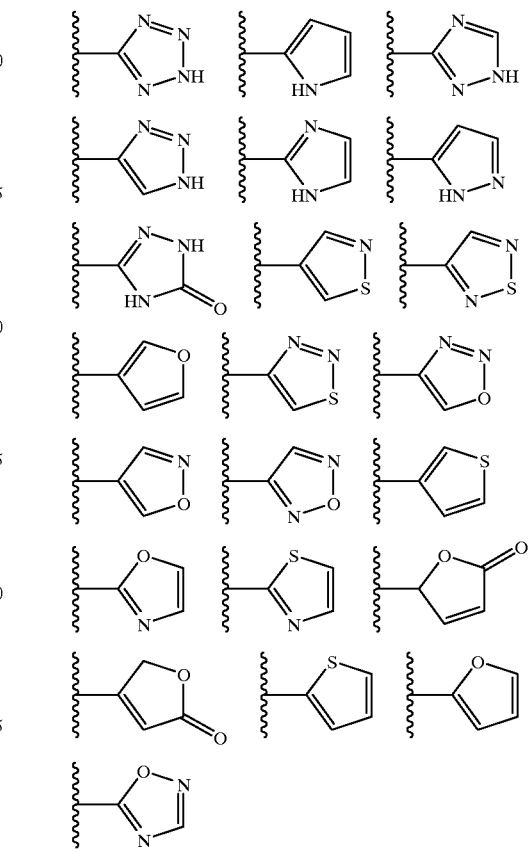

Within this subset, all other variables are as originally defined.

Another subset of compounds that is of particular interest includes compounds of formula I wherein:

Y$^1$ and Y$^2$ are each independently selected from the group consisting of:

(a) —CH$_2$—,
(b) —O—CH$_2$—,
(c) —CH$_2$—O—,
(d) —CH$_2$—O—CH$_2$—,
(e) —S—CH$_2$—,
(f) —CH$_2$—S—,
(g) —CH$_2$—S—CH$_2$—,
(h) —S(O)$_2$—CH$_2$—,
(i) —CH$_2$—S(O)$_2$—,
(j) —CH$_2$—S(O)$_2$—CH$_2$—,
(k) —S(O)$_2$—,
(l) —S—,
(m) —O—, and
(n) —NR3'-.

Within this subset, all other variables are as originally defined.

More preferably, Y$^1$ and Y$^2$ are selected from the group consisting of: (a) —CH$_2$—, (b) —O—CH$_2$—, (c) —CH$_2$—O—, (d) —CH$_2$—O—CH$_2$—, (e) —S—CH$_2$—, (f) —CH$_2$—S— and (g) —CH$_2$—S—CH$_2$—. Within this subset, all other variables are as originally defined.

Another subset of compounds that is of particular interest includes compounds of formula I wherein Z$^1$ and Z$^2$ are each independently selected from the group consisting of:
(a) —C(O)—O—,
(b) —C(O)—NH—,
(c) —C(O)—
(d) —CH$_2$—O—,
(e) —CH$_2$—,
(f) —CH$_2$—O—CH$_2$—
(g) —CH$_2$—S—
(h) —CH$_2$—S—CH$_2$—
(i) —S(O)$_2$—,
(j) —CH$_2$—S(O)$_2$—
(k) —CH$_2$—S(O)$_2$—CH$_2$—
(l) —S—,
(m) —O—,
(n) —NH—,
(o) —O—C(O)—,
(p) —NH—C(O)—,
(q) —O—CH$_2$—,
(r) —S—CH$_2$—,
(s) —S(O)$_2$—CH$_2$— and
(t) a direct bond.

Within this subset, all other variables are as originally defined.

More preferably, Z$^1$ and Z$^2$ are each independently selected from the group consisting of: (a) —C)O)—O—, (c) —C(O)—, (d) —CH$_2$—O—, (e) —CH$_2$—, (f) —CH$_2$—O—CH$_2$—, (g) —CH$_2$—S—, (h) —CH$_2$—S—CH$_2$—, (m) —O—, (o) —O—C(O)—, and (t) a direct bond. Within this subset, all other variables are as originally defined.

In another aspect of the invention that is of particular interest, R$^1$ and R$^2$ are each independently selected from the group consisting of:
(a) C$_1$–C$_{10}$alkyl,
(b) C$_1$–C$_{10}$fluoroalkyl,
(c) unsubstituted, mono-, di- or tri-substituted phenyl wherein the substituents are selected from the group consisting of:
(1) halo,
(2) C$_{1-10}$alkoxy,
(3) C$_{1-6}$alkylthio,
(4) CF$_3$,
(5) C$_{1-6}$alkyl,
(6) —CO$_2$H and
(7) —CO$_2$—C$_{1-4}$alkyl,
(d) unsubstituted, mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2 or 3 additional N atoms; said substituents are selected from the group consisting of:
(1) halo,
(2) C$_{1-6}$alkoxy,
(3) C$_{1-6}$alkylthio,
(4) CF$_3$,
(5) C$_{1-6}$alkyl,
(6) —CO$_2$H, and
(7) —CO$_2$—C$_{1-4}$alkyl,
(e) benzoheteroaryl which includes the benzo fused analogs of (d). Within this subset, all other variables are as originally defined.

In another more preferred aspect of the invention, a compound of formula I is described, wherein:

W$^1$ and W$^2$ are independently selected from the group consisting of:
(a) hydrogen,
(b) halo,
(c) OC$_{1-6}$alkyl(R$^a$)$_{0-7}$,
(d) SC$_{1-6}$alkyl(R$^a$)$_{0-7}$,
(e) C$_{1-6}$alkyl(R$^a$)$_{0-7}$,
(f) CO$_2$H,
(g) CO$_2$—C$_{1-6}$alkyl(R$^a$)$_{0-7}$,
(h) OH,
(l) N(R$^{3'}$)(R$^{4'}$) and
(m) C(O)C$_{1-6}$alkyl(R$^a$)$_{0-7}$;

Y$^1$ and Y$^2$ are each independently selected from the group consisting of:
(a) —CH$_2$—,
(b) —O—CH$_2$—,
(c) —CH$_2$—O—,
(d) —CH$_2$—O—CH$_2$—,
(e) —S—CH$_2$—,
(f) —CH$_2$—S—,
(g) —CH$_2$—S—CH$_2$—,
(h) —S(O)$_2$—CH$_2$—,
(i) —CH$_2$—S(O)$_2$—,
(j) —CH$_2$—S(O)$_2$—CH$_2$—,
(k) —S(O)$_2$—,
(l) —S—,
(m) —O—, and
(n) —NR3'-;

Z$^1$ and Z$^2$ are each independently selected from the group consisting of:
(a) —C(O)—O—,
(b) —C(O)—NH—,
(c) —C(O)—
(d) —CH$_2$—O—,
(e) —CH$_2$—,
(f) —CH$_2$—O—CH$_2$—
(g) —CH$_2$—S—
(h) —CH$_2$—S—CH$_2$—
(i) —S(O)$_2$—,
(j) —CH$_2$—S(O)$_2$—
(k) —CH$_2$—S(O)$_2$—CH$_2$—
(l) —S—, (m) —O—,
(n) —NH—,
(o) —O—C(O)—,
(p) —NH—C(O)—,
(q) —O—CH$_2$—,
(r) —S—CH$_2$—,
(s) —S(O)$_2$—CH$_2$— and
(t) a direct bond;

$R^1$ and $R^2$ are each independently selected from the group consisting of:
(a) $C_1$-$C_{10}$alkyl,
(b) $C_1$-$C_{10}$fluoroalkyl,
(c) unsubstituted, mono-, di- or tri-substituted phenyl wherein the substituents are selected from the group consisting of:
  (1) halo,
  (2) $C_{1-10}$alkoxy,
  (3) $C_{1-6}$alkylthio,
  (4) $CF_3$,
  (5) $C_{1-6}$alkyl,
  (6) —CO$_2$H and
  (7) —CO$_2$—$C_{1-4}$alkyl,
(d) unsubstituted, mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2 or 3 additional N atoms; said substituents are selected from the group consisting of:
  (1) halo,
  (2) $C_{1-6}$alkoxy,
  (3) $C_{1-6}$alkylthio,
  (4) $CF_3$,
  (5) $C_{1-6}$alkyl,
  (6) —CO$_2$H, and
  (7) —CO$_2$—$C_{1-4}$alkyl,
(e) benzoheteroaryl which includes the benzo fused analogs of (d). Within this subset, all other variables are as originally defined.

In another more preferred aspect of the invention, a compound of formula I is described, wherein:

heteroaryl (Het) is selected from the group consisting of:

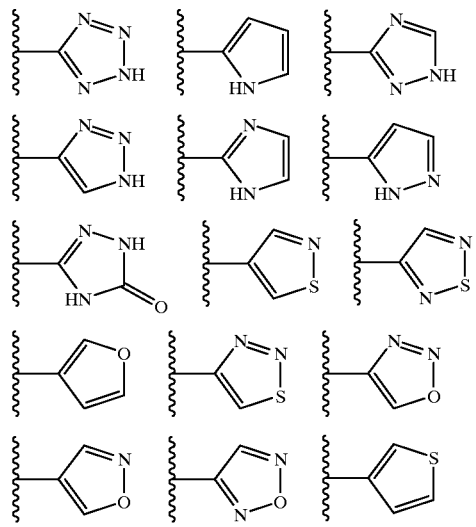

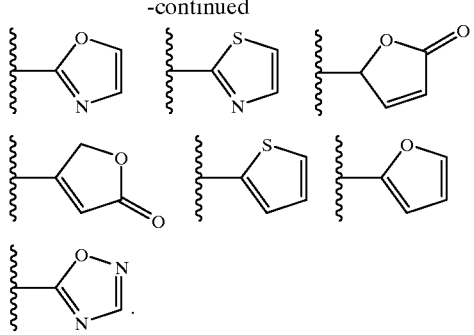

Exemplifying this invention are:
2,2-di{4-[difluoro(phosphono)methyl]benzyl}malonic acid, benzyl methyl ester;
2,2-di{4-[difluoro(phosphono)methyl]benzyl}malonic acid, dibenzyl ester;
2,2-di{4-[difluoro(phosphono)methyl]benzyl}malonic acid, diisopropyl ester;
2,2-di{4-[difluoro(phosphono)methyl]benzyl}-3-methoxy-3-oxopropanoic acid;
3-(benzylamino)-2,2-di{4-[difluoro(phosphono)methyl]benzyl}-3-oxopropanoic acid, methyl ester;
2,2-di{4-[difluoro(phosphono)methyl]benzyl}malonic acid;
2-{4-[3-(benzyloxy)-2-{4-[difluoro(phosphono)methyl]benzyl}-2-(methoxycarbonyl)-3-oxopropyl]phenyl}-2,2-difluoroacetic acid;
2-{4-[difluoro(phosphono)methyl]benzyl}-2-[4-(phosphonomethyl)benzyl]malonic acid, dibenzyl ester;
2-(4-carboxybenzyl)-2-{4-[difluoro(phosphono)methyl]benzyl}malonic acid, dibenzyl ester;
2-Benzyl-2-{4-[difluoro(phosphono)methyl]benzyl}malonic acid, dibenzyl ester;
2,2-di{4-[difluoro(phosphono)methyl]benzyl}-1,3-propane-diol, dibenzyl ether;
2,2-di{4-[difluoro(phosphono)methyl]benzyl}-1,3-propane-diol;
2-{4-[difluoro(phosphono)methyl]benzyl}-2-[4-(methylsulfonyl)benzyl]malonic acid, dibenzyl ester;
2-{4-[difluoro(phosphono)methyl]benzyl}-2-{4-[(methylsulfonyl)methyl]benzyl}malonic acid, dibenzyl ester, and
2-{4-[difluoro(phosphono)methyl]benzyl}-2-{4-[(ethylsulfonyl)methyl]benzyl}malonic acid, dibenzyl ester;
2-[4-(3-(benzyloxy)-2-[(benzyloxy)carbonyl]-2-{4-[difluoro(phosphono)methyl]benzyl}-3-oxopropyl)phenyl]-2,2-difluoroacetic acid;
(4-(2-[O4-(aminocarbonyl)benzyl]-3-(benzyloxy)-2-[(benzyloxycarbonyl]-3-oxopropy}phenyl)(difluoro)methylphosphonic acid;
{4-[2-{4-[difluoro(phosphono)methyl]benzyl}-3-isopropoxy-2-(isopropoxymethyl)propyl]phenyl}(difluoro)methyl phosphonic acid;
(4-{3-(benzyloxy)-2-[((benzyloxy)carbonyl]-3-oxo-2-[4-(trifluoromethyl)benzyl]propyl}phenyl)(difluoro)methylphosphonic acid;
(4-{3-(benzyloxy)-2-[(benzyloxy)carbonyl]-3-oxo-2-[4-(trifluoromethoxy)benzyl]propyl}phenyl)(difluoro)methylphosphonic acid;

(4-2-benzyl-3-(benzyloxy)-2-[(benzyloxy)methyl]
propylphenyl)(difluoro)methylphosphonic acid;
(4-(3-(benzyloxy)-2-[(benzyloxy)carbonyl]-2-{4-
[(dimethylamino)sulfonyl]benzyl)-3-oxopropyl)
phenyl](difluoro)methylphosphonic acid;
(4-{2-{4-[(acetylamino)sulfonyl]benzyl}-3-(benzyloxy)-
2-[(benzyloxy)carbonyl]-3-oxopropyl}phenyl)
difluoro)methylphosphonic acid;
(4-{3-(benzyloxy)-2-[(benzyloxy)carbonyl]-2-[(1,3-
dioxo-1,3-dihydro-2H-isoindol-2-yl)methyl]-3-
oxopropyl}phenyl(difluoro)methylphosphonic acid;
(4-{3-(benzyloxy)-2-[(benzyloxy)carbonyl]-3-oxo-2-[4-
(1,2,3-thiadiazol-4-yl)benzyl]propyl}phenyl)(difluoro)
methylphosphonic acid;
{4-[(2-{4-[difluoro(phosphono)methyl]benzyl}-1,3-
dioxo-2,3-dihydro-1H-inden-2-yl)methyl)phenyl}
(difluoro)methylphosphonic acid;
2-[4-(3-(Benzyloxy)-2-[(benzyloxy)methyl]-2-4-
[difluoro(phosphono)methyl]benzylpropyl)phenyl]-2,
2-difluoroacetic acid;
(4-(2-[4-(aminosulfonyl)benzyl)-3-(benzyloxy)-2-
[(benzyloxy)methyl]propyl)phenyl)(difluoro)
methylphosphonic acid;
[4-(2-{4-[difluoro(phosphono)methyl]benzyl}-3-oxo-2,
3-diphenylpropyl)phenyl](difluoro)methylphosphonic
acid;
di{4-[difluoro(phosphono)methyl]benzyl}-bis(2-
benzothiazolyl)methane difluoro[4-(3-oxo-2,3-
diphenylpropyl)phenyl]methylphosphonic acid;
2-[4-(2-4-[Difluoro(phosphono)methyl]benzyl-3-oxo-2,
3-diphenylpropyl)phenoxy]-2,2-difluoroacetic acid;
(4-{2-{4-[difluoro(phosphono)methyl]benzyl}-3-(3-
fluorophenyl)-2-[4-(methylsulfanyl)phenyl]-3-
oxopropyl}phenyl)(difluoro)methyl phosphonic acid;
(4-{2-{4-[difluoro(phosphono)methyl]benzyl}-3-(3-
fluoro-4-methoxyphenyl)-2-[4-(methylsulfonyl)
phenyl]-3-oxopropyl}phenyl)(difluoro)
methylphosphonic acid;
(4-{2-[4-(aminosulfonyl)benzyl]-3-oxo-2,3-
diphenylpropyl}phenyl)(difluoro)methylphosphonic
acid;
(4-{2-{4-[difluoro(phosphono)methyl]benzyl}-3-[4-
(methylsulfanyl)phenyl]-3-oxo-2-
phenylpropyl}phenyl)(difluoro)methylphosphonic
acid;
[4-(2-benzyl-3-oxo-2,3-diphenylpropyl)phenyl](difluoro)
methylphosphonic acid;
(4-{2-Benzotriazol-1-yl-3-[4-(difluorophosphonomethyl)
phenyl]-2-phenylpropyl}phenyl)-
difluoromethylphosphonic acid;
2-(4-(2-{4-[Difluoro(phosphono)methyl]benzyl)-3-oxo-
2,3-diphenylpropyl}phenyl]-2,2-difluoroacetic acid;
4-(2-{4-[Difluoro(phosphono)methyl]benzyl}-3-oxo-2,
3diphenylpropyl)benzoic acid;
(4-{2-{4-[difluoro(phosphono)methyl]benzyl}-3-(4-
fluorophenyl)-2-[4-(methylsulfanyl)phenyl]-3-
oxopropyl}phenyl)(difluoro)methylphosphonic acid;
(4-{2-Benzotriazol-1-yl-2-(3,4-difluorophenyl)-3-[4-
(difluorophosphonomethyl)phenyl]propyl}phenyl)
difluoromethylphosphonic acid.
{4-[2-Benzotriazol-1-yl-3-(4-bromophenyl)-2-
phenylpropyl]phenyl}difluoromethylphosphonic acid;
(4-{2-{4-[difluoro(phosphono)methyl]benzyl}-2-[4-
(methylsulfanyl)phenyl]-3-oxo-3-
phenylpropyl}phenyl)(difluoro)methylphosphonic
acid;

{4-[2-[4-(1,2-difluoro-1-phosphonoethyl)benzyl]-2,3-bis
(4-fluorophenyl)-3-oxopropyl]phenyl}(difluoro)
methylphosphonic acid;
[4-(2-4-[2-(tert-butoxy)-1,1-difluoro-2-oxoethoxy]
benzyl-3-oxo-2,3-diphenylpropyl)phenyl](difluoro)
methylphosphonic acid.

| The following abbreviations have the indicated meanings: | | |
|---|---|---|
| AA | = | arachidonic acid |
| Ac | = | acetyl |
| AIBN | = | 2.2-azobisisobutyronitrile |
| Bn | = | benzyl |
| BSA | = | bovine serum albumin |
| Bz | = | benzoyl |
| CHO | = | chinese hamster ovary |
| CMC | = | 1-cyclohexyl-3-(2-mropholinoethyl) carbodiimidemetho-p-toluenesulfonate |
| DAST | = | diethylamino sulfur trifluoride |
| DBU | = | diazabicyclo[5.4.0]undec-7-ene |
| DMAP | = | 4-(dimethylamino)pyridine |
| DMF | = | N,N-dimethylformamide |
| DMSO | = | dimethyl sulfoxide |
| $Et_3N$ | = | triethylamine |
| HATU | = | O-(7-azabenzotriazol-1-yl)-1,1,3,3-tetramethyluronium hexafluorophosphate |
| HBSS | = | Hanks balanced salt solution |
| HEPES | = | $N^1$-[2-Hydroxyethyl]piperazine-$N^4$-[2-ethanesulfonic acid] |
| HWB | = | human whole blood |
| KHMDS | = | potassium hexamethyldisilazane |
| LDA | = | lithium diisopropylamide |
| LPS | = | lipopolysaccharide |
| mCPBA | = | metachloro perbenzoic acid |
| MMPP | = | magnesium monoperoxyphthalate |
| Ms | = | methanesulfonyl = mesyl |
| MsO | = | methanesulfonate = mesylate |
| NBS | = | N-bromosuccinimide |
| NCS | = | N-chlorosuccinimide |
| NIS | = | N-iodosuccinimide |
| NSAID | = | non-steroidal anti-inflammatory drug |
| Oxone ® | = | potassium peroxymonosulfate |
| PCC | = | pyridinium chlorochromate |
| PDC | = | pyridinium dichromate |
| PPA | = | polyphosphoric acid |
| PTP | = | protein tyrosine phosphatase |
| r.t. | = | room temperature |
| rac. | = | racemic |
| Tf | = | trifluoromethanesulfonyl = triflyl |
| TFA | = | trifluoroacetic acid |
| TFAA | = | trifluoroacetic anhydride |
| TfO | = | trifluoromethanesulfonate = triflate |
| THF | = | tetrahydrofuran |
| TLC | = | thin layer chromatography |
| Ts | = | p-toluenesulfonyl = tosyl |
| TsO | = | p-toluenesulfonate = tosylate |
| Tz | = | 1H (or 2H)-tetrazol-5-yl |

| Alkyl group abbreviations | | |
|---|---|---|
| Me | = | methyl |
| Et | = | ethyl |
| n-Pr | = | normal propyl |
| i-Pr | = | isopropyl |
| n-Bu | = | normal butyl |
| i-Bu | = | isobutyl |
| s-Bu | = | secondary butyl |
| t-Bu | = | tertiary butyl |
| c-Pr | = | cyclopropyl |
| c-Bu | = | cyclobutyl |
| c-Pen | = | cyclopentyl |
| c-Hex | = | cyclohexyl |

-continued

| | Dose Abbreviations |
|---|---|
| bid | = bis in die = twice daily |
| qid | = quater in die = four times a day |
| tid | = ter in die = three times a day |

Alkyl means linear branched and cyclic structures, and combinations thereof, containing the indicated number of carbon atoms. Examples of alkyl groups include methyl, ethyl, propyl, isopropyl, butyl, s- and t-butyl, pentyl, hexyl, heptyl, octyl, nonyl, undecyl, dodecyl, tridecyl, tetradecyl, pentadecyl, eicosyl, 3,7-diethyl-2,2-dimethyl-4-propylnonyl, cyclopropyl, cyclopentyl, cycloheptyl, adamantyl, cyclododecylmethyl, 2-ethyl-1-bicyclo[4.4.0] decyl and the like.

Fluoroalkyl means alkyl groups of the indicated number of carbon atoms in which one or more hydrogen is replaced by fluorine. Examples are —CF$_3$, —CH$_2$CH$_2$F, —CH$_2$CF$_3$, c-Pr—F$_5$, c-Hex-F$_{11}$ and the like. Halo alkyl has the analogous meaning for replacement of one or more hydrogen atoms with any halogen (Cl, Br, F, and/or I).

Alkenyl means linear, branched and cyclic structures, and combinations thereof containing a double bond with the indicated number of carbon atoms. Examples of alkenyl groups include allyl, 2-butenyl, 3-butenyl, 2-pentenyl, 2-cyclopentenyl, 3-cyclopentenyl, 2-cyclohexenyl, 3-cyclohexenyl and the like.

Alkynyl means linear, branched and cyclic structures, and combinations thereof containing a triple bond with the indicated number of carbon atoms. Examples of alkenyl groups include propargyl, 2-butynyl, 3-butynyl, 2-pentynyl, cyclopropylethinyl, and the like.

Heteroaryl, as in R$^1$ and R$^2$, is intended to include, but is not limited to furany, diazinyl, imidazolyl, isooxazolyl, isothiazolyl, oxadiazolyl, oxazolyl, pyrazolyl, pyridyl, pyrrolyl, tetrazinyl, thiazolyl, thienyl, triazinyl, triazolyl, 1H-pyrrole-2,5-dionyl, 2-pyrone and 4-pyrone.

Benzoheteroaryl, is part of Het, such as is applicable to R$^1$ and R$^2$, and is intended to include fused ring systems, such as 2H-1-benzopyran-2-one, 4H-1-benzopyran-4-one, 2(3H) benzofuranone, 3(2H)benzofuranone, 2,3-dihydrobenzofuran, 2,3-dihydrobenzothiophene, indole, benzofuran, benzothiophene, benzimidazole, benzoxazole, benzothiazole, benzotriazole, benzothiadiazole, 1H-isoindole-1,3(2H)-dione, quinoline, isoquinoline, pyrrolopyridine, furopyridine and thienopyridine.

Het as used herein thus represents a 5–10 membered aromatic ring system containing 1–4 heteroatoms, 0–4 of which are N atoms and 0–1 of which are O or S(O)$_y$ wherein y is as previously defined, and 0–2 carbonyl groups, said ring system being optionally substituted with OH or NH$_2$. Examples of Het include the following:

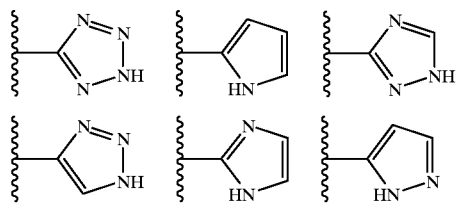

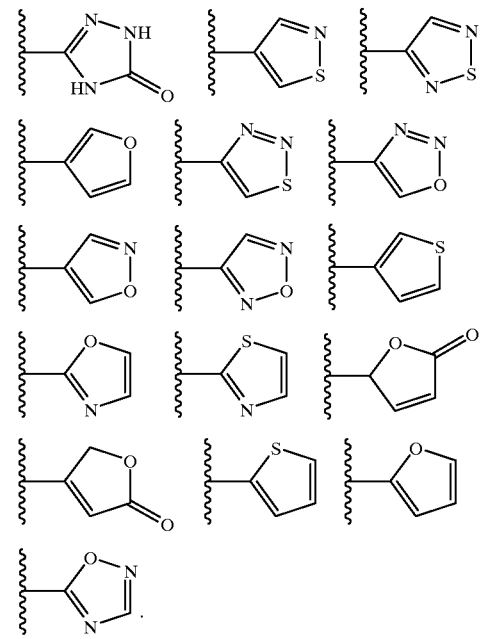

When a ring is specified optionally having one or more heteroatoms, this means that at least one heteroatom is present, selected from O, S and N, and up to 4 such heteroatoms may be present, depending upon the size of the ring specified.

Optical Isomers-Diastereomers-Geometric Isomers

Some of the compounds described herein contain one or more asymmetric centres and may thus give rise to diastereomers and optical isomers. The present invention includes all such diastereomers as well as their racemic and resolved, enantiomerically pure forms and pharmaceutically acceptable salts thereof.

Some of the compounds described herein contain olefinic double bonds, and unless specified otherwise, include both E and Z geometric isomers.

Salts

The pharmaceutical compositions of the present invention comprise a compound of Formula A as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucarnine, morpholine, piperazine, piperidine, polyamine resins, procaine, purines, theobromine, triethylamine, trimethylamine, tripropylamine, tromethamine and the like.

When the compound of the present invention is basic, salts may be prepared from pharmaceutically acceptable acids, including inorganic and organic acids. Such acids include acetic, adipic, aspartic, 1,5-naphthalenedisulfonic, benzenesulfonic, benzoic, camphorsulfonic, citric, 1,2-ethanedisulfonic, ethanesulfonic, ethylenediaminetetraacetic, fumaric, glucoheptonic, gluconic, glutamic, hydriodic, hydrobromic, hydrochloric, isethionic, lactic, maleic, malic, mandelic, methanesulfonic, mucic, 2-naphthalenesulfonic, nitric, oxalic, pamoic, pantothenic, phosphoric, pivalic, propionic, salicylic, stearic, succinic, sulfuric, tartaric, p-toluenesulfonic acid, undecanoic, 10-undecenoic, and the like. Particularly preferred are citric, hydrobromic, hydrochloric, maleic, methanesulfonic, phosphoric, sulfuric and tartaric acids.

It will be understood that in the discussion of methods of treatment which follows, references to the compounds of Formulae A and Ai are meant to include the pharmaceutically acceptable salts.

Utilities Inhibitors of PTP-1B improve insulin-sensitivity and thus have utility in preventing or treating Type 1 and Type 2 diabetes, improving glucose tolerance and insulin-sensitivity when there is insulin-resistance and in treating or preventing obesity. The compounds also exhibit a beneficial reduction in triglycerides and lipids. The PTP-1B inhibitors thus may be useful in the treatment, prevention or control of a number of conditions that accompany type 2 diabetes, including hyperlipidemia, hypertriglyceridemia, hypercholesterolemia (including raising HDL levels), atherosclerosis, vascular restenosis, irritable bowel syndrome, pancreatitis, adipose cell tumors, adipose cell carcinomas such as liposarcoma, dyslipidemia, and other disorders where insulin resistance is a component. Finally, the compounds may be used to treat or prevent cancer, neurodegenerative diseases and the like.

Pharmaceutical Compositions

For the treatment of any of these PTP-1B-mediated diseases compound A or Ai may be administered orally, topically, parenterally, by inhalation spray or rectally in dosage units containing conventional pharmaceutically acceptable carriers. The term parenteral as used herein includes subcutaneous, intravenous, intramuscular and intrasternal injection and infusion techniques. In addition to the treatment of warm-blooded animals such as mice, rats, horses, cattle, sheep, dogs, cats, etc., the compounds of the invention are useful for the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxy-ethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical composition may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a parenterally-acceptable diluent or solvent, for example as a solution in 1,3-butanediol. Examples of vehicles and solvents include water, Ringer's solution and isotonic sodium chloride. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds may also be administered in the form of suppositories. These compositions can be prepared by mixing the drug with a suitable non-irritating excipient which is solid at ordinary temperatures but molten at the body temperature and will therefore release the drug. Such materials include cocoa butter and polyethylene glycols.

For topical use, creams, ointments, gels, solutions or suspensions containing the compound are employed. (For purposes of this application, topical application includes mouth washes and gargles.) Topical formulations may include cosolvents, emulsifiers, penetration enhancers, preservatives, emollients and the like.

The pharmaceutical composition may also be further comprised of a second anti-diabetic or anti-obesity effective compound.

Dose Ranges

Dosage levels of the order of from about 0.01 mg to about 100 mg/kg of body weight per day are useful in the treatment of the above-indicated conditions, or alternatively about 0.5 mg to about 7 g per patient per day. For example, the diseases and conditions described herein may be effectively treated by the administration of from about 0.01 to 50 mg of the compound per kilogram of body weight per day, or alternatively about 0.5 mg to about 3.5 g per patient per day.

The active ingredient is typically combined with the carrier to produce a dosage form suitable for the particular patient being treated and the particular mode of administration. For example, a formulation intended for the oral administration of humans may contain from about 0.5 mg to about 5 g of the active agent, compounded with an appropriate and convenient amount of carrier material which may vary from about 5 to about 95 percent of the total composition. Representative dosage forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It is understood that the specific dose level for any particular patient will depend upon a variety of factors including the age, body weight, general health, sex, diet, time of administration, route of administration, rate of excretion, drug combination and the severity of the particular disease undergoing therapy.

Combinations with Other Drugs

In further aspects, the invention encompasses pharmaceutical compositions for treating PTP-1B-mediated diseases as defined above comprising an effective amount of the compound of Formula A or Ai as defined above and one or more ingredients such as insulin, sulfonyl ureas, PPAR alpha and/or -gamma ligands, and antiobesity drugs.

Thus, the methods of treatment or prevention described herein may further be comprised of administering to said patient a second anti-diabetic compound in an amount effective to treat or prevent diabetes.

Similarly, the methods of treatment of diabetes may comprise the administration of a cholesterol biosynthesis inhibitor, particularly an HMG-CoA reductase inhibitor, such as lovastatin, simvastatin, pravastatin, fluvastatin, atorvastatin and rivastatin, in an amount effective to improve the lipid profile. In combination with a PTP-1B inhibitor, this may be beneficial in treating or preventing atherosclerosis and other conditions that often are associated with Type 2 diabetes.

Similarly, the methods of treatment or prevention described herein may further be comprised of administering to said patient a second anti-obesity compound in an amount effective to treat or prevent obesity.

Methods of Synthesis

The compounds of the present invention can be prepared according to the following methods.

Method A

Di-tert-butyl phosphite can be deprotonated with a base such as LiN(TMS)2 and reacted with a tolualdehyde to provide alcohol 2, which may be oxidized with MnO2 or under Swernis conditions to give phosphonoketone 3. Bromination of 3 with NBS followed by fluorination with DAST affords bomide 5, which can be used to alkylate various malonates with a base to yield 7. Acid hydrolysis of 7 gives bisphosphonic acid 8.

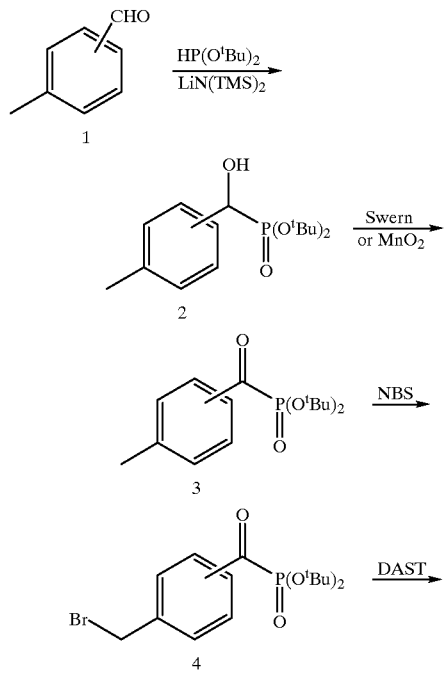

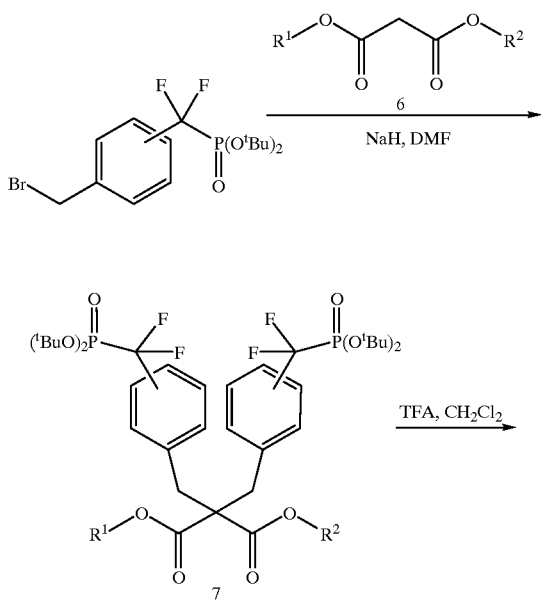

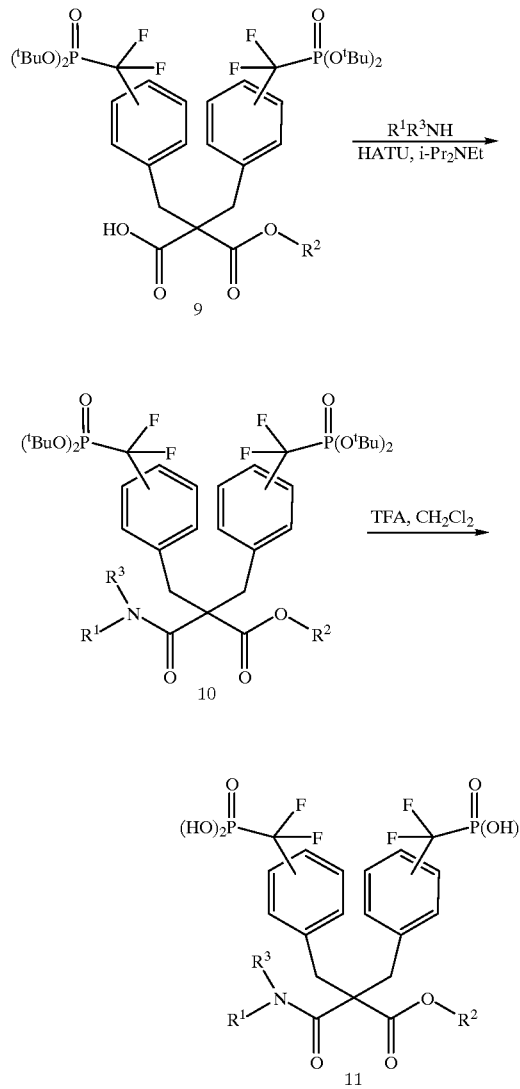

Method B

Benzylmalonate 7a can be converted to the half-malonic acid ester 9 by hydrogenolysis with $H_2$ and Pd/C. Treatment of half-malonic acid ester 9 with an amine under standard peptide coupling conditions can yield amide-ester compound 10. Acid hydrolysis of 10 gives bisphosphonic acid 11.

Method C

Dibenzylmalonate 7b can be converted to diacid 12 by hydrogenolysis with hydrogen and Pd/C. Diacid 12 can be transformed to diamide 13 under standard conditions as described in Method B. Acid hydrolysis of 13 gives bisphosphonic acid 14.

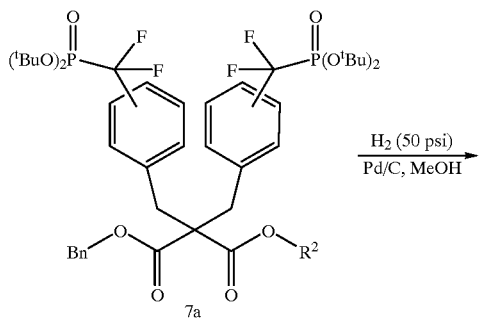

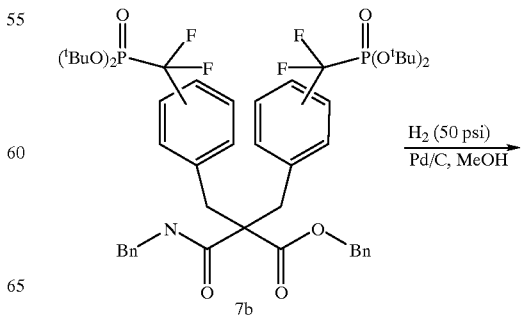

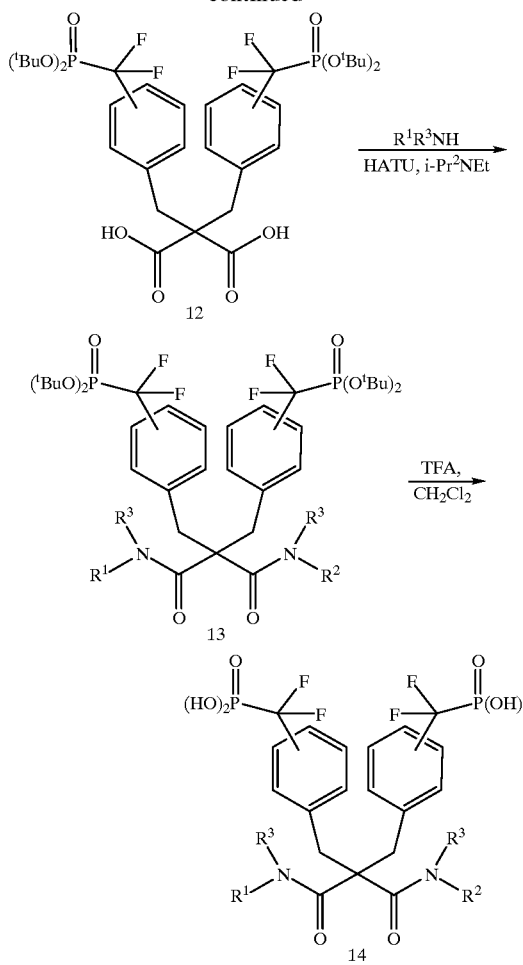

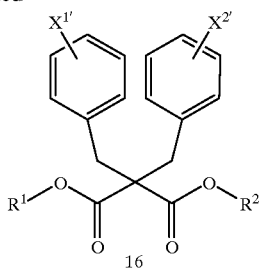

Method D

Malonate 6 can be sequentially alkylated with two different properly protected alkylating agents to give compound 16. A deprotection procedure may be required to liberate the desired functional groups from $X^{1'}$ and $X^{2'}$.

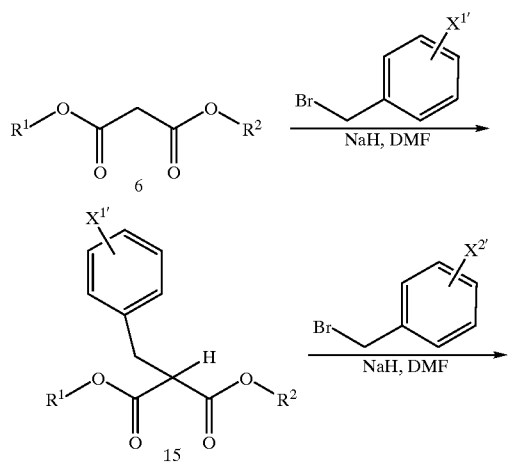

Method E

Dimethyl malonate can be alkylated with bromide 17 and a base. Reduction of the resulting alkylated dimethyl malonate 18 with LiAlH$_4$ produces diol 19, which can alkylated with appropriate alkyl halides and a base to give 20. Acidic hydrolysis of 20 provides dialdehyde 21. Reaction of 21 with deprotonated di-tert-butylphosphite affords diol 22, which, upon oxidation and fluorination, gives 23. Acid hydrolysis of 23 yields the bisphosphonic acid 24.

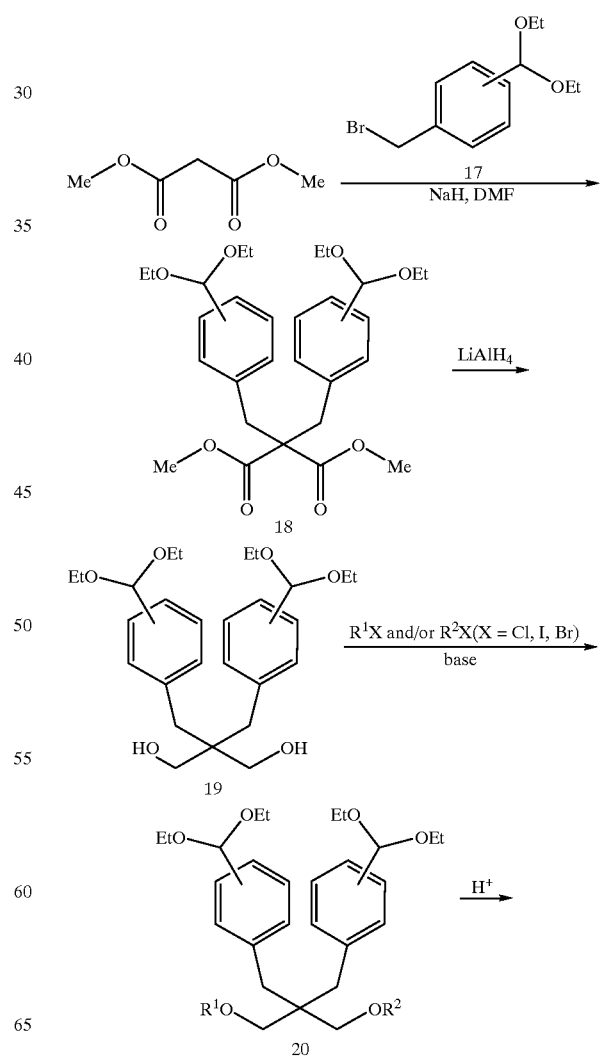

-continued

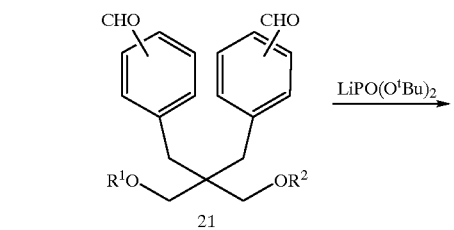
21

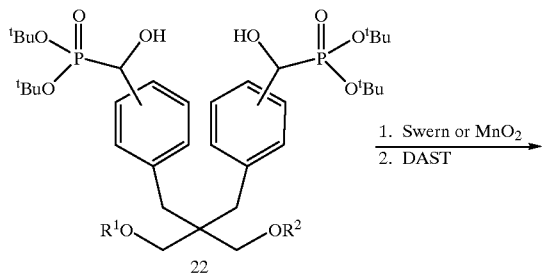
22

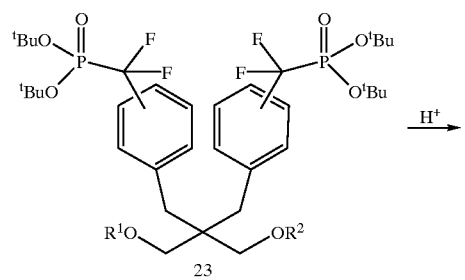
23

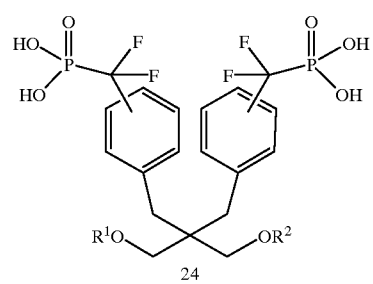
24

Method F

Ketone 25 can be sequentially alkylated with two identical or different properly protected alkylating agents to give compound 27. A deprotection procedure may be required to liberate the desired functional groups from $X^{1'}$ and $X^{2'}$.

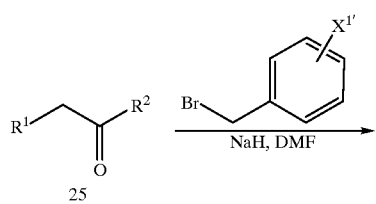
25

-continued

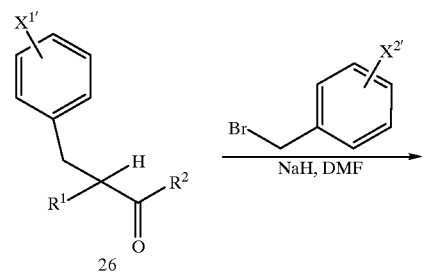
26

27

Method G

Sulphonyl-ketone 28 can be sequentially alkylated with two identical or different properly protected alkylating agents to give compound 30. A deprotection procedure may be required to liberate the desired functional groups from $X^{1'}$ and $X^{2'}$.

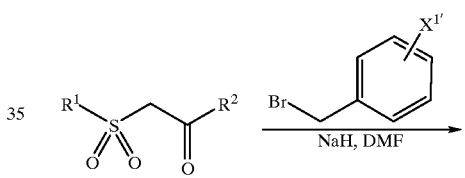
28

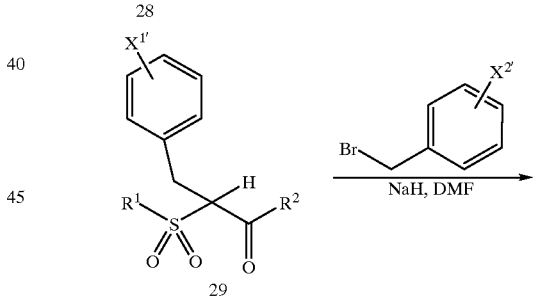
29

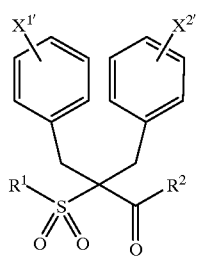
30

Method H

Bis(sulphonyl)methane 31 can be sequentially alkylated with two identical or different properly protected alkylating agents to give compound 33. A deprotection procedure may be required to liberate the desired functional groups from $X^{1'}$ and $X^{2'}$.

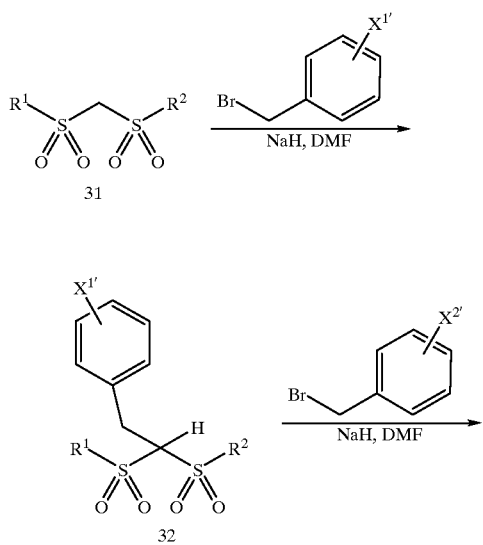

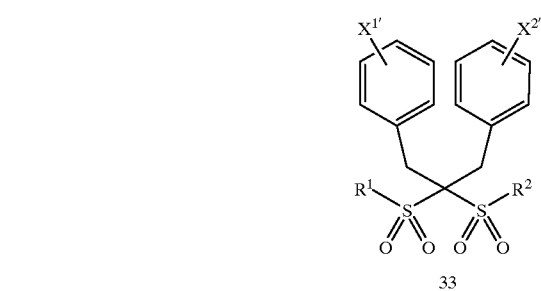

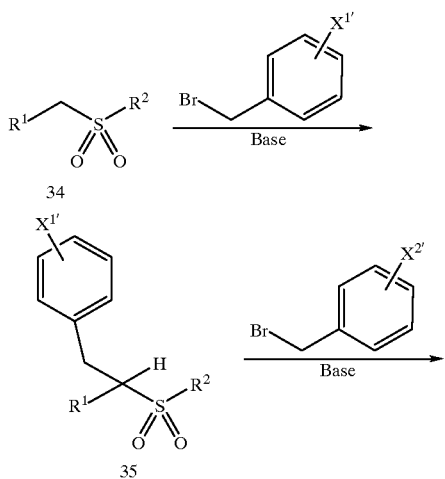

Method I

Sulphone 34 can be sequentially alkylated with two identical or different properly protected alkylating agents to give compound 36. A deprotection procedure may be required to liberate the desired functional groups from $X^{1'}$ and $X^{2'}$.

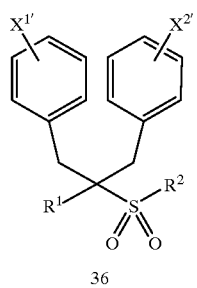

Method J

Dimethyl malonate can be alkylated sequentially with 4-bromobenzyl bromide and 1-(bromomethyl)-4-(diethoxymethyl)benzene under basic conditions to provide 38. Reduction of the resulting alkylated dimethyl malonate 38 with LiAlH$_4$ produces diol 39, which can be alkylated with appropriate alkyl halides and base to give 40. Treatment of 40 with t-butyllithium followed by diethyl oxalate yields 41. Fluorination of 41 with DAST, followed by acidic hydrolysis of the diethyl acetal moiety, provides aldehyde 42. Reaction of 42 with deprotonated di-tert-butylphosphite affords alcohol 43, which, upon oxidation and fluorination, gives 44. Hydrolysis of 44 with aqueous base, followed by acidification yields the product 45.

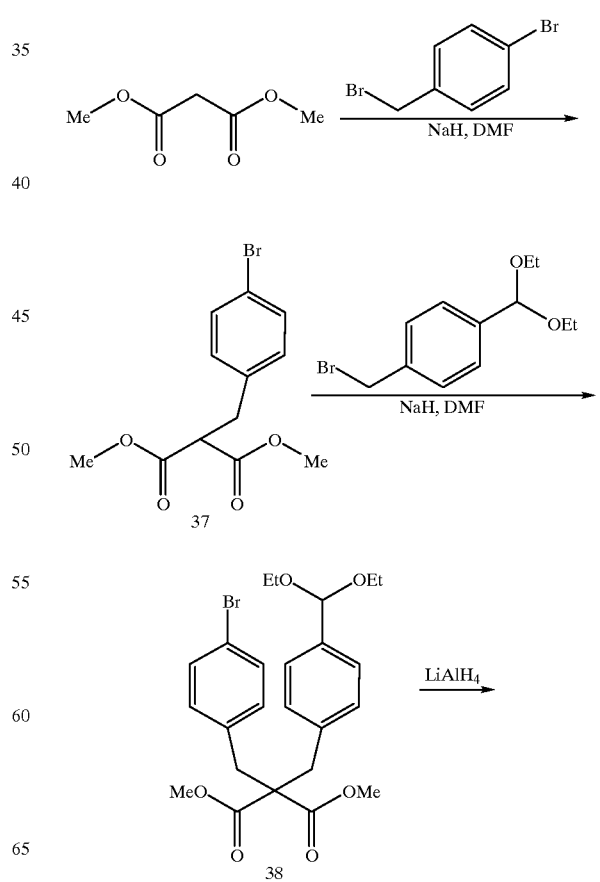

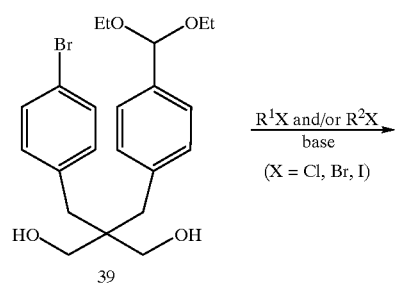
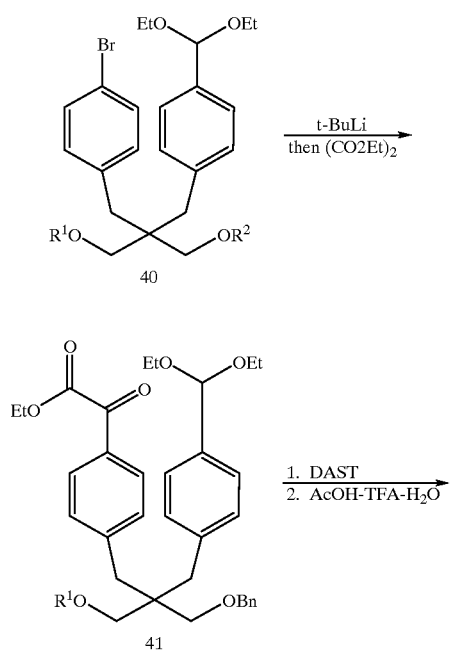
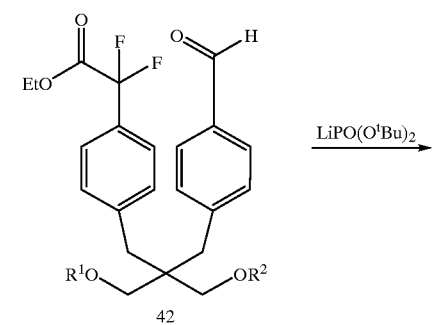
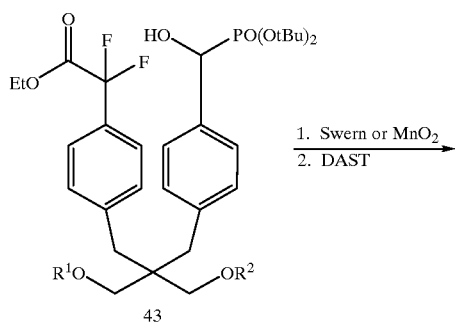

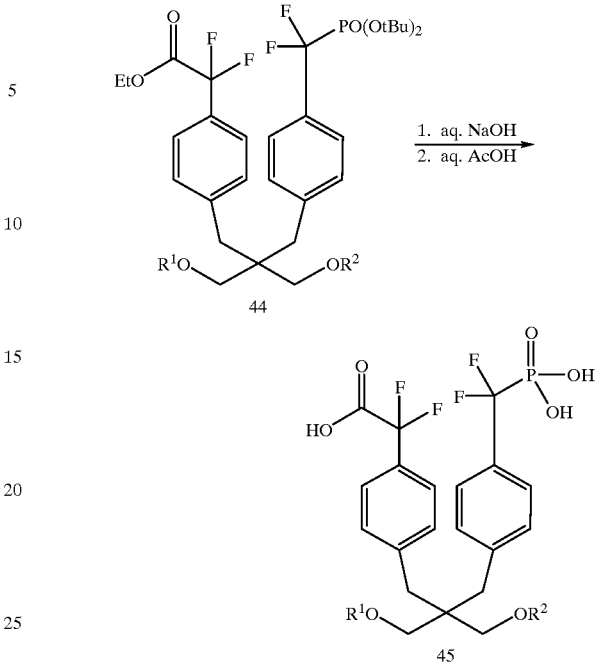

Method K

Treatment of malonic acid and 2-aminothiophenol or 2-aminophenol with an acid such as polyphosphoric acid can yield bis(2-benzoxazolyl)methane or bis(2-benzothiazolyl)methane 47 (Ref. Abbotto et al., Gazz. Chim. Ital., 124, 301, 1994), which can be alkylated with two identical or different properly protected alkylating agents to give compound 49. A deprotection procedure may be required to liberate the desired functional groups from $X^{1'}$ and $X^{2'}$.

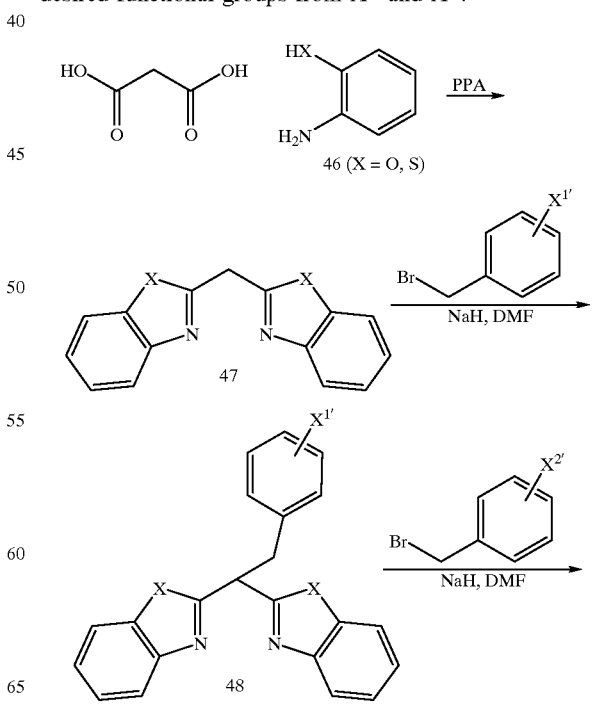

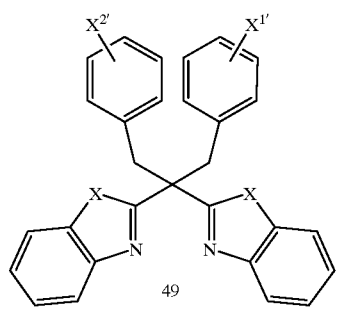

49

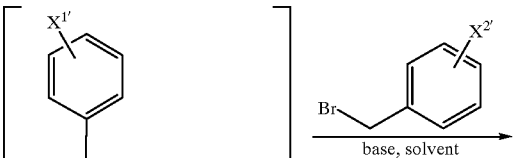

Method L

Compound 50, which contains an acidic methylene group adjacent to a heterocyclic ring, can be alkylated with two identical or different properly protected alkylating agents under basic conditions to give compound 51. A deprotection procedure may be required to liberate the desired functional groups from $X^{1'}$ and $X^{2'}$.

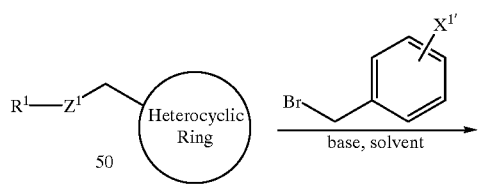

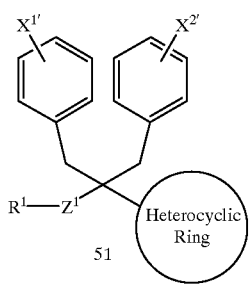

51

Representative Compounds

Table 1 and Table 2 illustrate compounds of formula I which are representative of the present invention.

TABLE 1

| | Example | Method |
|---|---|---|
| (structure) | 1 | A |
| (structure) | 2 | A |

TABLE 1-continued

| | Example | Method |
|---|---|---|
| (structure: bis[4-(difluoro-phosphono-methyl)benzyl] malonate diisopropyl ester) | 3 | A |
| (structure: bis[4-(difluoro-phosphono-methyl)benzyl] malonic acid) | 4 | B |
| (structure: bis[4-(difluoro-phosphono-methyl)benzyl] malonate methyl ester benzyl amide) | 5 | B |
| (structure: bis[4-(difluoro-phosphono-methyl)benzyl] malonic acid) | 6 | C |

TABLE 1-continued

| | Example | Method |
|---|---|---|
| [structure] | 7 | D |
| [structure] | 8 | D |
| [structure] | 9 | D |
| [structure] | 10 | D |

TABLE 1-continued

| Structure | Example | Method |
|---|---|---|
| (HO)₂P(O)CF₂—C₆H₄—CH₂—C(CH₂OCH₂Ph)₂—CH₂—C₆H₄—CF₂P(O)(OH)₂ | 11 | E |
| (HO)₂P(O)CF₂—C₆H₄—CH₂—C(CH₂OH)₂—CH₂—C₆H₄—CF₂P(O)(OH)₂ | 12 | E |
| (HO)₂P(O)CF₂—C₆H₄—CH₂—C(CO₂CH₂Ph)₂—CH₂—C₆H₄—S(O)₂Me | 13 | D |
| (HO)₂P(O)CF₂—C₆H₄—CH₂—C(CO₂CH₂Ph)₂—CH₂—C₆H₄—CH₂S(O)₂Me | 14 | D |

TABLE 1-continued

| Structure | Example | Method |
|---|---|---|
| (HO)₂P(O)-CF₂-C₆H₄-CH₂-C(CO₂CH₂Ph)₂-CH₂-C₆H₄-S(O)₂Et | 15 | D |
| (HO)₂P(O)-CF₂-C₆H₄-CH₂-C(CO₂CH₂Ph)₂-CH₂-C₆H₄-S(O)₂NH₂ | 16 | D |
| (HO)₂P(O)-CF₂-C₆H₄-CH₂-C(CO₂CH₂Ph)₂-CH₂-C₆H₄-CF₂-CO₂H | 17 | D |
| (HO)₂P(O)-CF₂-C₆H₄-CH₂-C(CO₂CH₂Ph)₂-CH₂-C₆H₄-C(O)NH₂ | 18 | D |

TABLE 1-continued

| Structure | Example | Method |
|---|---|---|
| (Compound with two (HO)₂P(O)CF₂- groups attached to para-benzyl groups on central carbon bearing two -CH₂-O-iPr groups) | 19 | E |
| (Compound with (HO)₂P(O)CF₂-C₆H₄-CH₂- and 4-CF₃-C₆H₄-CH₂- on central carbon bearing two -C(O)-O-CH₂Ph groups) | 20 | D |
| (Compound with (HO)₂P(O)CF₂-C₆H₄-CH₂- and 4-OCF₃-C₆H₄-CH₂- on central carbon bearing two -C(O)-O-CH₂Ph groups) | 21 | D |
| (Compound with (HO)₂P(O)CF₂-C₆H₄-CH₂- and PhCH₂- on central carbon bearing two -CH₂-O-CH₂Ph groups) | 22 | D & E |

TABLE 1-continued

| | Example | Method |
|---|---|---|
| (structure: 4-[(HO)$_2$P(O)CF$_2$]-C$_6$H$_4$-CH$_2$-C(CO$_2$CH$_2$Ph)$_2$-CH$_2$-C$_6$H$_4$-4-SO$_2$NMe$_2$) | 23 | D |
| (structure: 4-[(HO)$_2$P(O)CF$_2$]-C$_6$H$_4$-CH$_2$-C(CO$_2$CH$_2$Ph)$_2$-CH$_2$-C$_6$H$_4$-4-SO$_2$NHAc) | 24 | D |
| (structure: 4-[(HO)$_2$P(O)CF$_2$]-C$_6$H$_4$-CH$_2$-C(CO$_2$CH$_2$Ph)$_2$-CH$_2$-phthalimide) | 25 | D |
| (structure: 4-[(HO)$_2$P(O)CF$_2$]-C$_6$H$_4$-CH$_2$-C(CO$_2$CH$_2$Ph)$_2$-CH$_2$-C$_6$H$_4$-4-(1,2,3-thiadiazol-4-yl)) | 26 | D |

TABLE 1-continued

| | Example | Method |
|---|---|---|
| (structure) | 27 | F |
| (structure) | 28 | J |
| (structure) | 29 | |
| (structure) | 30 | F |

TABLE 1-continued

| | Example | Method |
|---|---|---|
| (structure) | 31 | K |
| (structure) | 32 | F |
| (structure) | 33 | F |
| (structure) | 34 | F |

TABLE 1-continued

| | Example | Method |
|---|---|---|
| (structure) | 35 | F |
| (structure) | 36 | F |
| (structure) | 37 | F |
| (structure) | 38 | L |

TABLE 1-continued
| | Example | Method |
|---|---|---|
| 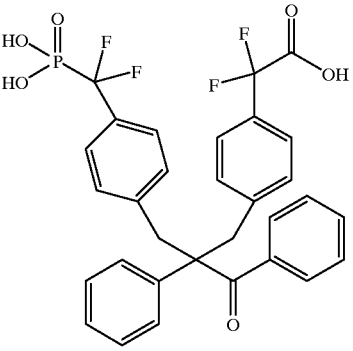 | 39 | F |
| 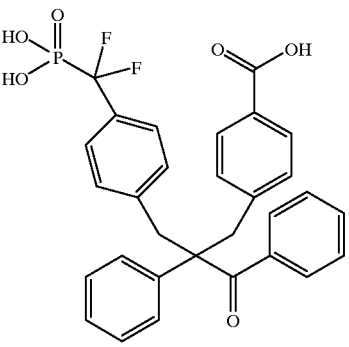 | 40 | F |
| 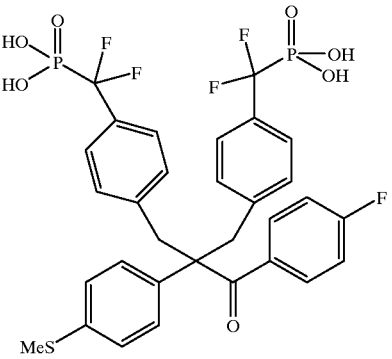 | 41 | F |
| 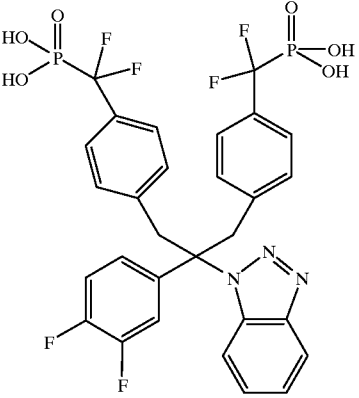 | 42 | L |

TABLE 1-continued

| Example | Method |
|---------|--------|
| 43 | L |
| 44 | F |
| 45 | F |
| 46 | F |

TABLE 2
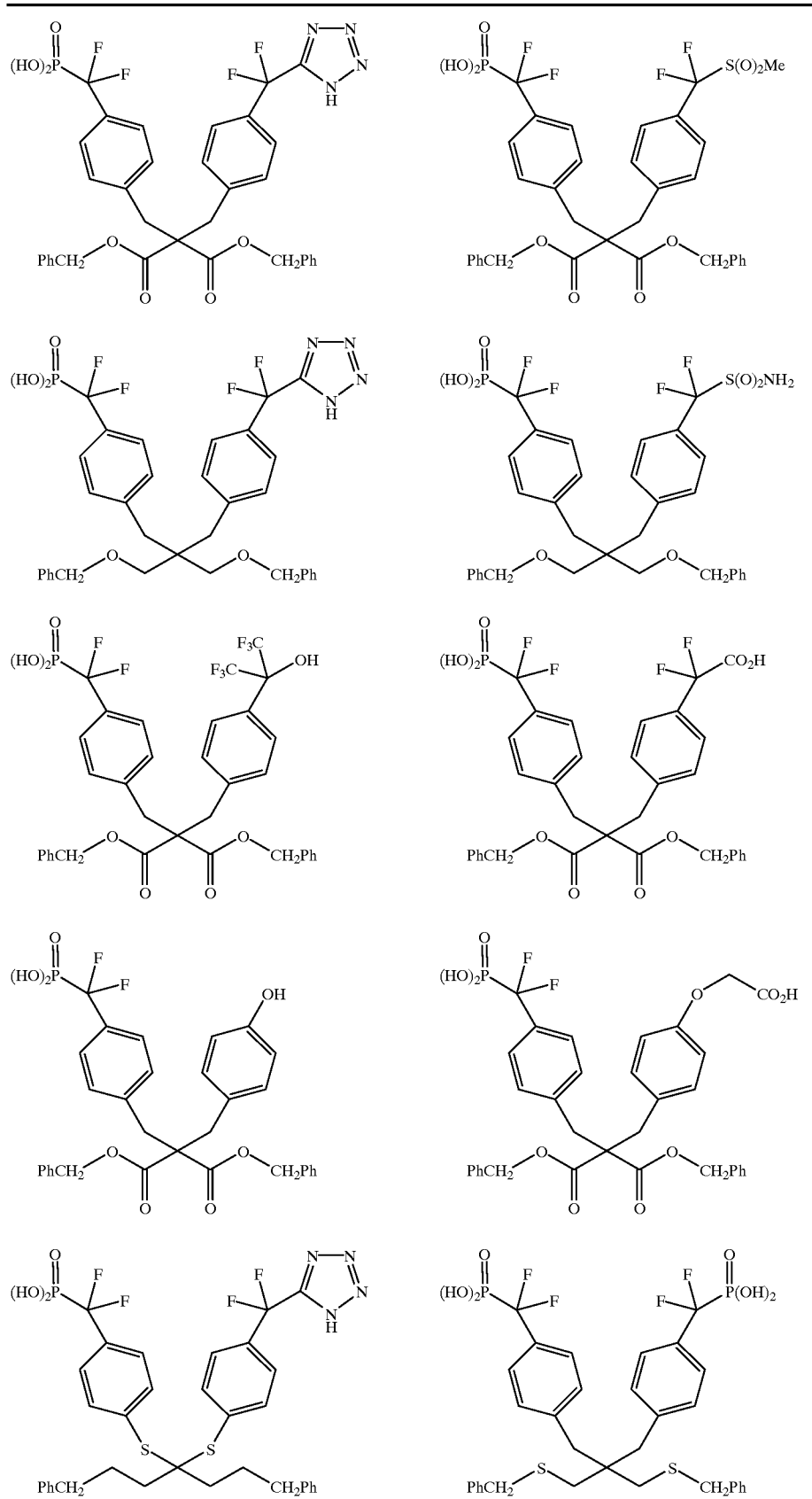

TABLE 2-continued
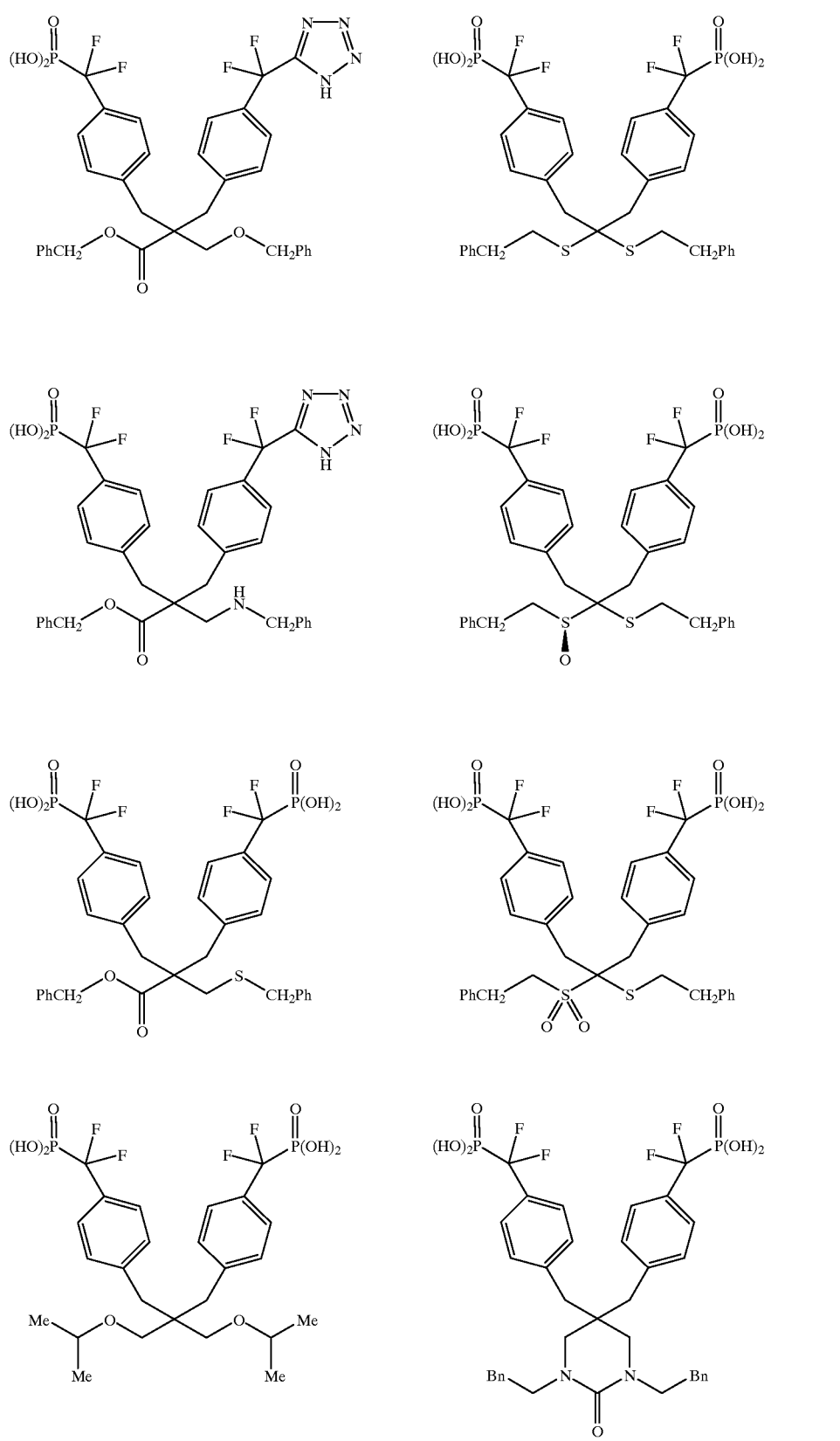

TABLE 2-continued
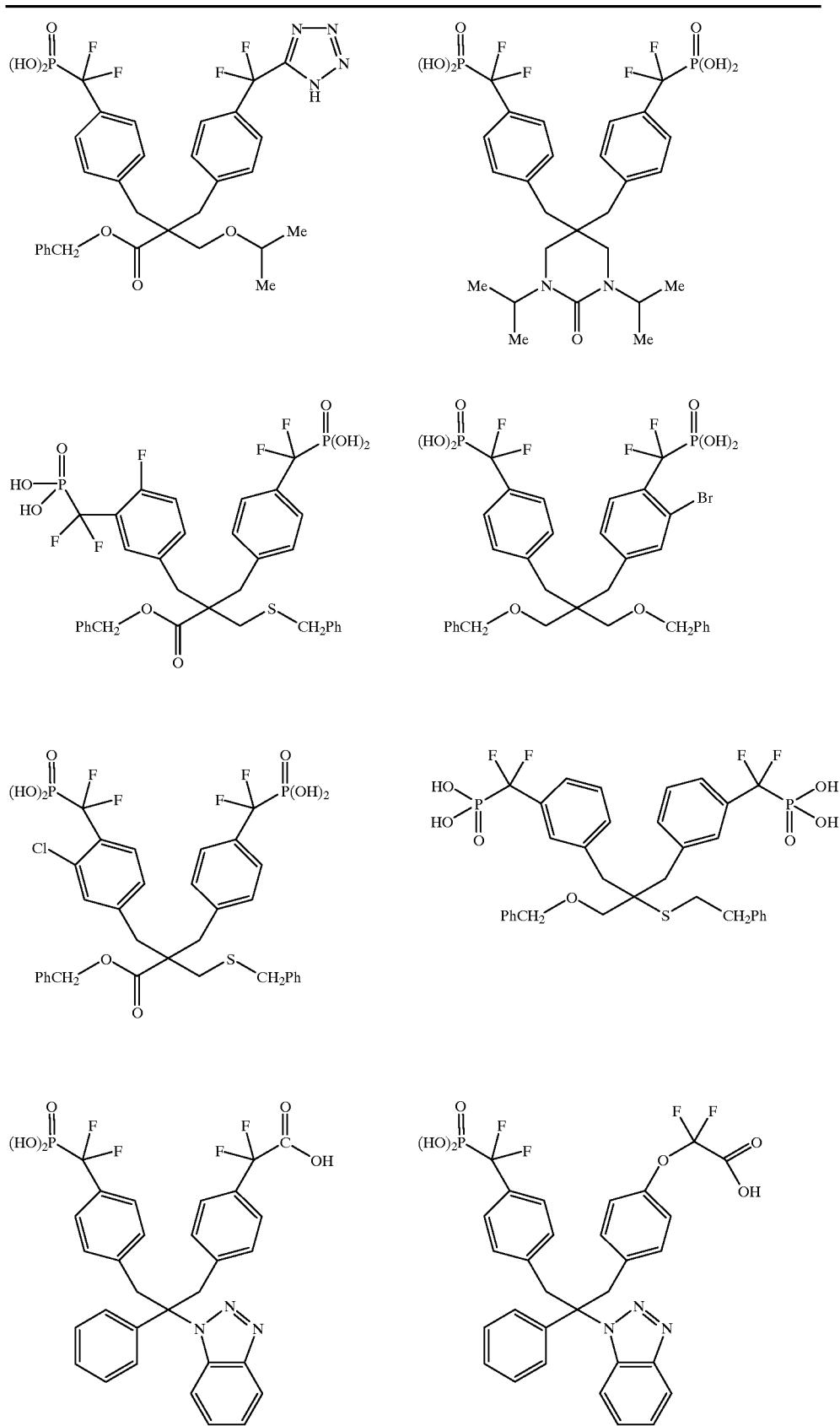

TABLE 2-continued
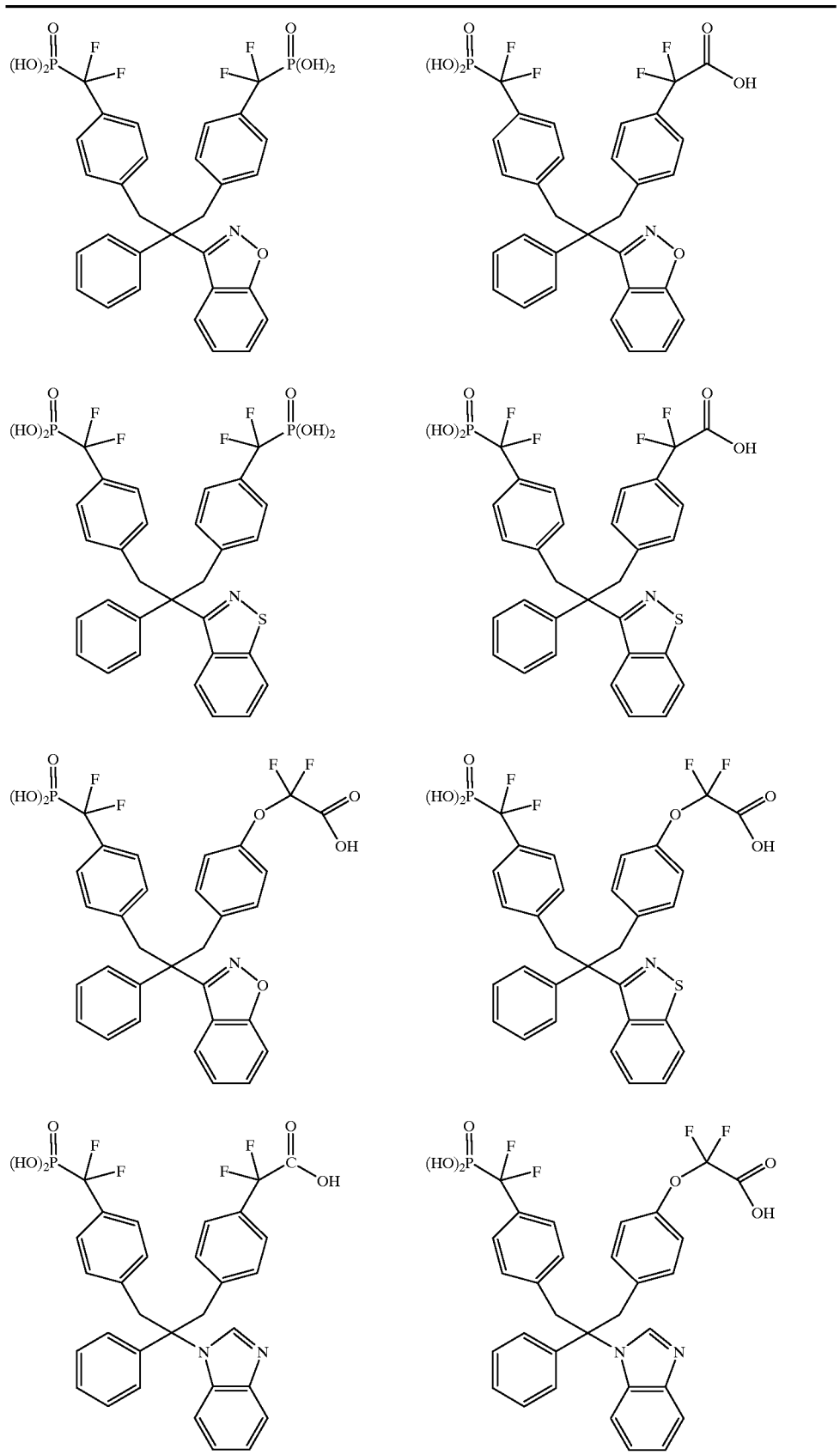

TABLE 2-continued
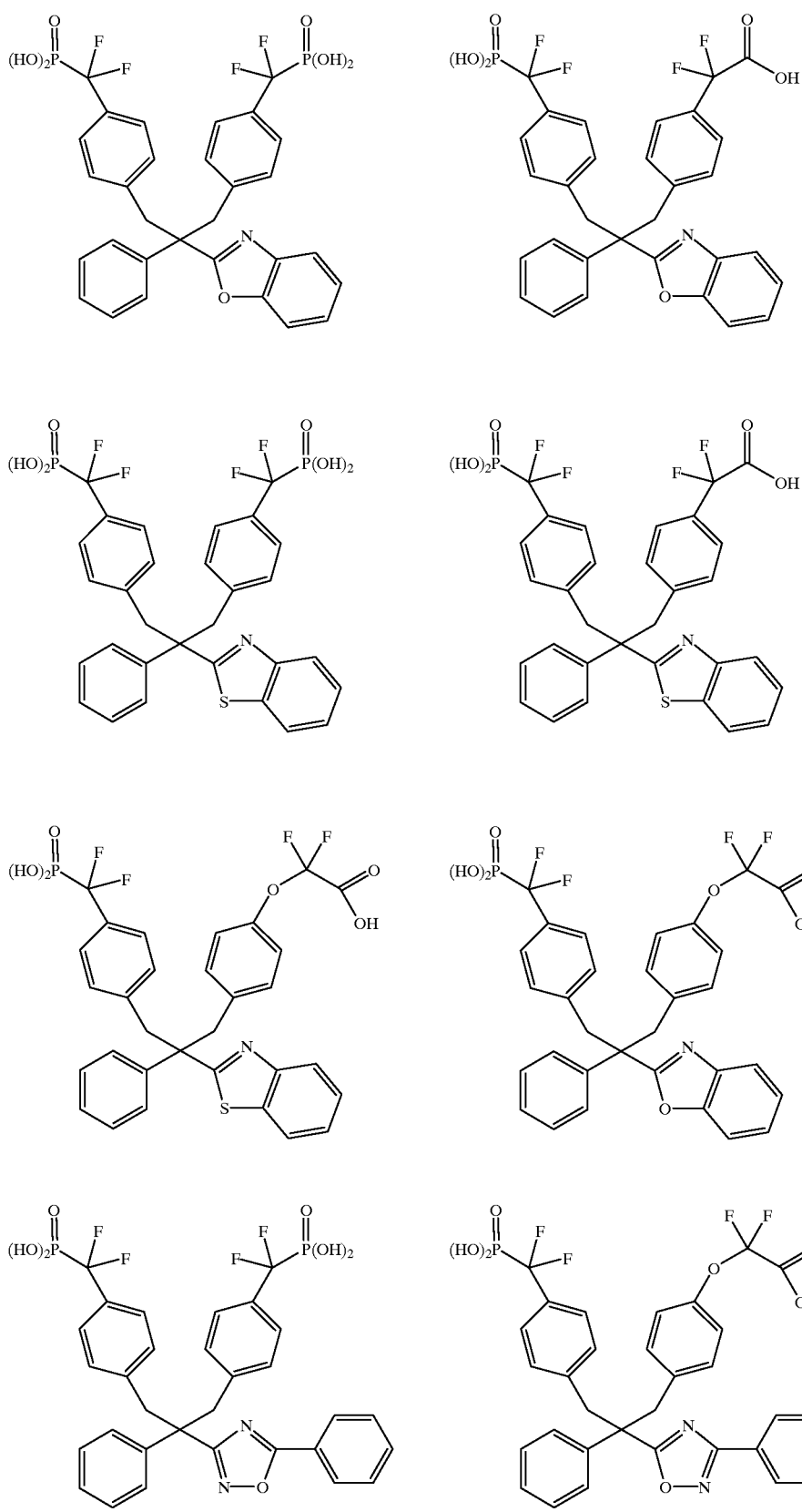

TABLE 2-continued

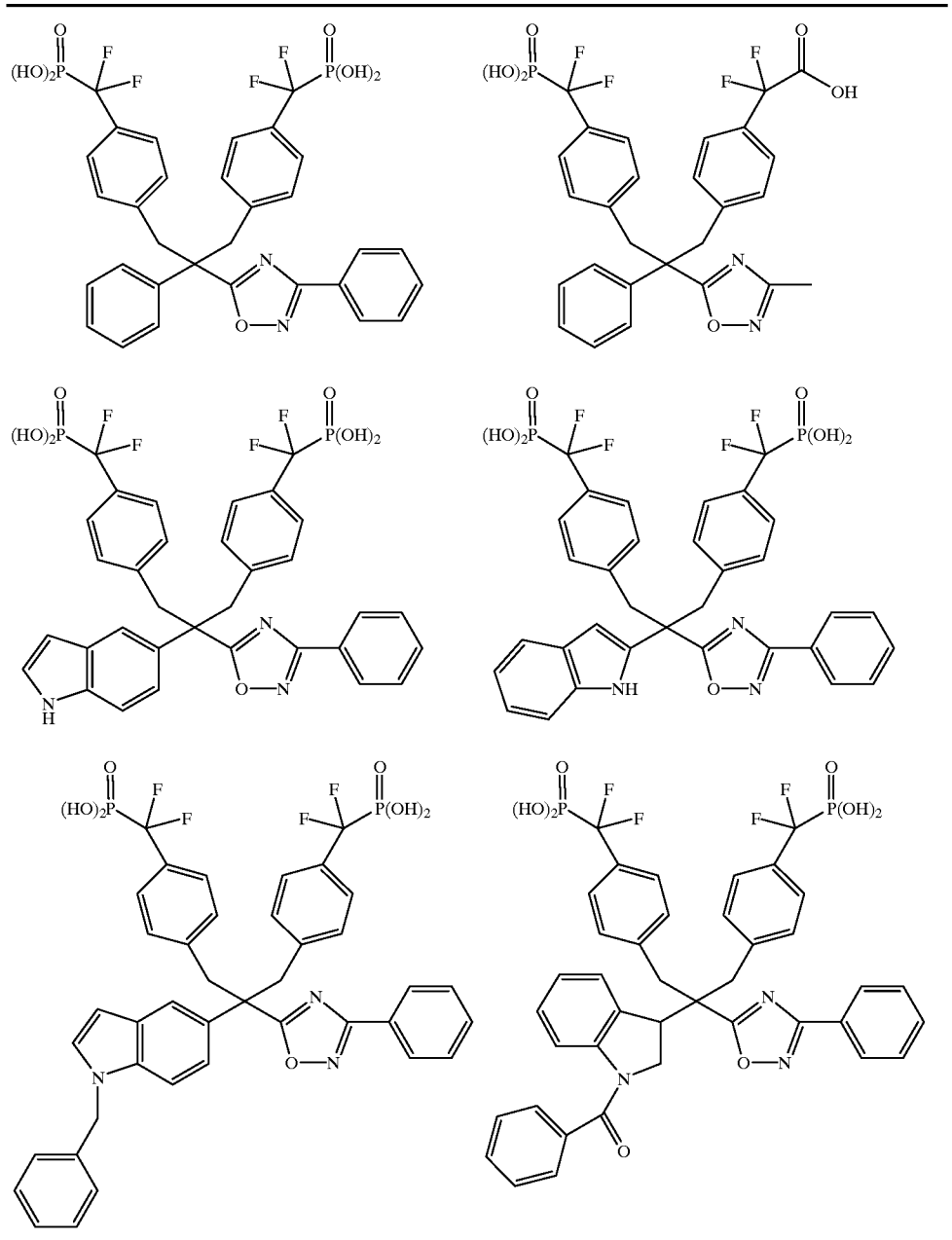

Assays for Demonstrating Biological Activity

Activity in the compounds of Formula I is demonstrated using the following assays for PTP-1B-inhibiting activity.

Phosphate Assay Protocol

Materials

EDTA—ethylenediaminetetraacetic acid (Sigma)

DMH—N,N'-dimethyl-N,N'-bis(mercaptoacetyl)-hydrazine (synthesis published in *J. Org. Chem.* 56, pp. 2332–2337, (1991) by R. Singh and G. M. Whitesides and can be substituted with DTT—dithiothreitol Bistris—2,2-bis(hydroxymethyl)2,2',2"-nitrilotriethanol—(Sigma) Triton X-100—octylphenolpoly(ethylene-glycolether) 10 (Pierce).

Antibody: Anti-glutathione S-transferase rabbit (H and L) fraction (Molecular Probes)

Enzyme: Human recombinant PTP-1B, containing amino acids 1–320, (Seq. ID No. 1) fused to GST enzyme (glutathione S-transferase) or to FLAG peptide purified by affinity chromatography (Huyer et al., 1997, J. Biol. Chem., 272, 843–852). Wild type (Seq. ID No. 1) contains active site cysteine(215), whereas mutant (Seq. ID No. 7) contains active site serine(215).

Tritiated peptide: Bz-NEJJ-CONH$_2$, Mwt. 808, empirical formula, $C_{32}H_{32}T_2O_{12}P_2F_4$.

Stock Solutions (10X) Assay Buffer 500 mM Bistris (Sigma), pH 6.2, MW=209.2

20 mM EDTA (GIBCO/BRL)
Store at 4° C.
Prepare Fresh Ddaily
Assay Buffer (1X) (room temp.) 2 mM EDTA
50 mM Bistris
5 mM DMH (MW=208)
Enzyme Dilution
Buffer (keep on ice)
50 mM Bistris
2 mM EDTA
5 mM DMH
20% Glycerol (Sigma)
0.01 mg/ml Triton X-100 (Pierce)
Antibody Dilution
Buffer (keep on ice)
50 mM Bistris
2 mM EDTA $IC_{50}$ Binding Assay Protocol Compounds (ligands) which potentially inhibit the binding of a radioactive ligand to the specific phosphatase are screened in a 96-well plate format as follows:

To each well is added the following solutions @ 25° C. in the following chronological order:

1. 110 µl of assay buffer.
2. 10 µl. of 50 nM tritiated BzN-EJJ-CONH$_2$ in assay buffer (1X) @ 25° C.
3. 10 µl. of testing compound in DMSO at 10 different concentrations in serial dilution (final DMSO, about 5% v/v) in duplicate @ 25° C.
4. 10 µl. of 3.75 µg/ml purified human recombinant GST-PTP-1B in enzyme dilution buffer.
5. The plate is shaken for 2 minutes.
6. 10 µl. of 0.3 µg/ml anti-glutathione S-transferase (anti-GST) rabbit IgG (Molecular Probes) diluted in antibody dilution buffer @ 25° C.
7. The plate is shaken for 2 minutes.
8. 50 µl. of protein A-PVT SPA beads (Amersham) @ 25° C.
9. The plate is shaken for 5 minutes. The binding signal is quantified on a Microbeta 96-well plate counter.
10. The non-specific signal is defined as the enzyme-ligand binding in the absence of anti-GST antibody.
11. 100% binding activity is defined as the enzyme-ligand binding in the presence of anti-GST antibody, but in the absence of the testing ligands with the non-specific binding subtracted.
12. Percentage of inhibition is calculated accordingly.
13. $IC_{50}$ value is approximated from the non-linear regression fit with the 4-parameter/multiple sites equation (described in: "Robust Statistics", New York, Wiley, by P. J. Huber (1981) and reported in nM units.
14. Test ligands (compounds) with larger than 90% inhibition at 10 µM are defined as actives.

Enzyme Assay PTP-1B

Assay buffer
50 mM Bis-Tris (pH=6.3)
2 mM EDTA
5 mM N,N'-dimethyl-N,N'-bis(mercaptoacetyl)hydrazine (DMH)

Substrate
10 mM fluorescein diphosphate (FDP) store at −20° C.
Enzyme dilution buffer
50 mM Bis-Tris (pH=6.3)
2 mM EDTA
5 mM DMH
20% (v/v) glycerol
0.01% Triton X-100

The assay was carried out at room temperature in 96 well plates. The reaction mixture in 170 µl contained 50 mM Bis-Tris (pH=6.3), 2 mM EDTA, 5 mM N,N'-dimethyl-N, N'bis(mercaptoacetyl)hydrazine (DMH) and 10 µM fluorescein diphosphare (FDP). 10 µl of 10 concentrations (serial dilution) of the test compound (inhibitor) dissolved in DMSO or DMSO alone for control was added to each well and the plate was mixed for 2 min. The reaction was initiated by adding 20 µl of diluted PTP-1B (50 nM in 50 mM Bis/Tris (pH=6.3), 2 mM EDTA, 5 mM DMH, 20% glycerol and 0.01% Triton X-100. The phosphatase activity was followed by monitoring the appearance of the fluorescent product fluorescein monophosphate (FMP) continuously for 15– 30 min, using the Cytofluor II plate reader (PerSeptive Biosystems Inc.) with excitation of 440 nm (slit width 20 nm) and emission at 530 nm (slit width 25 nm). All the assays were done at least in duplicate. The initial rate of FMP formation is plotted against the concentration of inhibitor and the data was fitted to 4-parameter equation and the inflection point of the fit is the $IC_{50}$.

PHARMACOKINETICS IN RATS

Per Os Pharmacokinetics in Rats

Procedure

The animals are housed, fed and cared for according to the Guidelines of the Canadian Council on Animal Care.

Male Sprague Dawley rats (325–375 g) are fasted overnight prior to each PO blood level study.

The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 1 mL of blood is collected into a heparinized vacutainer tube.

Compounds are prepared as required, in a standard dosing volume of 10 mL/kg, and administered orally by passing a 16 gauge, 3" gavaging needle into the stomach.

Subsequent bleeds are taken in the same manner as the zero bleed except that there is no need to nick the tail again. The tail is cleaned with a piece of gauze and milked/stroked as described above into the appropriately labelled tubes.

Immediately after sampling, blood is centrifuged, separated, put into clearly marked vials and stored in a freezer until analysed.

Typical time points for determination of rat blood levels after PO dosing are:

0, 15 min, 30 min, 1 h, 2 h, 4 h, 6 h

After the 4 hr time point bleed, food is provided to the rats ad libitum. Water is provided at all times during the study.

Vehicles

The following vehicles may be used in PO rat blood level determinations:

PEG 200/300/400: restricted to 2 mL/kg

Methocel 0.5%–1.0%: 10 mL/kg

Tween 80: 10 mL/kg

Compounds for PO blood levels can be in suspension form. For better dissolution, the solution can be placed in a sonicator for approximately 5 minutes.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(mg/kg)}{AUCiv}$$

The units of CL are mL/h•kg (milliliters per hour kilogram).

Intravenous Pharmacokinetics in Rats

Procedure

The animals are housed, fed and cared for according to the Guidelines of the Canadian Council on Animal Care.

Male Sprague Dawley (325–375 g) rats are placed in plastic shoe box cages with a suspended floor, cage top, water bottle and food.

The compound is prepared as required, in a standard dosing volume of 1 mL/kg.

Rats are bled for the zero blood sample and dosed under $CO_2$ sedation. The rats, one at a time, are placed in a primed $CO_2$ chamber and taken out as soon as they have lost their righting reflex. The rat is then placed on a restraining board, a nose cone with $CO_2$ delivery is placed over the muzzle and the rat restrained to the board with elastics. With the use of forceps and scissors, the jugular vein is exposed and the zero sample taken, followed by a measured dose of compound which is injected into the jugular vein. Light digital pressure is applied to the injection site, and the nose cone is removed. The time is noted. This constitutes the zero time point.

The 5 min bleed is taken by nicking a piece (1–2 mm) off the tip of the tail. The tail is then stroked with a firm but gentle motion from the top of the tail to the bottom to milk the blood out of the tail. Approximately 1 mL of blood is collected into a heparinized collection vial. Subsequent bleeds are taken in the same fashion, except that there is no need to nick the tail again. The tail is cleaned with a piece of gauze and bled, as described above, into the appropriate labelled tubes.

Typical time points for determination of rat blood levels after I.V. dosing are either:

0, 5 min, 15 min, 30 min, 1 h, 2 h, 6 h or 0, 5 min, 30 min, 1 h, 2 h, 4 h, 6 h.

Vehicles

The following vehicles may be used in IV rat blood level determinations:

Dextrose: 1 mL/kg

2-Hydroxypropyl-b-cyclodextrin 1 mL/kg

DMSO (dimethylsulfoxide): Restricted to a dose volume of 0.1 mL per animal

PEG 200: Not more than 60% mixed with 40% sterile water—1 mL/kg

With Dextrose, either sodium bicarbonate or sodium carbonate can be added if the solution is cloudy.

For analysis, aliquots are diluted with an equal volume of acetonitrile and centrifuged to remove protein precipitate. The supernatant is injected directly onto a C-18 HPLC column with UV detection. Quantitation is done relative to a clean blood sample spiked with a known quantity of drug. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

Clearance rates are calculated from the following relation:

$$CL = \frac{DOSEiv(mg/kg)}{AUCiv}$$

The units of CL are mL/h•kg (milliliters per hour kilogram).

The invention is further illustrated by the following non-limiting examples in which, unless stated otherwise:

(i) all operations were carried out at room or ambient temperature, that is, at a temperature in the range 18–25° C., (ii) evaporation of solvent was carried out using a rotary evaporator under reduced pressure (600–4000 pascals: 4.5–3.0 mm. Hg) with a bath temperature of up to 60° C., (iii) the course of reactions was followed by thin layer chromatography (TLC) and reaction times are given for illustration only;

(iv) melting points are uncorrected and 'd' indicates decomposition; the melting points given are those obtained for the materials prepared as described; polymorphism may result in isolation of materials with different melting points in some preparations;

(v) the structure and purity of all final products were assured by at least one of the following techniques: TLC, mass spectrometry, nuclear magnetic resonance (NMR) spectrometry or microanalytical data;

(vi) yields are given for illustration only;

(vii) when given, NMR data is in the form of delta (d) values for major diagnostic protons, given in parts per million (ppm) relative to tetramethylsilane (TMS) as internal standard, determined at 300 MHz or 400 MHz using the indicated solvent; conventional abbreviations used for signal shape are: s. singlet; d. doublet; t. triplet; m. multiplet; br. broad; etc.: in addition "Ar" signifies an aromatic signal;

(viii) chemical symbols have their usual meanings; the following abbreviations have also been used v (volume), w (weight), b.p. (boiling point), m.p. (melting point), L (liter (s)), mL (milliliters), g (gram(s)), mg (milligrams(s)), mol (moles), mmol (millimoles), eq (equivalent(s)).

EXAMPLE 1

2,2-di{4-[difluoro(phosphono)methyl] benzyl}malonic Acid, Benzyl Methyl Ester

Step 1 Di(tert-butyl) hydroxy(4-methylphenyl) methylphosphonate

To a solution of di-tert-butylphosphite (30 g) in THF (700 mL) cooled at −78° C. was added dropwise a solution of LiN(TMS)$_2$ (165 mL, 1M in THF). After stirring for 30 min at −78° C., a solution of 4-tolualdehyde (18 mL in 100 mL of THF) was added. The reaction mixture was stirred for 30 min at −78° C. and 2 h at 0° C., and then quenched with 400 mL of 50% saturated aqueous NH₄Cl solution. The mixture was extracted with 1 L of 2:1 hexane/EtOAc and the extract was dried over Na₂SO₄. After concentration and swishing from hexane, 32 g of the title compound was obtained as a white solid.

¹H NMR (300 MHz, acetone-d₆) δ 7.36 (2H, dd), 7.12 (2H, d), 4.55–4.75 (2H, m), 2.29 (3H, s), 1.40 (9H, s), 1.34 (9H, s).

Step 2 Di(tert-butyl) (4-methylbenzoyl)phosphonate

To a solution of oxalyl chloride (1.75 mL) in CH₂Cl₂ (60 mL) cooled at −78° C. was added DMSO (2.8 mL) dropwise. The mixture was stirred for 10 min at −78° C. and a solution of di(tert-butyl) hydroxy(4-methylphenyl) methylphosphonate (3.14 g in 20 mL of CH₂Cl₂ was introduced dropwise. After stirring for 30 min at −78° C., 14 mL of Et₃N was added. The resulting mixture was stirred for 30 min at −78° C. and 45 min at room temperature, and then quenched with 200 mL of 50% saturated aqueous NaCl solution. The mixture was extracted with 2×200 mL of 1:1 hexane/EtOAc and the extract was dried over MgSO₄ and concentrated to give 3 g of the title compound as a yellow oil.

¹H NMR (300 MHz, acetone-d₆) δ 8.18 (2H, d), 7.37 (2H, d), 2.41 (3H, s), 1.53 (18H, s).

Step 3 Di(tert-butyl) [4-(bromomethyl)benzoyl] phosphonate

A mixture of di(tert-butyl) (4-methylbenzoyl) phosphonate (10 g), NBS (8.3 g), NaHCO₃ (10 g) and benzoyl peroxide (0.1 g) in 200 mL of CCl₄ was heated to reflux for 20 min. The mixture was cooled to room temperature, diluted with 200 mL of 10:1 hexane/EtOAc and filtered through a pad of silca gel. The filtrate was concentrated and the residue was swished from hexane to give 2.8 g of the title compound as a beige solid.

¹H NMR (300 MHz, acetone-d₆) δ 8.28 (2H, d), 7.66 (2H, d), 4.73 (2H, s), 1.50 (18H, s).

Step 4 Di(tert-butyl) [[4-(bromomethyl)phenyl](difluoro) methyl]phosphonate

Diethylaminosulphur trifluoride (9 mL) and di(tert-butyl) [4-(bromomethyl)benzoyl]phosphonate (2.8 g) were mixed at −78° C. The mixture was allowed to warm slowly to room temperature over a period of 30 min and stirred at room temperature for 14 h. The reaction mixture was then poured into a mixture 300 mL of 4:1 hexane/EtOAc, 300 mL of saturated NaHCO₃ and 10 mL of i-Pr₂NEt at 0° C. with vigorous stirring. The organic layer was separated, dried over Na₂SO₄, and concentrated to give 2.4 g of the title compound as a red oil.

¹H NMR (300 MHz, acetone-d₆) δ 7.58 (4H, s), 4.70 (2H, s), 1.43 (18H, s).

Step 5 2,2-Di{4-[(di-tert-butoxyphosphoryl)(difluoro) methyl]benzyl}malonic Acid, Benzyl Methyl Ester To a solution of benzyl methyl malonate (0.2 g) in DMF (8 mL), was added sequentially NaH (0.08 g, 60% in mineral oil), di(tert-butyl) [[4-(bromomethyl)phenyl](difluoro) methyl]phosphonate (0.83 g), and n-Bu₄NI (0.08 g). The reaction mixture was stirred at room temperature for 2.5 h, then quenched with 20 mL of saturated aqueous NH₄Cl solution and extracted with 50 mL of 1:1 hexane/EtOAc. The extract was dried over Na₂SO₄ and concentrated. The residue was purified by silica gel chromatography eluted with 2:1 hexane/EtOAc. First eluted was 1-benzyl 3-methyl 2-{4-[(di-tert-butoxyphosphoryl)(difluoro)methyl] benzyl}malonate (0.2 g), followed by the title compound (0.3 g) as an oil.

¹H NMR (400 MHz, acetone-d₆) δ 7.51 (4H, d), 7.3–7.42 (9H, m), 5.14 (2H, s), 3.62 (3H, s), 3.27 (4H, s), 1.44 (36H, s).

Step 6 2,2-Di{4-[difluoro(phosphono)methyl] benzyl}malonic Acid, Benzyl Methyl Ester A solution of 2,2-di{4-[difluoro(phosphono)methyl] benzyl}malonic acid, benzyl methyl ester (50 mg) in 5 mL of 10:1 TFA/water was stirred for 2 h and then concentrated. The residue was dissolved in 5 mL of water and washed with 2×5 mL of ether and the aqueous solution was lyopholized to give 15 mg of the title compound as a beige solid.

¹H NMR (400 MHz, methanol-d₄) δ 7.22 (4H, d), 7.02–7.12 (3H, m), 6.92–7.00 (6H, m), 4.80 (2H, s), 3.28 (3H, s), 2.96 (4H, s).

EXAMPLE 2

2,2-di{4-[difluoro(phosphono)methyl] benzyl}malonic Acid, Dibenzyl Ester

Step 1 Dibenzyl 2,2-di{4-[(di-tert-butoxyphosphoryl) (difluoro)methyl]benzyl}malonate To a solution of dibenzyl malonate (0.5 g) in DMF (4 mL), was added sequentially NaH (0.12 g, 80% in mineral oil), di(tert-butyl) [[4-(bromomethyl)phenyl](difluoro) methyl]phosphonate (1.60 g). The reaction mixture was stirred at room temperature for 1 h, then quenched with 20 mL of saturated aqueous NH₄Cl solution and extracted with 50 mL EtOAc. The extract was dried over Na₂SO₄ and concentrated. The residue was purified by silica gel chromatography eluted with 1:1 hexane/EtOAc to give the title compound (0.3 g).

Step 2 2,2-Di{4-[difluoro(phosphono)methyl] benzyl}malonic acid, dibenzyl ester

A solution of dibenzyl 2,2-di{4-[(di-tert-butoxyphosphoryl) (difluoro)methyl]benzyl}malonate (100 mg) in 2 mL of 10:1 TFA/water was stirred for 0.5 h and then concentrated. The residue was dissolved in 5 mL of water and lyopholized to give 100 mg of the title compound as a beige solid.

¹H NMR (300 MHz, acetone-d₆) δ7.10–7.50 (18H, m), 5.05 (4H, s), 3.20 (4H, s).

EXAMPLE 3

2,2-Di{4-[Difluoro(Phosphono)Methyl] Benzyl}Malonic Acid, Diisopropyl Ester

¹H NMR (500 MHz, acetone-d₆) δ1.15 (12H, d), 3.22 (4H, s), 4.45 (2H, m), 7.32 (4H, d), 7.52 (4H, d).

EXAMPLE 4

2,2-Di{4-[Difluoro(Phosphono)Methyl]Benzyl}-3-Methoxy-3-Oxopropanoic Acid

Step 1 2,2-Di{4-[(di-tert-butoxyphosphoryl)(difluoro) methyl]benzyl}-3-methoxy-3-oxopropanoic acid A mixture of 2,2-di{4-[(di-tert-butoxyphosphoryl) (difluoro)methyl]benzyl}malonic acid, benzyl methyl ester (0.2 g) and Pd/C (0.1 g, 10%) in 30 mL of MeOH was shaken under 50 psi of H₂ for 3 h. The mixture was filtered and the filtrate was concentrated. The residue was purified by silica gel chromatography eluted with 3:2:0.1 EtOAc/ hexane/AcOH to give 0.1 g of the title compound as a yellow syrup.

¹H NMR (400 MHz, acetone-d₆) δ7.52 (4H, d),7.38 (4H, d), 3.68 (3H, s), 3.30 (2H, d), 3.24 (2H, d), 1.45 (36H, s).

Step 2 2,2-Di{4-[difluoro(phosphono)methyl]benzyl}-3-methoxy-3-oxopropanoic acid A solution of 2,2-di{4-[(di-tert-butoxyphosphoryl) (difluoro)methyl]benzyl}-3-methoxy-3-oxopropanoic acid (80 mg) in 5 mL of 10:1 TFA/water was stirred for 1 h and then concentrated. The residue was dissolved in 4 mL of water and washed with 2×5 mL of ether and the aqueous solution was lyopholized to give 20 mg of the title compound as a white solid.

$^1$H NMR (400 MHz, methanol-$d_4$) δ7.53 (4H, d), 7.33 (4H, d), 3.64 (3H, s), 3.25 (2H, d), 3.20 (2H, d).

EXAMPLE 5

3-(Benzylamino)-2,2-Di{4-[Difluoro(Phosphono) Methyl]Benzyl}-3-Oxopropanoic Acid, Methyl Ester Step 1 Methyl 3-(benzylamino)-2,2-di{4-[(di-tert-butoxyphosphoryl) (difluoro)methyl]benzyl}-3-oxopropanoate A mixture of 2,2-di{4-[difluoro(phosphono)methyl] benzyl}-3-methoxy-3-oxopropanoic acid (0.1 g), I-Pr$_2$NEt (0.2 mL) benzylamine (0.1 mL), and HATU (0.2 g) in DMF(3 mL) was stirred for 1.5 h at room temperature. The mixture was then poured into 10 ml of brine and extracted with 50 mL of 1:1 hexane/EtOAc. The extract was dried over Na$_2$SO$_2$ and concentrated. The residue was purified by silica gel chromatography eluted with 1:1 EtOAc/hexane to give 15 mg of the title compound as a yellow syrup.

$^1$H NMR (400 MHz, acetone-$d_6$) δ7.45 (4H, d), 7.22–7.35 (3H, m), 7.22 (4H, d), 4.34 (2H, d), 3.76 (3H, s), 3.60 (2H, d), 3.40 (2H, d), 1.43 (18H, s), 1.40 (18H, s).

Step 2 3-(Benzylamino)-2,2-di{4-[difluoro(phosphono) methyl]benzyl}-3-oxopropanoic acid, methyl ester A solution of methyl 3-(benzylamino)-2,2-di{4-[(di-tert-butoxyphosphoryl)(difluoro)methyl]benzyl}-3-oxopropanoate (15 mg) in 2 mL of CH$_2$Cl$_2$ and 1.5 mL of TFA was stirred for 2 h and then concentrated. The residue was dissolved in 3 mL of water and washed with 3×2 mL of ether and the aqueous solution was lyopholized to give 13 mg of the title compound as a white solid.

$^1$H NMR (400 MHz, methanol-$d_4$) δ7.47 (4H, d), 7.10–7.20 (3H, m), 7.15 (4H, s), 7.02 (2H, d), 4.30 (2H, d), 3.75 (3H, s), 3.48 (2H, d), 3.30 (2H, d).

EXAMPLE 6

2,2-Di{4-[Difluoro(Phosphono)Methyl] Benzyl}Malonic Acid

A mixture of the product of Example 2 (0.2 g), PdCl$_2$ and a few drops of HCO$_2$H in 20 mL of MeOH was shaken under 50 psi of H$_2$ for 24 h. The reaction mixture was filtered through celite and the filtrate was concentrated. The residue was lyopholized to give 0.1 g of the title compound.

$^1$H NMR (300 MHz, methanol-$d_4$) δ7.25–7.60 (8H, m), 3.15 (4H, s).

EXAMPLE 7

2-{4-[3-(Benzyloxy)-2-{4-[Difluoro(Phosphono) Methyl]Benzyl}-2-(Methoxycarbonyl)-3-Oxopropyl] Phenyl}-2,2-Difluoroacetic Acid To starting 1-benzyl 3-methyl 2-{4-[(di-tert-butoxyphosphoryl) (difluoro)methyl]benzyl}malonate (0.12 g) in DMF(5.0 mL) was added NaH (55 mg). The reaction was stirred at r.t. for 30 min. Then tert-butyl 2-[4-(bromomethyl)phenyl]-2,2-difluoroacetate(0.085 g, prepared according the procedures described by J. W. Tilley et al, *J. Med. Chem.* 1991, 34. 1125) was added to the mixture. After stirring for 2 h, the mixture was quenched with H$_2$O and extracted with EtOAc (50 mL). The extract was dried over Na$_2$SO$_4$ and evaporated to dryness. The residue was treated with a solution of TFA/H$_2$O (3 mL, 9:1) for 3 h at r.t. and evaporated to dryness. The crude was purified on reverse phase HPLC to give 12 mg of the title compound.

$^1$H NMR (400 MHz, CD$_3$OD), δ3.25 (2H, m), 3.52 (3H, s), 5.05 (2H, m), 7.25 (5H, m), 7.35 (4H, m), 7.50 (4H, m).

EXAMPLE 8

2-{4-[Difluoro(Phosphono)Methyl]Benzyl}-2-[4-(Phosphonomethyl)Benzyl]Malonic Acid, Dibenzyl Ester Step 1 Dibenzyl 2-{4-[(di-tert-butoxyphosphoryl)methyl] benzyl}malonate To a solution of dibenzyl malonate (0.5 g) in DMF (8 mL), was added sequentially NaH (0.06 g, 80% in mineral oil), di(tert-butyl) [4-(bromomethyl)benzyl]phosphonate (0.66 g). The reaction mixture was stirred at room temperature for 1 h, then quenched with 20 mL of saturated aqueous NH$_4$OAc solution and extracted with 50 mL EtOAc. The extract was dried over Na$_2$SO$_4$ and concentrated. The sesidue was purified by silica gel chromatography eluted with to give the title compound (0.2 g).

Step 2 Dibenzyl 2-{4-[(di-tert-butoxyphosphoryl)(difluoro) methyl]benzyl}-2-{4-[(di-tert-butoxyphosphoryl)methyl] benzyl}malonate The title compound was obtained by using the product of Step 1 and di(tert-butyl) [[4-(bromomethyl)phenyl] (difluoro)methyl]phosphonate under the same conditions as described in Step 1.

Step 3 2-{4-[Difluoro(phosphono)methyl]benzyl}-2-[4-(phosphonomethyl) benzyl]malonic acid, dibenzyl ester The title compound was obtained by using the same procedures as described in Step 2 of Example 2.

$^1$H NMR (300 MHz, acetone-$d_6$) δ7.00–7.50 (18H, m), 5.10 (4H, s), 3.15 (4H, s), 2.80 (2H, d).

EXAMPLE 9

2-(4-Carboxybenzyl)-2-{4-[Difluoro(phosphono) Methyl]Benzyl}Malonic Acid, Dibenzyl Ester To a solution of dibenzylmalonate (0.55 g) in DMF (16 mL) was added NaH. (0.11 g) 2 eq. The reaction was stirred at r.t. for 30 min. Then p-bromomethyl benzoic acid (0.416 g) was added to the mixture. After stirring for 2 h, the second portion of NaH (55 mg) was added and the mixture was stirred for 30 min, di(tert-butyl) [[4-(bromomethyl)phenyl] (difluoro)methyl]phosphonate (0.8 g) was then added. The reaction mixture was stirred overnight at r.t. and quenched with H$_2$O, AcOH and extracted with EtOAc. The extract was dried and evaporated, and the residue was treated with TFA/H$_2$O 9:1 for 1 h, then evaporated and purified by reverse phase HPLC to give 15 mg of the title compound.

$^1$H NMR (400 MHz, CD$_3$OD) δ: 3.28 (2H, m), 5.10 (4H, s), 5.40 (2H, s), 7.18 (4H, m), 7.22 (8H, m), 7.55 (2H, d), 7.65 (2H, d), 7.75 (2H, d).

EXAMPLE 10

2-Benzyl-2-{4-[Difluoro(Phosphono)Methyl] Benzyl}Malonic Acid, Dibenzyl Ester $^1$H NMR (300 MHz, acetone-$d_6$) δ7.15–7.55 (19H, m), 5.05 (4H, s), 3.20 (4H, 2s).

EXAMPLE 11

2,2-Di{4-[Difluoro(Phosphono)Methyl]Benzyl}-1,3-Propanediol, Dibenzyl Ether

Step 1 Dimethyl 2,2-di[4-(diethoxymethyl)benzyl]malonate

A solution of dimethyl malonate (0.66 g), 1-(bromomethyl)-4-(diethoxymethyl)benzene (2.73 g) in DMF (30 mL) was treated with NaH (0.4 g, 60% in mineral oil). The mixture was stirred for 3 h at room temperature and 1 h at 50° C., and then quenched with 100 mL of saturated $NH_4Cl$. The product was extracted with 200 mL of 1:1 hexane/EtOAc. The extract was dried over $Na_2SO_4$ and concentrated to give the title compound (3 g) which was used without further purification.

Step 2 2,2-Di[4-(diethoxymethyl)benzyl]-1,3-propanediol

To a solution of dimethyl 2,2-di[4-(diethoxymethyl) benzyl]malonate (3 g, crude) in 200 mL of THF coole at 0° C. was added of $LiAlH_4$ (0.7 g). The mixture was stirred for 0.5 h at room temperature and the quenched with acetone (5 mL), followed by 100 mL of 20% aqeous sodium potassium tartrate solution. The mixture was extracted with 2×200 mL of EtOAc. The extract was dried over $Na_2SO_4$ and concentrated to give the crude title compound which was used for next step without further purification.

Step 3 2,2-Di(4-formylbenzyl)-1,3-propanediol, dibenzyl ether

A mixture of 2,2-di[4-(diethoxymethyl)benzyl]-1,3-propanediol (2 g, crude), benzyl bromide (1.2 mL), and NaH (0.6 g, 60% in mineral oil) was stirred for 2 days at 40° C. The mixture was then quenched with 50 mL of saturated $NH_4Cl$ and extracted with 100 mL of 1:1 hexane/EtOAc. The extract was dried over $Na_2SO_4$ and concentrated. The residue was dissolved in 200 mL of acetone and treated with 200 mg of p-TsOH. After stirring for 1 h, 1 mL of $Et_3N$ was added and the reaction mixture was concentrated. The residue was purified by silics gel chromatography eluted with 5:1 hexane/EtOAc to give 2.4 g of the title compound.

$^1$H NMR (400 MHz, acetone-$d_6$) δ10.00 (2H, s), 7.79 (4H, d), 7.28–7.50 (14H, m), 4.53 (4H, s), 2.99 (4H, s), 2.97 (4H, s).

Step 4 2,2-Di{4-[(di-tert-butoxyphosphoryl)carbonyl] benzyl}-1,3-propanediol, dibenzyl ether To a solution of di-tert-butylphosphite (2.4 g) in THF (60 mL) cooled at −78° C. was added dropwise a solution of $LiN(TMS)_2$ (12.5 mL, 1M in THF). After stirring for 30 min at −78° C., a solution of 2,2-di(4-formylbenzyl)-1,3-propanediol, dibenzyl ether (1.2 g in 6 mL of THF) was added. The reaction mixture was stirred for 10 min at −78° C. and 20 min at 0° C., and then quenched with 50 mL of 50% saturated aqueous $NH_4Cl$ solution. The mixture was extracted with 2×70 mL of EtOAc and the extract was dried over $Na_2SO_4$. After concentration, the crude product was oxidized under the same conditions as described in Step 2 of Example 1 to give the title compound, which was purified by silica gel chromatography eluted with 2:1 hexane/EtOAc.

Step 5 2,2-Di{4-[(di-tert-butoxyphosphoryl)(difluoro) methyl]benzyl}-1,3-propanediol, dibenzyl ether Diethylamonosulphur trfluoride (5.5 mL) and the product from Step 4 (1.0 g) were mixed at −78° C. The mixture was allowed to warm slowly to room temperature over a period of 30 min and stirred at room temperature for 3 days. The reaction mixture was then poured into a mixture 200 mL of EtOAc, 200 mL of saturated $NaHCO_3$ and 20 mL of $Et_3N$ at 0° C. with vigorous stirring. The organic layer was separated, dried over $Na_2SO_4$, and concentrated. The residue was purified by silica gel chromatography eluted with 2:1 hexane/EtOAc to give 0.25 g of the title compound as a yellow oil.

Step 6 2,2-Di{4-[difluoro(phosphono)methyl]benzyl}-1,3-propane-diol, dibenzyl ether A mixture of the product from Step 5 (0.25 g) in 3 mL of $CH_2Cl_2$ and 2 mL of TFA was stirred for 1 h at room temperature and then concentrated. The residue was dissolved in 20 mL water and washed with 2×10 mL of 1:1 hexane/ether. The aqueous layer was lyopholized to give 0.13 g of the title compound as a yellow solid.

$^1$H NMR (400 MHz, methanol-$d_4$) d 8.10–8.24 (14H, m), 7.99 (4H, d), 5.25 (4H, s), 3.72 (4H, s), 3.57 (4H, s).

EXAMPLE 12

2,2-Di{4-[Difluoro(Phosphono)Methyl]Benzyl}-1,3-Propane-Diol

A mixture of the product of Step 6 of Example 11 (35 mg) and $PdCl_2$ (10 mg) in 20 mL of MeOH was shaken under 50 psi of hydrogen for 16 h. The mixture was then filtered through a pad of celite and the filtrate was concentrated to give 30 mg of the title compound.

EXAMPLE 13

2-{4-[Difluoro(Phosphono)Methyl]Benzyl}-2-[4-(Methylsulfonyl)Benzyl]Malonic Acid, Dibenzyl Ester $^1$H NMR (300 MHz, acetone-$d_6$) δ7.15–7.95 (18H, m), 5.10 (4H, s), 3.20 (2H, s), 3.30 (2H, s), 3.05 (3H, s).

EXAMPLE 14

2-{4-[Difluoro(Phosphono)Methyl]Benzyl}-2-{4-[(Methylsulfonyl)Methyl]Benzyl}Malonic Acid, Dibenzyl Ester $^1$H NMR (400 MHz, acetone-$d_6$) δ7.53 (2H. d), 7.20–7.40 (16H, m), 5.05 (4H, s), 4.35 (2H, s), 3.28 (2H, s), 3.25 (2H, s), 2.29 (3H, s).

EXAMPLE 15

2-{4-[Difluoro(Phosphono)Methyl]Benzyl}-2-{4-[(Ethylsulfonyl)Methyl]Benzyl}Malonic Acid, Dibenzyl Ester $^1$H NMR (400 MHz, acetone-$d_6$) δ7.52 (2H, d), 7.20–7.40 (16H, m), 5.05 (4H, s), 4.34 (2H, s), 3.28 (2H, s), 3.25 (2H, s), 2.94 (2H, q), 1.27 (3H, t).

EXAMPLE 16

(4-[2-(4-(Aminosulfonyl)Benzyl)-3-(Benzyloxy)-2-(Benzyloxycarbonyl)-3-Oxopropyl]Phenyl) (Difluoro)Methylphosphonic Acid Step 1 Dibenzyl 2-[4-(methylsulfanyl)benzyl]malonate To a solution of I (3.0 g, 10.6 mmol) in DMF (30 mL) at 0° C. was added NaH (0.317 g, 80% in oil). After 1 h, 4-methylthiobenzyl chloride (1.39 mL, 9.5 mmol) was added dropwise. The mixture was stirred for 15 min at 0° C., followed by 2 h at r.t. Saturated $NH_4Cl$ solution (100 mL) was then added, and the product was extracted with $Et_2O$. The organic layer was washed with $H_2O$ and brine, and was then dried ($MgSO_4$), filtered, and evaporated. The residue was purified by flash chromatography (1:10 EtOAc: hexane) to give a colorless oil (3.9 g).

Step 2 Dibenzyl 2-[4-(methylsulfinyl)benzyl)malonate

Prepared in the same manner as Example 30, Step 5.

Step 3 Dibenzyl 2-[4-(aminosulfonyl)benzyl]malonate

A solution of the sulfoxide from Step 2 (1.0 g, 2.4 mmol) in trifluoroacetic anhydride (10 mL) was brought to reflux for 20 min. The solvent was removed under vacuum and the residue was co-evaporated twice with toluene. $CH_2Cl_2/H_2O$ (1:1) (20 mL) was added, and $N_2$ was bubbled into the solution at 0° C. for 30 min. HOAc (10 mL) was then added and $Cl_2$ was bubbled into the solution for 15 min. The mixture was stirred at r.t. for 30 min., at which point the solvent was removed under vacuum and the residue was dissolved in THF. After cooling to 0° C., concentrated $NH_4OH$ was added. Following a standard aqueous/EtOAc work up, the crude was purified by flash chromatography to give a syrup (0.53 g).

Step 4 Dibenzyl 2-[4-(aminosulfonyl)benzyl)-2-{4-[[tert-butoxy (hydroxy)phosphoryl](difluoro)methyl]benzyl}malonate To a solution of the sulfonamide from Step 3 (0.53 g, 1.17 mmol) in DMF (5 mL) at 0° C. was added NaH (39 mg, 80% in oil). After 20 min. at 0° C., a solution of di(tert-butyl)[4-(bromomethyl)phenyl](difluoro)methylphosphonate (0.53 g, 1.3 mmol) in DMF (3 mL) was added via syringe. After 1 h at 0° C., saturated $NH_4Cl$ solution (10 mL) was added and the product was extracted with $Et_2O$. The organic layer was washed with $H_2O$ and brine, and was then dried ($MgSO_4$), filtered, and evaporated. The residue was purified by flash chromatography (1:1 EtOAc/hexane, followed by EtOAc, followed by MeOH) to give a pale brown syrup (0.46 g).

Step 5 (4-{2-[4-(aminosulfonyl)benzyl}-3-(benzyloxy)-2-[((benzyloxy)carbonyl]-3-oxopropyl}phenyl)(difluoro)methylphosphonic acid The product from Step 4 (225 mg) was dissolved in HOAc (3 mL) and $H_2O$ (0.5 mL). After stirring for 48 h at r.t., the solvent was removed under vacuum and the residue was co-evaporated twice with toluene and once with acetone. A tan colored gum (200 mg) was obtained.

$^1$H NMR (300 MHz, dmso $d_6$) δ3.14–3.22 (m, 4H), 5.00–5.07 (m, 4H), 7.09–7.14 (m, 2H), 7.14–7.23 (m, 4H), 7.25–7.37 (m, 8H), 7.44–7.51 (m, 2H), 7.68–7.74 (m, 2H).

EXAMPLE 17

2-[4-(3-(Benzyloxy)-2-[(Benzyloxy)Carbonyl]-2-{4-[Difluoro (Phosphono)Methyl]Benzyl}-3-Oxopropyl)Phenyl]-2,2-Difluoroacetic Acid

Step 1

The title compound was prepared as described for example 7.

$^1$H NMR: (400 MHz, acetone-$d_6$) δ7.50 (4H, d), 7.35–7.10 (14H, m), 5.05 (4H, s), 3.30 (4H, s), 2.60 (6H, s).

EXAMPLE 18

(4-(2-[4-(Aminocarbonyl)Benzyl]-3-(Benzyloxy)-2-[(Benzyloxycarbonyl]-3-Oxopropyl}Phenyl)(Difluoro)Methylphosphonic Acid

Step 1 Dibenzyl 2-{4-[[di(tert-butoxy)phosphoryl](difluoro)methyl) benzyl}malonate To a solution of dibenzyl malonate (0.689 g, 2.42 mmol) in DMF (12 mL) at 0° C. were added NaH in oil (0.053 g, 1.32 mmol), di(tert-butyl)[[4-bromomethyl]phenyl](difluoro)methyl phosphonate (0.500 g, 1.21 mmol) and $nBu_4NI$. After TLC showed completion (room temperature) the reaction was quenched with $NH_4OAc$. After usual workup and purification by flash chromatography 430 mg, of the title compound was obtained.

Step 2 Dibenzyl 2-[4-(aminocarbonyl)benzyl]-2-{4-[[di(tert-butoxy)phosphoryl](difluoro)methyl]benzyl}malonate To compound of Step 1 (0.050 g, 0.081 mmol) in DMF (1.0 mL) were added at 0° C. NaH (0.004 g, 0.100 mmol) and 4-bromothyl benzamide (0.02 g, 0.100 mmol). After a period of 1 h at r.t., the reaction mixture was poured over $H_2O$ and ethyl acetate. The organic phase was separated, dried over $Na_2SO_4$, filtered and evaporated. The title compound was purified by flash chromatography.

Step 3 (4-(2-[4-(aminocarbonyl)benzyl]-3-(benzyloxy)-2-[(benzyloxycarbonyl]-3-oxopropylphenyl)(difluoro) methylphosphoric acid The compound of Step 2 was treated with TFA-$H_2O$ as described for Example 23 Step 5.

$^1$H NMR (400 MHz, $CD_3COCD_3$) δ3.20 (4H, 2s), 5.05 (4H, s), 7.20–7.85 (18H, m).

EXAMPLE 19

{4-[2-{4-[Difluoro(Phosphono)Methyl]Benzyl}-3-Isopropoxy-2-(Isopropoxymethyl)Propyl]Phenyl} (Difluoro)Methyl Phosphonic Acid

Step 1 2,2-bis(4-bromobenzyl)-1,3-propanediol

To dimethyl malonate (6.60 g, 50 mmol) in DMF (100 mL) was added NaH (2.00 g, 50 mmol) and 4-bromomethyl bromobenzene (25 g, 100 mmol). After a period of 6 h at room temperature, 200 mL of saturated $NH_4Cl$ and 200 mL of $H_2O$ were added. The crude product was extracted with a mixture of toluene and ether, dried over $Na_2SO_4$, filtered and evaporated. To the oil dissolved in THF (300 mL) at 0° C. LAH (4.5 g) was added. After a period of 2 h at room temperature, the reaction was quenched with 20 mL of acetone and 300 mL of 20% potassium, sodium tartrate. The compound was extracted with EtOAc, dried over $Na_2SO_4$, evaporated and purified by flash chromatography to provide 19 g of material.

Step 2 1-[3-(Isopropoxy)-2-[(isopropoxy)methyl]-2-(4-bromobenzyl)propyl]-4-bromobenzene benzyl 3-(benzyloxy)-2,2-bis(4-bromobenzyl)propyl ether To the dibromide of Step 1 (1.00 g, 3.00 mmol) in $CH_2Cl_2$ (30 mL) at −78° C. were added 2-iodopropane (2 mL) and silver trifluoromethane sulfate (1.70 g, 6.64 mmol) and 2,6-diterbutyl-4-methyl-pyridine (1.40 g, 6.82 mmol). After 3 days at r.t., the reaction mixture was filtered and the organic solvent evaporated under reduced pressure. To the crude product was added hexane and filtered to provide the title product in the filtrate.

Step 3 4-[3-(isopropoxy)-2-[(isopropoxy)methyl]-2-(4-formylbenzyl) propyl]benzaldehyde To the compound of Step 2 (0.73 g, 1.47 mmol) in THF (8 mL) at −78° C. was added n-BuLi (2.80 mL, 4.41 mmol). After a period of 40 min. at −78° C., DMF (1.1 mL) was added and the reaction stirred at room temperature. The reaction mixture was partitioned between $NH_4OAc$ and EtOAc. The organic phase was separated, dried over $Na_2SO_4$, filtered and evaporated. The title compound was purified by flash chromatography to provide 356 mg of a white solid.

Step 4 2,2-Di(4-I[(di-tert-butoxyphosphoryl)carbonyl)]benzyl)-1,3-propanediol,diisopropyl ether The title compound was prepared as described for Example 11.

Step 5 2,2-Di-(4-[(di-tert-butoxyphosphoryl)(difluoro) methylbenzyl)-1,3-propanediol,diisopropyl ether The title compound was prepared as described for Example 11.

Step 6 {4-[2-{4-[difluoro(phosphono)methyl]benzyl}-3-isopropoxy-2-(isopropoxymethyl)propyl]phenyl}(difluoro To the compound of Step 5 (0.140 g) were added AcOH (2.0 mL) and a few drops of $H_2O$. After a period of 24 h, the solvents were evaporated to give the title compound.

$^1$H NMR (300 MHz, $(CD_3COCD_3)$ δ1.10 (12H, d), 3.80 (4H, s), 3.90 (4H, s), 7.40 (8H, m).

EXAMPLE 20

(4-{3-(Benzyloxy)-2-[((Benzyloxy)Carbonyl]-3-Oxo-2-[4-(Trifluoromethyl)Benzyl]Propyl}Phenyl) (Difluoro) Methylphosphonic Acid Step 1 Dibenzyl 2-{4-[[di(tert-butoxy)phosphoryl](difluoro)methyl]benzyl}-2-[4-(trifluoromethyl)benzyl]malonate To a solution of the product from Example 18, Step 1 (94 mg, 0.15 mmol) in DMF (2 mL) at 0° C. was added NaH (5.5 mg, 80% in oil). After 15 min., 4-(trifluoromethyl)benzyl bromide (44 mg, 0.18 mmol) was added. After 2 h at 0° C., the mixture was given a standard aqueous/$Et_2O$ work-up, and the residue was purified by flash chromatography (1:10 EtOAc/hexane) to give a syrup (53 mg).

Step 2 (4-{3-(benzyloxy)-2-[(benzyloxy)carbonyl]-3-oxo-2-[4-(trifluoromethyl)benzyl]propyl}phenyl)(difluoro) methylphosp honic acid Prepared in the same manner as Example 16,. Step 5.

$^1$H NMR (400 MHz, acetone $d_6$) δ3.27–3.34 (m, 4H), 5.04–5.10 (m, 4H), 7.20–7.26 (m, 4H), 7.26–7.35 (m, 8H), 7.37–7.41 (m, 2H), 7.48–7.54 (m, 2H), 7.54–7.58 (m, 2H).

EXAMPLE 21

(4-{3-(Benzyloxy)-2-[(Benzyloxy)Carbonyl]-3-Oxo-2-[4-(Trifluoromethoxy)Benzyl]Propyl}Phenyl) (Difluoro)Methylphosphonic Acid Step 1 Dibenzyl 2-(4-[[di(tert-butoxy)phosphoryl)] (difluoro)methyl]benzyl}-2-[4-(trifluoromethoxy)benzyl] malonate The compound was prepared as described in Example 18, using 4-(trifluoromethoxy)benzyl methane sulfonate.

Step 2 (4-{3-(benzyloxy)-2-[(benzyloxy)carbonyl]-3-oxo-2-[4-(trifluoromethoxy)benzyl]propyl]phenyl)(difluoro) methylphosphonic acid The title compound was prepared as described in Example 23, Step 5.

$^1$H NMR (400 MHz, $CD_3COCD_3$) δ3.20 (2H, s), 3.25 (2H, s), 5.00 (4H, s), 7.20–7.50 (18 H, m).

EXAMPLE 22

(4-[(2-Benzyl)-3-(Benzyloxy)-2-[(Benzyloxy) Methyl]Propyl]Phenyl) (Difluoro)Methylphosphonic Acid M.S. Calculated for $C_{32}H_{33}F_2O_5P$: 566.2 Found: 565.1 (M−1).

EXAMPLE 23

(4-(3-(Benzyloxy)-2-[(Benzyloxy)Carbonyl]-2-{4-[(Dimethylamino)Sulfonyl)Benzyl]-3-Oxopropyl) Phenyl](Difluoro)Methylphosphonic Acid Prepared as described for Example 23 except dimethylamine was used.

$^1$H NMR (400 MHz, $CD_3COCD_3$) δ2.70 (6H, s), 3.20 (4H, 2s), 5.00 (4H, m), 7.20–7.80 (18, m).

EXAMPLE 24

(4-{2-{4-[(Acetylamino)Sulfonyl]Benzyl}-3-Benzyloxy)-2-[(Benzyloxy)Carbonyl]-3-Oxopropyl}Phenyl)Difluoro) Methylphosphonic Acid To a solution of the product from Example 16, Step 4 (0.23 g) in pyridine was added acetic anhydride (0.5 mL) and DMAP (≈20 mg). After stirring at r.t. for 5 h, the solvent was removed under vacuum. The residue was co-evaporated with toluene, and was then dissolved in HOAc (4 mL) and $H_2O$ (0.5 mL). The mixture was stirred overnight and the solvent was then removed under vacuum. The residue was purified by reverse phase HPLC.

$^1$H NMR (400 MHz, acetone $d_6$) δ1.98 (s, 3H), 3.27–3.35 (m, 4H), 5.00–5.17 (m, 4H), 7.17–7.43 (m, 14H), 7.49–7.56 (m, 2H), 7.85–7.92 (m, 2H).

EXAMPLE 25

(4-{3-(Benzyloxy)-2-[(Benzyloxy)Carbonyl]-2-[(1,3-Dioxo-1,3-Dihydro-2H-Isoindol-2-yl)Methyl]-3-Oxopropyl}Phenyl) (Difluoro)Methylphosphonic Acid The title compound was prepared as described for Example 18 except using N-(Bromomethyl)-phthalimide as alkylating agent.

$^1$H NMR (400 MHz, acetone-$d_6$) δ7.90 (4H, m), 7.50 (4H, s), 7.20–7.35 (10H, m), 4.52–5.10 (4H, q), 4.35 (2H, s), 3.35 (2H, s).

EXAMPLE 26

(4-{3-(Benzyloxy)-2-[(Benzyloxy)Carbonyl]-3-Oxo-2-[4-(1,2,3-Thiadiazol-4-yl)Benzyl]Propyl}Phenyl) (Difluoro) Methylphosphonic Acid The title compound was prepared as described for Example 18 using 4-(4-bromomethylphenyl)-1,2,3-thiadiazole.

$^1$H NMR (400 MHz, acetone-$d_6$) δ9.30 (1H, s), 8.05 (2H, d), 7.55 (2H, d), 7.25–7.35 (14H), 5.05 (4H, q), 3.30 (4H, d).

EXAMPLE 27

{4-[(2-{4-[Difluoro(Phosphono)Methyl]Benzyl}-1,3-Dioxo-2,3-Dihydro-1H-inden-2-yl)Methyl) Phenyl}(Difluoro) Methylphosphonic Acid To 1,3-indanone (0.040 g, 0.273 mmol) in $CH_3CN$ (2.0 mL) were added di(tert-butyl)[(4-bromomethyl]phenyl] (difluoro)methyl phosphonate (0.205 g, 0.566 mmol) and KF/celite (0.320 g). After a period of 1.5 h at room temperature, the mixture was filtered over celite and purified by flash chromatography. The ester was treated as described in Example 19, Step 6.

$^1$H NMR (400 MHz, $CD_3COCD_3$) δ3.30 (4H, s), 7.20 (4H, m), 7.70 (4H, s).

EXAMPLE 28

2-[4-(3-(Benzyloxy)-2-[(Benzyloxy)Methyl]-2-(4-[Difluoro(Phosphono)Methyl]Benzyl)Propyl) Phenyl]-2,2-Difluoroacetic Acid Step 1 Dimethyl 2-(4-bromobenzyl)malonate A solution of dimethyl malonate (13.2 g), 4-bromobenzylbromide (5.4 g) in DMF (200 mL) was treated with NaH (4 g, 60% in mineral oil). The mixture was stirred for 5 min at 0° C. and 20 min at room temperature and then quenched with 10 mL of AcOH slowly. The mixture was concentrated under vacuum and the residue was dissolved in 200 mL of 1:1 EtOAc/hexane, and filtered through a pad of silica gel. The filtrate was concentrated and the excess dimethyl malonate was removed under vacuum at 70° C. to provide the title compound as a yellow oil.

Step 2 Dimethyl 2-(4-bromobenzyl)-2-[4-(diethoxymethyl) benzyl]malonate

A solution of dimethyl 2-(4-bromobenzyl)malonate (4.2 g), 1-(bromomethyl)-4-(diethoxymethyl)benzene (4 g) in DMF (50 mL) was treated with NaH (0.8 g, 60% in mineral oil). The mixture was stirred for 2 h at 60° C., and then quenched with 100 mL of 50% saturated $NH_4Cl$. The product was extracted with 200 mL of 2:1 hexane/EtOAc. The extract was dried over $Na_2SO_4$ and concentrated, and dried under vacuum to give the title compound which was used without further purification.

Step 3 2-(4-Bromobenzyl)-2-[4-(diethoxymethyl)benzyl]-1, 3-propanediol

To a solution Dimethyl 2-(4-bromobenzyl)-2-[4-(diethoxymethyl) benzyl]malonate(crude from Step 2) in 200 mL of THF cooled at 0° C. was added of $LiAlH_4$ (0.8 g). The mixture was stirred for 2 h at room temperature and the quenched with acetone (5 mL), followed by 100 mL of 20% aqueous sodium potassium tartrate solution. The mixture was extracted with 200 ML of 2:1 hexane/EtOAc. The extract was dried over $Na_2SO_4$ and concentrated to give the crude product which was purified by silica gel chromatography eluted with 2:1 hexane EtOAc containing 1% of $Et_3N$ to give 4.2 g of the title compound.

Step 4 1-[3-(Benzyloxy)-2-[(benzyloxy)methyl]-2-(4-bromobenzyl)propyl]-4-(diethoxymethyl)benzene A mixture of 2-(4-Bromobenzyl)-2-[4-(diethoxymethyl) benzyl]-1,3-propanediol(3 g, crude), benzyl bromide (3 mL), and NaH (1.2 g, 60% in mineral oil) in 30 mL of DMF was stirred for 14 h at 70° C. The mixture was then quenched with 5 mL of MeOH followed by 50 mL of saturated $NH_4Cl$ and extracted with 200 mL of 2:1 hexane/EtOAc. The extract was dried over $Na_2SO_4$ and concentrated. The residue was purified by silica gel chromatography eluted with 15:1 hexane EtOAc containing 1% of $Et_3N$ to give 2.5 g of the title compound as an oil.

Step 5 Ethyl 2-(4-3-(benzyloxy)-2-[(benzyloxy)methyl]-2-[4-(diethoxymethyl)benzyl]propylphenyl)-2-oxoacetate To a solution of 1-[3-(benzyloxy)-2-[(benzyloxy)methyl]-2-(4-bromobenzyl)propyl]-4-(diethoxymethyl)benzene (2 g) in 40 mL of ether cooled at −78° C. was added dropwise a t-BuLi solution (5 mL, 1.4 M in pentane). After stirring for 5 min, 5 mL of $(CO_2Et)_2$ was added and the mixture was warmed to room temperature over 5 min, and then quenched with 50 mL of saturated NH4Cl. The mixture was extracted with 100 mL of hexane/EtOAc and the extract was dried over $Na_2SO_4$. After concentration, the excess $(CO2Et)2$ was removed under vacuum at 50° C. and the crude product was purified by silica gel chromatography eluted with 10:1 hexane/EtOAc containing 1% of $Et_3N$ to give 1.2 g of the title compound.

Step 6 Ethyl 2-4-[3-(benzyloxy)-2-[(benzyloxy)methyl]-2-(4-formylbenzyl) propyl]phenyl-2,2-difluoroacetate Diethylaminosulfur trifluoride (3 mL) and the product from Step 5 (1.0 g) were mixed at 0° C. The mixture was allowed to warm to room temperature and stirred at room temperature for 18 h. $Et_3N$ (2 mL) was then added and the reaction mixture was then poured into an ice-cold mixture of 50 mL of 1:1 hexane/EtOAc and 50 mL of saturated $NaHCO_3$ with vigorous stirring. The organic layer was separated, dried over $Na_2SO_4$, and concentrated. The residue was dissolved in a mixture of 10 mL AcOH, 0.5 mL TFA and 2 mL of water. After stirring for 30 min at room temperature, the mixture was co-evaporated with 2×20 mL toluene and the residue was purified by silica gel chromatography eluted with 3:1 hexane/EtOAc to give 0.9 g of the title compound as a yellow oil.

Step 7 Ethyl 2-[4-(3-(benzyloxy)-2-[(benzyloxy)methyl]-2-4-[(ditert-butoxyphosphoryl)(hydroxy)methyl]benzylpropyl)phenyl]-2,2-difluoroacetate To a solution of di-tert-butylphosphite (0.78 g) in THF (60 mL) cooled at −78° C. was added dropwise a solution of $LiN(TMS)_2$ (4 mL, 1M in THF). After stirring for 30 min at −78° C., a solution of ethyl 2-4-[3-(benzyloxy)-2-[(benzyloxy)methyl]-2-(4-formylbenzyl)propyl]phenyl-2,2-difluoroacetate(1 g in 20 mL of THF) was added. The reaction mixture was stirred for 5 min at −78° C. and 15 min at 0° C., and then quenched with 30 mL of 50% saturated aqueous $NH_4Cl$ solution. The mixture was extracted with 80 mL of EtOAc and the extract was dried over $Na_2SO_4$. After concentration, the crude product was purified by silica gel chromatography eluted with 2:1 EtOAc/hexane to give 1.1 g of the title product as an oil.

Step 8 Ethyl 2-[4-(3-(benzyloxy)-2-[(benzyloxy)methyl]-2-4-[(ditert-butoxyphosphoryl)carbonyl]benzylpropyl) phenyl]-2,2-difluoroacetate The product obtained in Step 7 (1.1 g) was oxidized under the same conditions as described in Step 2 of Example 1 to give 1.1 g of the crude title compound which was used for next step without further purification.

Step 9 Ethyl 2-[4-(3-(benzyloxy)-2-[(benzyloxy)methyl]-2-4-[(ditert-butoxyphosphoryl)(difluoro)methyl]benzylpropyl)phenyl]-2,2-difluoroacetate Diethylamonosulphur trfluoride (6 mL) and the product from Step 8 (1.1 g) were mixed at −78° C. The mixture was allowed to warm slowly to room temperature over a period of 30 min and stirred at room temperature for 2 days. The reaction mixture was then poured into a mixture 200 mL of 1:1 hexane/EtOAc containing, 150 mL of saturated $NaHCO_3$, 50 g of ice and 5 mL of $Et_3N$ at 0° C. with vigorous stirring. The organic layer was separated, dried over $Na_2SO_4$, and concentrated. The residue was purified by silica gel chromatography eluted with 4:1 hexane/EtOAc to give 0.5 g of the title compound as a yellow oil.

Step 10 2-[$^4$-(3-(Benzyloxy)-2-[(benzyloxy)methyl]-2-4-[difluoro(phosphono)methyl]benzylpropyl)phenyl]-2,2-difluoroacetic acid To solution of the product from Step 9 (0.4 g) in 5 mL of THF and 4 mL of water was added 1.5 mL of 1N NaOH. The reaction mixture was stirred for 10 min at room temperature and then treated with 10 mL of PH7 phosphate buffer. The mixture was extracted with 50 mL of EtOAc and the extract was dried over Na2SO4 and concentrated. The residue was dissolved in a mixture of 10 mL of AcOH, 1 mL of water and 0.1 mL of TFA. The solution was stirred for 14 h at room temperature and concentrated to give 0.3 g of the title compound.

$^1$H NMR (400 MHz, methanol-$d_4$) δ9.2–9.45 (3H, bs), 7.43–7.50 (8 H, m), 7.35–7.40 (4H, m), 7.25–7.35 (6H, m), 4.48 (4H, dd), 2.95 (4H, dd), 2.89 (4H, dd).

EXAMPLE 29

(4-(2-[4-(Aminosulfonyl)Benzyl]-3-(Benzyloxy)-2-[(Benzyloxy)Methyl]Propyl)Phenyl) (Difluoro) Methylphosphonic Acid Step 1 Dimethyl 2-(4-(diethoxymethyl)benzyl)malonate To a solution of dimethyl malonate (4.96 mL, 43 mmol) in DMF (80 mL) was added NaH (1.3 g 80% in mineral oil). After 20 min. a solution of 1-(bromomethyl)-4-(diethoxymethyl)benzene (2.37 g, 8.7 mmol) in DMF (5 mL) was added via double-tipped needle. After 1 h at 0° C., the reaction was quenched by the addition of saturated $NH_4Cl$ solution. The product was extracted with $Et_2O$ and the organic layer wash washed with $H_2O$ and brine. After drying (MgSO$_4$) and filtration, the solvent was removed under vacuum. The crude was purified by flash chromatography (1:10 EtOAc/hexane) to yield a colorless oil (1:42 g).

Step 2 Dimethyl 2-(4-(diethoxymethyl)benzyl)-2-(4-(methylthio) benzyl)malonate

To a solution of the product from Step 1 (1.42 g, 4.4 mmol) in DMF (14 mL) at 0° C. was added NaH (131 mg, 80% in mineral oil). After 1 h. 4-(methylthio)benzyl chloride (0.64 mL, 4.4 mmol) was added and the mixture was stirred a further 2 h at 0° C. Following a standard aqueous/Et$_2$O work-up, the crude was purified by flash column (1:20 EtOAc/toluene) to give a colorless oil (1.92 g).

Step 3 2-(4-(diethoxymethyl)benzyl)-2-(4-(methylthio)benzyl)-1,3-propanediol

Prepared in the same manner as described in Example 28, Step 3.

Step 4 1-(3-(benzyloxy)-2-((benzyloxy)methyl-2-(4-(diethoxymethyl) benzyl)propyl)-4-(methylthio)benzene Prepared in the same manner as described in Example 28 Step 4.

Step 5 4-(3-(benzyloxy)-2-((benxyloxy)methyl)-2-(4-(diethoxymethyl)benzyl)propyl)phenyl methyl sulfoxide To a solution of the thioether from Step 4 (100 mg, 0.17 mmol) in CH$_2$Cl$_2$ (2 mL) and MeOH (1 mL) at 0° C. was added MMPP (48 mg, 0.077 mmol). After 1 h at 0° C., H$_2$O (10 mL) was added and the product was extracted with CH$_2$Cl$_2$. The organic layer was dried (MgSO$_4$), filtered, and evaporated. The residue was purified by flash chromatography (1:2 EtOAc:hexane) to give a colorless syrup (78 mg).

Step 6 4-(3-(benzyloxy)-2-((benzyloxy)methyl)-2-(4-(methylsulfinyl) benzyl)propyl)benzaldehyde To a solution of the sulfoxide from Step 5 (38 mg) in acetone (2 mL) at r.t. was added TsOH (1 mg). After stirring for 1 h at r.t., the solvent was evaporated and the residue was purified by flash chromatography (2:1 EtOAc:hexane) to give a colorless oil (35 mg).

Step 7 ((4-(3-(benzyloxy)-2-((benzyloxy)methyl)-2-(4-formylbenzyl) propyl)thio)methyl acetate To a solution of the aldehyde from Step 6 (35 mg) in acetic anhydride was added NaOAc (35 mg). The mixture was stirred under reflux overnight. The solvent was then removed under vacuum and the residue was taken up in EtOAc/H$_2$O. The organic phase was dried (MgSO$_4$), filtered, and evaporated. Purification was effected by flash chromatography to give a colorless syrup (13 mg).

Step 8 ((4-(3-benzyloxy)-2-((benzyloxymethyl)-2-(4-formylbenzyl) propyl)phenyl)sulfonyl)methyl acetate To a solution of the methyl acetate from Step 7 (135 mg, 0.24 mmol) in CH$_2$Cl$_2$ (2 mL) and MeOH (1 mL) at 0° C. was added MMPP (200 mg, 0.32 mmol). The mixture was stirred 30 min. at 0° C. followed by 2 h at r.t. H$_2$O (10 mL) was then added, and the product was extracted with CH$_2$Cl$_2$. The organic layer was then dried (MgSO$_4$), filtered, and evaporated. The crude was purified by flash chromatography to give a colorless syrup (58 mg).

Step 9 4-(3-benzyloxy)-2-((benzyloxy)methyl)-2-(4-formylbenzyl) propyl)benzenesulfonamide To a solution of the sulfone from Step 8 (58 mg, 0.097 mmol) in THF (2 mL), and MeOH (1 mL) at 0° C. was added 1 M NaOH (97 μL, 0.097 mmol). The mixture was stirred at 0° C. for 1 h, at which point the solvent was removed under vacuum. The residue was co-evaporated twice with EtOAc/toluene, and was then dissolved in CH$_2$Cl$_2$ (2 mL). After cooling to 0° C., SO$_2$Cl$_2$ (8 μL, 0.097 mmol) was added, and the mixture was stirred for 20 min. at 0° C. Saturated NaHCO$_3$ (1 mL) was then added and the sulfonyl chloride was extracted with CH$_2$Cl$_2$. The organic layer was dried (MgSO$_4$), filtered, and evaporated. The residue was taken up in THF, and NH$_4$OH (1 mL) was added at 0° C. The solvent was removed under vacuum and the residue was purified by flash chromatography (1:2 EtOAc:hexane) to give an oil (54 mg).

Step 10 Di(tert-butyl) (4-[2-(4-aminosulfonyl)benzyl)-3-(benzyloxy)-2-((benzyloxy)methyl)propyl]phenyl) hydroxymethylphosphonate To a solution of di-t-butyl phoshite (43 μL, 0.22 mmol) in THF (1 mL) at −78° C. was added LiHMDS (218 μL, 0.22 mmol, 1M/THF). After 15 min at −78° C., a solution of the sulfonamide from Step 9 (54 mg, 0.1 mmol) in THF (2 mL) was added via double-tipped needle. The reaction mixture was then stirred at −0° C. for 1 h. A solution of NH$_4$OAc (5 mL, 1M) was then added and the product was extracted with EtOAc. The organic layer was dried (MgSO$_4$), filtered, and evaporated. The crude product was used as such for the next step.

Step 11 Di(tert-butyl)-4-[2-(4-aminosulfonyl)benzyl)-3-(benzyloxy)-2-((benzyloxy)methyl)propyl] benzoylphosphonate To a solution of the alcohol from Step 10 (~0.1 mmol) in EtOAc (4 mL) was added MnO$_2$ (300 mg). After stirring for 1 h at r.t., the suspension was filtered through a bed of celite. The filtrate was evaporated to give a crude product (67 mg) which was used as such in the following step.

Step 12 Di(tert-butyl) (4-[2-(4-(aminosulfonyl)benzyl)-3-(benzyloxy)-2-((benzyloxy)methyl)propyl]phenyl) (difluoromethylphosphonate)

The ketone from Step 11 (~0. 1 mmol) was dissolved in diethylaminosulfur trifluoride (0.26 mL). After stirring at r.t. for 8 h, the reaction was carefully quenched at 0° C. by the addition of ice-cold EtOAc (1% Et$_3$N)/saturated NaHCO$_3$. The organic phase was dried (MgSO4), filtered, and evaporated. The crude product was purified by flash chromatography (1:2 EtOAc:hexane followed by 1:1 EtOAc:hexane) to give a colorless oil (28 mg).

Step 13 (4-[2-(4-(aminosulfonyl)benzyl)-3-(benzyloxy)-2-((benzyloxy) methyl)propyl]phenyl(difluoro) methylphosphonic acid The difluoromethyl phosphonate from Step 12 (28 mg) was dissolved in HOAc (3 mL) and H$_2$O (0.5 mL), and the resulting solution was stirred ON at r.t. The solvent was then evaporated under vacuum and the residue was co-evaporated 3 times with toluene to give a tan colored gum (25 mg).

$^1$H NMR (500 MHz, acetone d$_6$) δ2.87–2.92 (m, 4H), 2.92–3.01 (m, 4H), 4.46–4.54 (m, 4H), 6.5 (6s, 2H), 7.25–7.35 (m, 6H), 7.35–7.42 (m, 4H), 7.42–7.51 (m, 6H), 7.70–7.75 (m, 2H).

EXAMPLE 30

[4-(2-{4-[Difluoro(Phosphono)Methyl]Benzyl}-3-Oxo-2,3-Diphenylpropyl)Phenyl](Difluoro) Methylphosphonic Acid Step 1 Di(tert-butyl)[4-(2-{4-[[di(tert-butoxy)phosphoryl](difluoro)methyl]benzyl}-3-oxo-2,3-diphenylpropyl) phenyl](difluoro)methylphosphonate To 2-deoxybenzoin (0.100 g, 0.510 mmol) in DMF (3 mL) were added at 0° C. nBu$_4$NI (catalytic), NaH (0.050 g, 1.25 mmol) and di(tert-butyl)[(4-bromomethyl)phenyl] (0.462 g, 1.12 mmol). After 1 h at room temperature, the reaction mixture was partitioned between H$_2$O and ether. After usual workup procedure and purification by flash chromatography, the title compound was obtained.
(Alternative Step 1)

To deoxybenzoin (0.216 g, 1.10 mmol) in THF (5.5 mL) were added nBu$_4$NI (catalytic) and a trace of 18-crown-6. To the previous mixtures at 0° C., was added potassium tert-butoxide (2.42 mL, 2.42 mmol) 1M in THF. After a period of 15 min. at 0° C., di(tert-butyl)[4-(bromomethyl)phenyl](difluoro)methylphosphonate (1.00 g, 2.42 mmol) in THF (2.0 mL) was added at −78° C. After a period of 15 min at 0° C. and 0.5 h at 0° C., the reaction mixture was quenched as described in the previous preparation.

Step 2 [4-(2-{4-[difluoro(phosphono)methyl]benzyl}-3-oxo-2,3-diphenylpropyl)phenyl](difluoro)methylphosphonic acid The compound of Step 1 was treated as described for Example 19, Step 6.

$^1$H NMR (300 MHz, $CD_3COCD_3$) δ3.60 (4H, s), 6.90–7.70 (18H, m).

EXAMPLE 31

Di{4-[Difluoro(Phosphono)Methyl]Benzyl}-Bis(2-Benzothiazolyl)Methane

Step 1 Bis(2-benzothiazolyl)methane

Malonic acid (5.2 g) and 2-aminothiophenol (6.3 g) were mixed with 65 mL of PPA at 120° C. (C. Rai J.B. Braunwarth, J. Org. Chem. 26, 3434, 1961). A exothermic reaction took place while mixing. The mixture was kept at 120° C. for 1 h and then poured into a mixture of 200 mL of water and 100 g of ice. The solid was collected, dried and swished to give 3 g of the title compound as a yellow solid.

Step 2 Di{4-[difluoro(phosphono)methyl]benzyl}-bis(2-benzothiazolyl) methane

The title compound was prepared by using the same procedure described in Step 5 and 6 of Example 1.

$^1$H NMR (400 MHz, methanol-$d_4$) δ8.10 (2H, d), 8.05 (2H, d), 7.53 (2H, t), 7.47 (2H, t), 7.16 (4H, d), 7.33 (4H, d), 3.98 (4H, s).

EXAMPLE 32

2-[4-(2-{4-[Difluoro(Phosphono)Methyl]Benzyl}-3-Oxo-2,3-Diphenylpropyl)Phenoxy]-2,2-Difluoroacetic Acid The title compound was prepared from tert-butyl 2-[4-(bromomethyl)phenoxy]-2,2-difluoroacetate (prepared according to H. Fretz, Tetrahedron 54, 4849, 1998) and deoxybenzoin by using the same procedure described in Example 31 except TFA was used in the hydrolysis step instead of acetic acid.

$^1$H NMR (400 MHz, methanol-$d_4$) δ7.59 (2H, d), 7.42 (1H, t), 7.25–7.38 (6H, m), 7.16 (2H, m), 6.96 (2H, d), 6.92 (2H, d), 6.82 (3H, m), 3.50–3.70 (3H, m), 3.46 (1H, d).

EXAMPLE 33

(4-{2-{4-[Difluoro(Phosphono)Methyl]Benzyl}-3-(3-Fluorophenyl)-2-[4-(Methylsulfanyl)Phenyl-3-Oxopropyl}Phenyl)(Difluoro)Methyl Phosphonic Acid Step 1 3-Fluoro-N-methoxy-N-methylbenzamide To a mixture of 3-fluorobenzoyl chloride (11.0 g, 6.70 mmol) and N,O-dimethylhydroxylamine.HCl in $CHCl_3$ (70 mL) at 0° C. was added pyridine (14 mL) over 30 min. After a period of 3 h at room temperature, the reaction mixture was treated in the usual manner to give 12.5 g of the title compound.

Step 2 1-(3-fluorophenyl)-2-[4-(methylsulfanyl)phenyl]-1-ethanone

To an excess of Mg (8 g) in ether (100 mL) containing 12 (catalytic) was added dropwise neat 4-chloromethyl thiomethyl benzene (13.5 g, 7.84 mmol) over a period of 30 min. After completion of the addition, the mixture was stirred at room temperature for 15 min. The Grignard Reagent was added dropwise to the amide of Step 1 in THF (200 mL) at 0° C. over 15 min. After a period of 30 min the mixture was treated the usual manner. The solid was treated with a 1/1 mixture of ether/hexane to give 10.5 g of the title compound.

Step 3 (4-{2-{4-[difluoro(phosphono)methyl]benzyl}-3-(3-fluorophenyl)-2-[4-(methylsulfanyl)phenyl]-3-oxopropyl] phenyl)(difluoro)methyl phosphonic acid The title compound was prepared as described for Example 31 using 1-(3-fluorophenyl)-2-[4-(methylsulfanyl)phenyl]-1-ethanone of Step 2.

$^1$H NMR (300 MHz, $CD_3COCD_3$) δ2.50 (3H, s), 3.50 (4H, s), 6.90–7.20 (16H, m).

EXAMPLE 34

(4-{2-{4-[Difluoro(Phosphono)Methyl]Benzyl}-3-(3-Fluoro-4-Methoxyphenyl)-2-[4-(Methylsulfonyl)Phenyl]-3-Oxopropyl}Phenyl)(Difluoro)Methylphosphonic Acid Step 1 2-(3-fluoro-4-methoxyphenyl)-2-[(trimethylsilyl)oxy]acetonitrile To 3-fluoro-4-methoxybenzaldehyde (2.80 g, 1.81 mmol) in 1,2-dichloroethane (20 mL) containing $ZnI_2$ (0.020 g) was added TMSCN (2.5 mL). After a period of 2 h, the solvent was removed under reduced pressure to give the title compound (4.7 g).

Step 2 1-(3-fluoro-4-methoxyphenyl)-2-[4-(methylsulfanyl)phenyl]-1-ethanone

To 1M LiHMDS in THF (20 mL, 20 mmol) at −78° C. was added the cyanohydrin of Step 1. After 4-chloromethyl thiomethyl benzene (3.80 g, 22.1 mmol) in THF was then added to the previous solution. After warming to r.t., the mixture was then hydrolyzed with HCl, $H_2O$, MeOH for 30 min. After usual workup the crude product was treated with ether and filtered to give 3.7 g f the title compound.

Step 3 1-(3-Fluoro-4-methoxyphenyl)-2-[4-(methylsulfonyl)phenyl]-1-ethanone

The thioether of Step 2 was then oxidized with mCPBA to give the sulfone.

Step 4 (4-{2-{4-[difluoro(phosphono)methyl]benzyl}-3-(3-fluoro-4-methoxyphenyl)-2-[4-(methylsulfonyl)phenyl]-3-oxopropyl}phenyl)(difluoro)methylphosphonic acid The title compound was prepared as described for Example 31.

$^1$H NMR (400 MHz, acetone-$d_6$), δ7.80 (2H, d), 7.45 (1H, d), 7.30 (7H, m), 6.95 (5H, m), 3.9 (3H, s), 3.65 (4H, q), 3.10 (3H, s).

EXAMPLE 35

(4-{2-[4-(Aminosulfonyl)Benzyl]-3-Oxo-2,3-Diphenylpropyl}Phenyl)(Difluoro)Methyl Phosphonic Acid Step 1 Di(tert-butyl){4-[2-(4-{[bis(2,4-dimethoxyphenyl)amino]sulfonyl}benzyl)-3-oxo-2,3-diphenylpropyl]phenyl} (difluoro) methylphosphonate Prepared in the same manner as Example 33, Step 1 using 4-(bromomethyl)-N,N-bis(2,4-dimethoxyphenyl) benzenesulfonamide as the alkylating agent.

Step 2 Di(tert-butyl){4-[2-(4-{[bis(2,4-dimethoxyphenyl)amino]sulfonyl}benzyl)-3-oxo-2,3-diphenylpropyl]phenyl} (difluoro)methylphosphonate To a solution of the sulfonamide from Step 1 (108 mg) in DMF (5 mL) was added NaH (25 mg, 60% in oil) and Bu4NI (≈20 mg). After 10 min., di(tert-butyl) [4-(bromomethyl)

phenyl](difluoro) methylphosphonate (160 mg) was added, and the mixture was stirred at r.t. for 1 h. Following a standard aqueous work-up, the residue was purified by flash chromatography (30% EtOAc:hexane, then 40% EtOAc:hexane) to give a syrup (30 mg).
Step 3 (4-{2-[4-(aminosulfonyl)benzyl]-3-oxo-2,3-diphenylpropyl]phenyl)(difluoro)methylphosphonic acid The product from Step 2 (30 mg) was dissolved in 9:1 TFA:H$_2$O (2 mL) and the resulting solution was stirred for 2 h at r.t. The solvent was then removed under vacuum and the residue was purified by reverse phase HPLC. Following lyophilization, a foam was obtained (20 mg).
$^1$H NMR (400 MHz, acetone d$_6$) δ3.49–3.67 (m, 4H), 6.50 (bs, 2H), 6.87–6.96 (m, 4H), 7.13–7.19 (m, 2H), 7.26–7.39 (m, 6H), 7.40–7.47 (m, 2H), 7.56–7.62 (m, 4H).

EXAMPLE 36

(4-{2-{4-[Difluoro(Phosphono)Methyl]Benzyl}-3-[4-(Methylsulfanyl)Phenyl]-3-Oxo-2-Phenylpropyl}Phenyl)(Difluoro)Methylphosphonic Acid The title compound was prepared as described in Example 31 using 1-[4-methylsulfanyl)phenyl]-2-phenyl-1-ethanone.
$^1$H NMR (CD$_3$COCD$_3$) δ2.30 (3H, s), 3.60 (4H, s), 6.40–7.60 (17 H, m).

EXAMPLE 37

[4-(2-Benzyl-3-Oxo-2,3-Diphenylpropyl)Phenyl] (Difluoro)Methylphosphonic Acid
Step 1 1,2,3-Triphenyl-1-propanone To deoxybenzoin (0.20 g, 1.02 mmol) in DMF (5 mL) were added at 0° C. NaH in oil (0.050 g, 1.22 mmol) and benzyl bromide (183 μL). After 1 h at room temperature, the reaction mixture was partitioned between NH$_4$OAc and ether. After usual work up procedure the title compound was purified by flash chromatography (0.95 g).
Step 2 Di(tert-butyl) [4-(2-benzyl-3-oxo-2,3-diphenylpropyl) phenyl](difluoro)methylphosphonate To the compound of Step 1 (0.150 g, 0.524 mmol) in DMF (2.6 mL) at 0° C. were added NaH in oil (0.025 g, 0.629 mmol) and di(tert-butyl)[[4-bromomethyl]phenyl](difluoro) methyl phosphonate (0.259 g, 0.629 mmol) and nBu$_4$NI (catalytic). After a period of 1 h at room temperature, the reaction mixture was partitioned between NH$_4$OAc and ether. After usual workup procedure and purification by flash chromatography, the title compound was obtained.
Step 3 [4-(2-benzyl-3-oxo-2,3-diphenylpropyl)phenyl] (difluoro)methylphosphonic acid The title compound was obtained using the procedure described in Example 31 Step 2.
$^1$H NMR (CD$_3$COCD$_3$) δ3.50 (4H, m), 6.90–7.70 (19H, m).

EXAMPLE 38

(4-{2-Benzotriazol-1-yl-3-[4-(Difluorophosphonomethyl)Phenyl]-2-Phenyl-Propyl}Phenyl)-Difluoromethylphosphonic Acid
Step 1 1-Benzyl-1H-benzotriazole To a solution of benzotriazole (1.2 g, 10.1 mmol) in DMF (40 mL) at r.t. was added a solution of 1M t-BuOK in THF (11 mL, 1 mmol). After stirring for 30 min., benzyl bromide (2.0 g, 11.6 mmol) was added. The mixture was further stirred for 1 h, diluted with H$_2$O, extracted with EtOAc. The EtOAc extract was washed H$_2$O (3×), dried (MgSO$_4$) and concentrated. The residue was swished with hexanes containing small amount of Et$_2$O to give 1.2 g (57%) of title compound as white powders.
$^1$H NMR (Acetone-d$_6$) δ8.00 (d, 1H), 7.72 (d, 1H), 7.48 (m, 1H), 7.42–7.25 (6H), 5.96 (s, 2H).
Step 2 (4-{2-Benzotriazol-1-yl-3-[4-(difluorophosphonomethyl)phenyl]-2-phenyl-propyl}phenyl)-difluoromethylphosphonic acid To a solution of 1-benzyl-1H-benzotriazole (63 mg, 0.3 mmol) in THF (5 mL) at −78° C. was added a solution of 2.5M n-BuLi in hexanes (265 μL, 0.66 mmol). The solution turned deep blue immediately. After stirring for 15 min at −78° C., a solution of (4-bromomethylphenyl)-difluoromethylphosphonic acid di-tert-butyl ester (300 mg, 0.7 mmol) in THF was added. The deep blue color disappeared. The mixture was then stirred at −78° C. for 1 h, quenched with H$_2$O and extracted with EtOAc. The EtOAc extract was washed with brine, dried (MgSO$_4$) and concentrated. Chromatography over silica gel and elution with hexanes:EtOAc (1:1) provided 45 mg of less polar fraction, which was the monoalkylated product. Further elution gave a more polar fraction. The polar fraction was chromatographed again on silica gel and eluted with hexanes:EtOAc (1:1) to afford 30 mg of dialkylated product.

The above dialkylated product was dissloved in 83% of aqueous HOAc (1.2 mL) and stirred at r.t overnight. After removal of solvents, the residue was co-evaporated with toluene (2×) and freeze-dried to give 22 mg of the title compound as a whilte foam.
$^1$H NMR (DMSO-d$_6$) δ8.00 (d, 1H), 7.40–7.24 (m, 6H), 7.18 (d, 4H), 7.05 (d, 2H), 6.70 (d, 1H), 6.65 (d, 4H), 3.95 (ABq, 4H).

EXAMPLE 39

2-(4-(2-{4-[Difluoro(Phosphono)Methyl)Benzyl)-3-Oxo-2,3-Diphenylpropyl)Phenyl]-2,2-Difluoroacetic Acid
Step 1 2-[4-(2-{4-{{di(tert-butoxy)phosphoryl](difluoro) methyl]benzyl}-3-oxo-2,3-diphenylpropyl)phenyl]-2,2-difluoroacetic acid To the compound of Example 33 (0.100 g, 0.189 mmol) in THF (0.90 mL) were added nBu$_4$NI (catalytic) and a trace of 18-crown-6. To this mixture at −78° C. was added potassium tert-butoxide (1M in THF, 0.208 mL) after a period of 10 min at −78° C., a THF solution (0.30 mL) of tert-butyl 2-[4-(bromomethyl)phenyl]-2,2-difluoroacetate] (0.066 g, 0.206 mmol) was added. After a period of 2 h, at 0° C., the reaction mixture was quenched as described for Example 31 Step 1.
Step 2 2-(4-(2-{4-[Difluoro(phosphono)methyl)benzyl)-3-oxo-2,3-diphenylpropyl)phenyl]-2,2-difluoroacetic acid The title compound was prepared as described in Example 19 Step 6.
$^1$H NMR (300 mH, acetone-d$_6$) δ3.50 (4H, m), 6.90–8.00 (18 H, m).

EXAMPLE 40

4-(2-{4-[Difluoro(Phosphono)Methyl]Benzyl}-3-Oxo-2,3-Diphenylpropyl)Benzoic Acid
Step 1 Methyl 4-(2-{4-[[di(tert-butoxy)phosphoryl] (difluoro)methyl]benzyl}-3-oxo-2,3-diphenylpropyl) benzoate The title compound was prepared as described in Example 45.

Step 2 4-(2-{4-[Difluoro(phosphono)methyl]benzyl}-3-oxo-2,3diphenylpropyl)benzoic acid To the compound of Step 1 (0.040 g, 0.059 mmol) was treated as described in Example 19 Step 6. To the crude mixture was added 2 mL of THF and 1 mL of 1N NaOH. After a period of 18 h at 60° C., the mixture was evaporated and purified by RP-HPLC.

$^1$H NMR (300 MHz, $CD_3COCD_3$) δ3.60 (4H, m), 6.80–8.10 (18 H, m).

EXAMPLE 41

(4-{2-{4-[Difluoro(Phosphono)Methyl]Benzyl}-3-(4-Fluorophenyl)-2-[4-(Methylsulfanyl)Phenyl]-3-Oxopropyl}Phenyl)(Difluoro)Methylphosphonic Acid Step 1 2-(4-fluorophenyl)-2-((trimethylsilyl)oxy)acetonitrile To a 1,2-dichloroethane (50 mL) solution of 4-fluorobenzaldehyde (50 mmol., 6.2 g) was added trimethylsilyl cyanide (50 mmol., 4.96 g) followed by zinc iodide (0.050 g). After 1.5 hour the mixture was evaporated to dryness with the help of carbon tetrachloride and put on high vacuum for 16 hours to yield the intermediate TMS cyanohydrin (11 g).

Step 2 1-(4-fluoro-phenyl)-2-(4-methylsulfanyl-phenyl)-ethanone

To a 78° C. solution of the cyanohydrin (70 mmol., 15.6 g) in THF (70 mL) was added LDA (75 mmol., 94 mL of a 0.8 M THF solution prepared from 2.1 M n-BuLi and diisopropyl amine in THF in the usual manner) dropwise and the mixture was stirred 1 hour at this temperature. Then 4-(methylthio)benzyl chloride (100 mmol., 17 g) as a THF (50 mL) solution was added and the mixture was stirred at c.a. 0° C. for 16 hours. The mixture was then cooled to −5° C. and a 1M THF solution of n-Bu4N+F− (100 mmol., 100 mL) was added dropwise. After 1.5 hour the mixture was poured on water and the pH adjusted to c.a. 9, then it was extracted with ethyl acetate (3x). The combined extracts were washed with brine, dried with magnesium sulfate and the solvents were removed in vacuo. The residue was swished in ethyl acetate and hexanes (1:25) to give a nearly pure ketone (17.9 g).

$^1$H NMR, $CD_3COCD_3$, (δ, ppm):8.15 (2H, dd), 7.15–7.35 (6H, m), 4.45 (2H, s), 2.45 (3H, s).

Step 3 (4-{2-{4-[difluoro(phosphono)methyl]benzyl}-3-(4-fluorophenyl)-2-[4-(methylsulfanyl)phenyl]-3-oxopropyl] phenyl)(difluoro) methylphosphonic acid Using the ethanone from Step 2, this compound was prepared in the same manner as Example 31, Steps 1 and 2.

$^1$H NMR (400 MHz, acetone-$d_6$) δ2.48 (s, 3H), 3.50–3.60 (m, 4H), 6.90–6.97 (m, 4H), 7.03–7.12 (m, 4H), 7.18–7.24 (m, 2H), 7.29–7.38 (m, 4H), 7.64–7.72 (m, 2H).

EXAMPLE 42

(4-{2-Benzotriazol-1-yl-2-(3,4-Difluorophenyl)-3-[4-(Difluorophosphonomethyl)-Phenyl] Propyl}Phenyl)-Difluoromethylphosphonic Acid Step 1: 1-(3,4-Difluorobenzyl)-1H-benzotriazole To a solution of benzotriazole (1.2 g, 10.1 mmol) in DMF (40 mL) at r.t. was added a solution of 1M t-BuOK in THF (11 mL, 11 mmol). After stirring for 30 min., 3,4-difluorobenzyl bromide (2.4 g, 11.6 mmol) was added. The mixture was further stirred for 1 h, diluted with $H_2O$, extracted with EtOAc. The EtOAc extract was washed $H_2O$ (3x), dried (MgSO$_4$) and concentrated. The residue was chromatographed over silica gel and eluted with hexanes:EtOAc (3:1), then (2:1) to afford 1.6 g (65%) of title compound as a white solid.

$^1$H NMR (Acetone-$d_6$) δ8.02 (d, 1H), 7.76 (d, 1H), 7.52 (m, 1H), 7.45–7.15 (4H), 6.00 (s, 2H).

Step 2: (4-{2-Benzotriazol-1-yl-2-(3,4-difluorophenyl)-3-[4-(difluorophosphono-methyl)phenyl]propyl}phenyl) difluoromethylphosphonic acid To a solution of 1-(3,4-difluorobenzyl-1H-benzotriazole (100 mg, 0.41 mmol) in THF (8 mL) at −78° C. was added a solution of 2.5M n-BuLi in hexanes (175 μL, 0.44 mmol). The solution turned deep blue immediately. After stirring for 5 min at −78° C., a solution of (4-bromomethylphenyl)-difluoromethylphosphonic acid di-tert-butyl ester (175 mg, 0.42 mmol) in THF (1 mL) was added. The deep blue color disappeared. The mixture was then stirred at −78° C. for 10 min and a solution of 2.5M n-BuLi in hexanes (175 μL, 0.44 mmol) was added again. The solution turned deep blue immediately again. After stirring for 5 min at −78° C., a solution of (4-bromomethylphenyl)-difluoromethylphosphonic acid di-tert-butyl ester (175 mg, 0.42 mmol) in THF (1 mL) was added and the deep blue color disappeared. After stirring at −78° C. for 10 min, the mixture was quenched with $H_2O$ and extracted with EtOAc. The EtOAc extract was washed with brine, dried ($Na_2SO_4$) and concentrated. Chromatography over silica gel and elution with hexanes:EtOAc (2:1), then (1:1) provided 250 mg of dialkylated intermediate as a pale yellow foam.

$^1$H NMR (Acetone-$d_6$) δ8.06 (d,1H), 7.45–7.10 (m, 8H), 6.94 (d, 1H), 6.84 (m, 5H), 4.20 (d, 2H), 3.97 (d, 2H), 1.41 (s, 18H0, 1.40 (s, 18H).

The above dialkylated product was dissloved in 83% of aqueous HOAc (6 mL) and stirred at r.t overnight. After removal of solvents, the residue was co-evaporated with toluene (2x) and freeze-dried to give 155 mg (55%) of the title compound as a white foam.

$^1$H NMR (DMSO-$d_6$) δ8.11 (d, 1H), 7.42–7.18 (m, 8H), 6.81 (d, 1H), 6.68 (m, 5H), 4.06 (d, 2H), 3.83 (d, 2H).

EXAMPLE 43

{4-[2-Benzotriazol-1-yl-3-(4-Bromophenyl)-2-Phenylpropyl]Phenyl}-Difluoromethylphosphonic Acid Step 1: [4-(2-Benzotriazol-1-yl-2-phenylethyl)phenyl] difluoromethylphosphonic acid di-tert-butyl ester To a solution of 1-benzyl-1H-benzotriazole (820 mg, 0.3 mmol) in THF (50 mL) at −78° C. was added a solution of 2.5M n-BuLi in hexanes (1.5 mL, 3.8 mmol). The solution turned deep blue immediately. After stirring for 5 min at −78° C., a solution of (4-bromomethylphenyl) difluoromethylphosphonic acid di-tert-butyl ester (1.4 g, 3.4 mmol) in THF (4 mL) was added. The deep blue color disappeared. The mixture was then stirred at −78° C. for 1 h, quenched with $H_2O$ and extracted with EtOAc. The EtOAc extract was washed with brine, dried ($Na_2SO_4$) and concentrated. The residue was swished with $Et_2O$ to give 1.77 g (84%) of the title compound as a white solid.

$^1$H NMR (Acetone-$d_6$) δ7.92 (d, 1H), 7.74 (d, 1H), 7.54 (d, 2H), 7.42–7.25 (m, 9H), 6.44 (dd, 1H), 4.21 (dd, 1H), 3.86 (dd, 1H), 1.30 (s, 9H), 1.28 (s, 9H).

Step 2: {4-[2-Benzotriazol-1-yl-3-(4-bromophenyl)-2-phenylpropyl]phenyl}-difluoromethylphosphonic acid di-tert butyl ester To a solution of [4-(2-benzotriazol-1-yl-2-phenylethyl) phenyl]difluoromethyl-phosphonic acid di-tert-butyl ester (250 mg, 0.46 mmol) in THF (5 mL) at −78° C. was added a solution of 2.5M n-BuLi in hexanes (190 μL, 0.48 mmol). The solution turned deep blue immediately. After stirring for 15 min at −78° C., a solution of 4-bromobenzyl bromide (130 mg, 0.52 mmol) in THF (0.5 mL) was added. The deep blue color disappeared. The mixture was then stirred at −78° C. for 15 min, quenched with $H_2O$ and extracted with EtOAc. The EtOAc extract was washed with brine, dried ($Na_2SO_4$) and concentrated. Chromatography over silica gel and elution with hexanes:EtOAc (2:1) gave 130 mg (40%) of the title compound as a white foam.

$^1$H NMR (Acetone-$d_6$) δ8.03 (d, 1H), 7.40–7.18 (m, 9H), 7.08 (d, 2H), 6.75 (m, 3H), 6.59 (d, 2H), 4.15 (d, 1H), 4.07 (d, 1H), 3.98 (d, 1H), 3.86 (d, 1H), 1.41 (s, 18H).

Step 3: {4-[2-Benzotriazol-1-yl-3-(4-bromophenyl)-2-phenylpropyl]phenyl}-difluoromethylphosphonic acid A solution of {4-[2-benzotriazol-1-yl-3-(4-bromophenyl)-2-phenylpropyl]phenyl}-difluoromethylphosphonic acid di-tert butyl ester (130 mg, 0.18 mmol) in 84% aqueous HOAc was stirred at r.t. for 6 h. Solvents was evaporated in vacuo. The residue was dissolved in EtOAc, extracted with 0.5M aqueous NaOH (2×). The alkaline extracts were combined, washed with EtOAc, than acidified with HOAc and extracted with EtOAc. The EtOAc extract was washed with $H_2$ and concentrated to give 60 mg (56%) of title compound as a white foam.

$^1$H NMR (Acetone-$d_6$) δ7.98 (d, 1H), 7.50–7.18 (m, 9H), 7.10 (d, 2H), 6.79 (d, 1H), 6.71 (d, 2H), 6.66 (d, 2H), 4.10 (m, 2H), 3.93 (m, 2H).

EXAMPLE 44

(4-{2-{4-[Difluoro(Phosphono)Methyl]Benzyl}-2-[4-(Methylsulfanyl)Phenyl]-3-Oxo-3-Phenylpropyl}Phenyl)(Difluoro)Methylphosphonic Acid Step 1:

To 2-[4-(methylsulfanyl)phenyl]-1-phenyl-1-ethanone (prepared like Example 47, Step 1 and 2) (0.10 g, 0.42 mmol) in THF (2 mL) at −78° C. was added 18 crown 6 (0.05g) and potassium tert-butoxide (0.92 mL, 0.92 mmol). Then the temperature was raised to 0° C. for 30 minutes. The reaction mixture was cooled back down to −78° C. Then di(tert-butyl)[4-(bromomethyl)phenyl](difluoro)methyl phosphonate (0.38 g, 0.92 mmol) was added directly to the reaction mixture. Then the temperature raised to room temperature for 2 h. The reaction was quenched with a solution of saturated ammonium acetate (10 mL) and extracted with ethyl acetate. The organic extract were dried over sodium sulfate. The compound was purified by flash chromatography and hydrolyzed using acetic acid/water 9:1 (10 mL) overnight. Evaporation to dryness and freeze dried.

$^1$H NMR (400 MHz) in ($CD_3COCD_3$) δ: 7.60 (2H, d), 7.45 (1H, t), 7.35 (6H, m), 7.20 (2H, d), 7.10 (2H, d), 6.90 (4H, d), 3.52 (4H, m), 2.45 (3H, s).

EXAMPLE 45

{4-[2-[4-(1,2-Difluoro-1-phosphonoethyl)Benzyl]-2,3-Bis(4-Fluorophenyl)-3-Oxopropyl]Phenyl} (Difluoro) Methylphosphonic Acid The title compound was prepared as described for Example 47, using 1-(4-fluorophenyl)-2-(4-fluorophenyl)-1-ethanone.

$^1$H NMR ($CD_3COCD_3$) δ: 7.80–6.80 (16H, m), 3.50 (4H, m).

EXAMPLE 46

[4-(2-4-[2-(Tert-Butoxy)-1,1-Difluoro-2-Oxoethoxy] Benzyl-3-Oxo-2,3-Diphenylpropyl)Phenyl] (Difluoro) Methylphosphonic Acid The title compound was prepared from tert-butyl 2-[4-(bromomethyl)phenoxy]-2,2-difluoroacetate (prepared according to H. Fretz, Tetrahedron 54, 4849, 1998) and deoxybenzoin by using the same procedure described in Example 31.

$^1$H NMR (400 MHz, methanol-$d_4$) δ9.95 (2H, bs), 7.60 (2H, d), 7.10–7.50 (10, m), 6.80–7.00 (6H, m), 3.45–3.65 (4H, m), 1.48 (9H, s).

What is claimed is:

1. A compound represented by formula I:

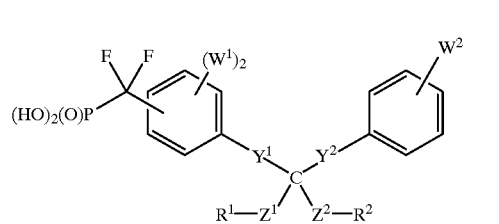

or a pharmaceutically acceptable salt thereof, wherein:

$R^1$ is selected from the group consisting of:
$C_{1-10}$alkyl$(R^a)_{0-7}$, $C_{2-10}$alkenyl$(R^a)_{0-7}$, $(R^a)_{0-7}$ and Het$(R^a)_{0-7}$;

$R^2$ is selected from the group consisting of $C_{1-6}$alkyl $(R^a)_{0-7}$, Aryl$(R^a)_{0-7}$ and Het$(R^a)_{0-7}$;

wherein, each $R^a$ independently represents a member selected from the group consisting of: Aryl, OH, halo, $CO_2H$, $CO_2C_{1-6}$alkyl, $OC_{1-10}$alkyl, $S(O)_yC_{1-6}$alkyl, $S(O)_yNR^3R^{4'}$, Het and —$P(O)(OH)_2$ wherein y is 0, 1, or 2;

$Y^1$ and $Y^2$ represent —$(CR^3R^4)_a$—X—$(CR^3R^4)_b$— wherein a and b are integers 0–1 such that the sum of a and b equals 0, 1 or 2, X represents a bond, O, $S(O)_y$, $NR^{3'}$, $C(O)$, $OC(O)$, $C(O)O$, $C(O)NR^{3'}$, $NR^{3'}C(O)$ or —CH═CH—, where y is as previously defined;

and $R^3$ and $R^4$ are independently H, halo, $C_{1-10}$-alkyl or halo$C_{1-10}$alkyl, or $R^3$ and $R^4$ taken together with any intervening atoms represent a 3–7 membered ring;

$R^{3'}$ is selected from the group consisting of: H, $C_{1-6}$alkyl, halo$C_{1-6}$alkyl, OH, $C(O)C_{1-6}$ alkyl, $C(O)$Aryl, $C(O)$Het, $C(O)C_{1-6}$ haloalkyl, Aryl and Het;

$R^{4'}$ is selected from the group consisting of: H, $C_{1-6}$alkyl, halo$C_{1-6}$alkyl, Aryl and Het;

$Z^1$ and $Z^2$ each independently represent —$(CR^3R^4)_a$—X—$(CR^3R^4)_b$— wherein X, a, b, $R^3$ and $R^4$ are as defined, or $Z^1$ and $Z^2$ are taken in conjunction with $R^1$ and $R^2$ and represent in combination

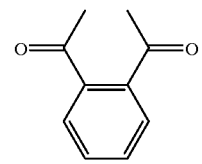

wherein $R^1$ and $R^2$ represent carbonyl groups, or $Z^1$ and $Z^2$ together are —$CH_2NR^1C(O)NR^2CH_2$—, with $R^1$ and $R^2$ as originally defined;

$W^1$ and $W^2$ are each independently selected from the group consisting of: H, OH, CN, halo, $OC_{1-6}$alkyl $(R^a)_{0-7}$, $S(O)_yC_{1-6}$alkyl$(R^a)_{0-7}$, with y equal to 0–2, $S(O)_3H$, CN, $C_{1-6}$alkyl$(R^a)_{0-7}$, $N_3$, $CO_2H$, $CO_2$ $C_{1-6}$alkyl$(R^a)_{0-7}$, $CO_2C_{2-6}$alkenyl$(R^a)_{0-7}$, $C(O)$ $C_{1-6}$alkyl$(R^a)_{0-7}$, $C(O)NR^{3'}R^{4'}$, $S(O)_yNR^{3'}R^{4'}$, $NR^{3'}R^{4'}$ and Het, wherein $R^{3'}$ and $R^{4'}$ are as defined above; or the two $W^1$ groups taken in combination represent a fused phenyl ring;

Aryl represents a 6–14 membered aromatic ring system;

and Het represents a 5–10 membered aromatic ring system containing 1–4 heteroatoms, 0–4 of which are N atoms and 0–1 of which are O or $S(O)_y$, wherein y is as previously defined, and 0–2 carbonyl groups.

2. A compound in accordance with claim 1 wherein $W^1$ and $W^2$ are independently selected from the group consisting of:
   (a) hydrogen,
   (b) halo,
   (c) $OC_{1-6}$alkyl$(R^a)_{0-7}$,
   (d) $SC_{1-6}$alkyl$(R^a)_{0-7}$,
   (e) $C_{1-6}$alkyl$(R^a)_{0-7}$,
   (f) $CO_2H$,
   (g) $CO_2$—$C_{1-6}$alkyl$(R^a)_{0-7}$,
   (h) OH,
   (l) $N(R^{3'})(R^{4'})$ and
   (m) $C(O)C_{1-6}$alkyl$(R^a)_{0-7}$.

3. A compound in accordance with claim 2 wherein each $W^1$ represents H, and $W^2$ represents $C_{1-6}$alkyl$(R^a)_{0-7}$.

4. A compound in accordance with claim 3 wherein $W^2$ represents —$CF_2$—$PO_3H_2$.

5. A compound in accordance with claim 1 wherein Het is selected from the group consisting of:

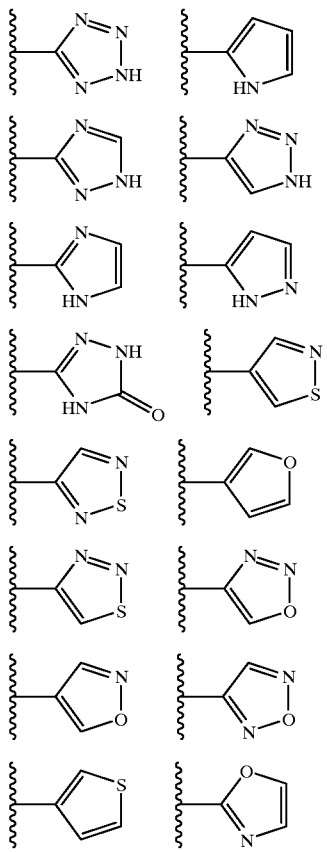

-continued

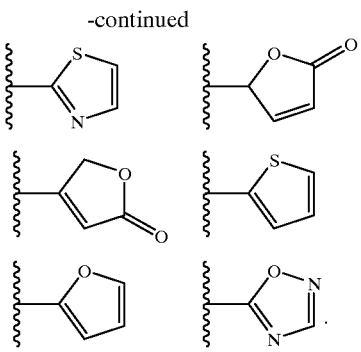

6. A compound in accordance with claim 1 wherein: $Y^1$ and $Y^2$ are each independently selected from the group consisting of:
   (a) —$CH_2$—,
   (b) —O—$CH_2$—,
   (c) —$CH_2$O—,
   (d) —$CH_2$O—$CH_2$—,
   (e) —S—$CH_2$—,
   (f) —$CH_2$—S—,
   (g) —$CH_2$—S—$CH_2$—,
   (h) —$S(O)_2$—$CH_2$—,
   (i) —$CH_2$—$S(O)_2$—,
   (j) —$CH_2$—$S(O)_2$—$CH_2$—,
   (k) —$S(O)_2$—,
   (l) —S—,
   (m) —O—, and
   (n) —$NR^{3'}$—.

7. A compound in accordance with claim 6 wherein $Y^1$ and $Y^2$ are selected from the group consisting of: (a) —$CH_2$—, (b) —O—$CH_2$—, (c) —$CH_2$—O—, (d) —$CH_2$—O—$CH_2$—, (e) —S—$CH_2$—, (f) —$CH_2$—S— and (g) —$CH_2$—S—$CH_2$—.

8. A compound in accordance with claim 1 wherein $Z^1$ and $Z^2$ are each independently selected from the group consisting of:
   (a) —C(O)—O—,
   (b) —C(O)—NH—,
   (c) —C(O)—
   (d) —$CH_2$—O—,
   (e) —$CH_2$—,
   (f) —$CH_2$—O—$CH_2$—
   (g) —$CH_2$—S—
   (h) —$CH_2$—S—$CH_2$—
   (i) —$S(O)_2$—,
   (j) —$CH_2$—$S(O)_2$—
   (k) —$CH_2$—$S(O)_2$—$CH_2$—
   (l) —S—,
   (m) —O—,
   (n) —NH—,
   (o) —O—C(O)—,
   (p) —NH—C(O)—,
   (q) —O—$CH_2$—,
   (r) —S—$CH_2$—,
   (s) —$S(O)_2$—$CH_2$— and
   (t) a direct bond.

9. A compound in accordance with claim 8 wherein $Z^1$ and $Z^2$ are each independently selected from the group consisting of: (a) —C(O)—O—, (c) —C(O)—, (d) —CH$_2$—O—, (e) —CH$_2$—, (f) —CH$_2$—O—CH$_2$— (g) —CH$_2$—S— (h) —CH$_2$—S—CH$_2$— (m) —O—, (o) —O—C(O)—, and (t) a direct bond.

10. A compound in accordance with claim 1 wherein R$^1$ and R$^2$ are each independently selected from the group consisting of:
(a) C$_1$–C$_{10}$alkyl,
(b) C$_1$–C$_{10}$fluoroalkyl,
(c) unsubstituted, mono-, di- or tri-substituted phenyl wherein the substituents are selected from the group consisting of:
 (1) halo,
 (2) C$_{1-10}$alkoxy,
 (3) C$_{1-6}$alkylthio,
 (4) CF$_3$,
 (5) C$_{1-6}$alkyl,
 (6) —CO$_2$H and
 (7) —CO$_2$—C$_{1-4}$alkyl,
(d) unsubstitued, mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2 or 3 additional N atoms; wherein said substituents are selected from the group consisting of:
 (1) halo,
 (2) C$_{1-6}$alkoxy,
 (3) C$_{1-6}$alkylthio,
 (4) CF$_3$,
 (5) C$_{1-6}$alkyl,
 (6) —CO$_2$H, and
 (7) —CO$_2$—C$_{1-4}$alkyl,
(e) benzoheteroaryl which includes the benzo fused analogs of (d).

11. A compound in accordance with claim 1 wherein:
W$^1$ and W$^2$ are independently selected from the group consisting of:
(a) hydrogen,
(b) halo,
(c) OC$_{1-6}$alkyl(R$^a$)$_{0-7}$,
(d) SC$_{1-6}$alkyl(R$^a$)$_{0-7}$,
(e) C$_{1-6}$alkyl(R$^a$)$_{0-7}$,
(f) CO$_2$H,
(g) CO$_2$—C$_{1-6}$alkyl(R$^a$)$_{0-7}$,
(h) OH,
(l) N(R$^{3'}$)(R$^{4'}$) and
(m) C(O)C$_{1-6}$alkyl(R$^a$)$_{0-7}$;
Y$^1$ and Y$^2$ are each independently selected from the group consisting of:
(a) —CH$_2$—,
(b) —O—CH$_2$—,
(c) —CH$_2$—O—,
(d) —CH$_2$—O—CH$_2$—,
(e) —S—CH$_2$—,
(f) —CH$_2$—S—,
(g) —CH$_2$—S—CH$_2$—,
(h) —S(O)$_2$—CH$_2$—,
(i) —CH$_2$—S(O)$_2$—,
(j) —CH$_2$—S(O)$_2$—CH$_2$—,
(k) —S(O)$_2$—,
(l) —S—,
(m) —O—, and
(n) —NR$_3$—;
Z$^1$ and Z$^2$ are each independently selected from the group consisting of:

(a) —C(O)—O—,
(b) —C(O)—NH—,
(c) —C(O)—
(d) —CH$_2$—O—,
(e) —CH$_2$—,
(f) —CH$_2$—O—CH$_2$—
(g) —CH$_2$—S—
(h) —CH$_2$—S—CH$_2$—
(i) —S(O)$_2$—,
(j) —CH$_2$—S(O)$_2$—
(k) —CH$_2$—S(O)$_2$—CH$_2$—
(l) —S—,
(m) —O—,
(n) —NH—,
(o) —O—C(O)—,
(p) —NH—C(O)—,
(q) —O—CH$_2$—,
(r) —S—CH$_2$—,
(s) —S(O)$_2$—CH$_2$— and
(t) a direct bond;
R$^1$ and R$^2$ are each independently selected from the group consisting of:
(a) C$_1$–C$_{10}$alkyl,
(b) C$_1$–C$_{10}$fluoroalkyl,
(c) unsubstituted, mono-, di- or tri-substituted phenyl wherein the substituents are selected from the group consisting of:
 (1) halo,
 (2) C$_{1-10}$alkoxy,
 (3) C$_{1-6}$alkylthio,
 (4) CF$_3$,
 (5) C$_{1-6}$alkyl,
 (6) —CO$_2$H and
 (7) —CO$_2$—C$_{1-4}$alkyl,
(d) unsubstitued, mono-, di- or tri-substituted heteroaryl wherein the heteroaryl is a monocyclic aromatic ring of 5 atoms, said ring having one hetero atom which is S, O, or N, and optionally 1, 2, or 3 additional N atoms; or the heteroaryl is a monocyclic ring of 6 atoms, said ring having one hetero atom which is N, and optionally 1, 2 or 3 additional N atoms; said substituents are selected from the group consisting of:
 (1) halo,
 (2) C$_{1-6}$alkoxy,
 (3) C$_{1-6}$alkylthio,
 (4) CF$_3$,
 (5) C$_{1-6}$alkyl,
 (6) —CO$_2$H, and
 (7) —CO$_2$—C$_{1-4}$alkyl,
(e) benzoheteroaryl which includes the benzo fused analogs of (d).

12. A compound in accordance with claim 11 wherein Het is selected from the group consisting of:

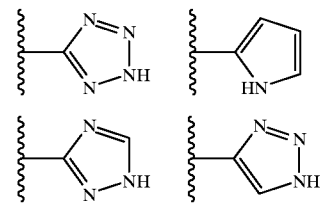

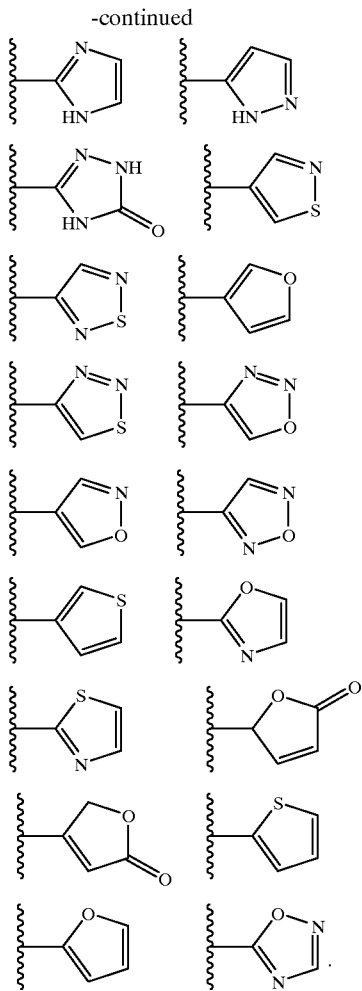

13. A compound selected from the group consisting of:
2,2-di{4-[difluoro(phosphono)methyl]benzyl}malonic acid, benzyl methyl ester;
2,2-di{4-[difluoro(phosphono)methyl]benzyl}malonic acid, dibenzyl ester;
2,2-di{4-[difluoro(phosphono)methyl]benzyl}malonic acid, diisopropyl ester;
2,2-di {4-[difluoro(phosphono)methyl]benzyl}-3-methoxy-3-oxopropanoic acid;
3-(benzylamino)-2,2-di{4-[difluoro(phosphono)methyl] benzyl}-3-oxopropanoic acid, methyl ester;
2,2-di{4-[difluoro(phosphono)methyl]benzyl}malonic acid;
2-{4-[3-(benzyloxy)-2-{4-[difluoro(phosphono)methyl] benzyl}-2-(methoxycarbonyl)-3-oxopropyl]phenyl}-2,2-difluoroacetic acid;
2-{4-[difluoro(phosphono)methyl]benzyl}-2-[4-(phosphonomethyl)benzyl]malonic acid, dibenzyl ester;
2-(4-carboxybenzyl)-2-{4-[difluoro(phosphono)methyl] benzyl}malonic acid, dibenzyl ester;
2-Benzyl-2-{4-[difluoro(phosphono)methyl] benzyl}malonic acid, dibenzyl ester;
2,2-di{4-[difluoro(phosphono)methyl]benzyl}-1,3-propane-diol, dibenzyl ether;
2,2-di{4-[difluoro(phosphono)methyl]benzyl}-1,3-propane-diol;
2-{4-[difluorophosphono)methyl]benzyl}-2-[4-(methylsulfonyl)benzyl]malonic acid, dibenzyl ester;
2-{4-[difluoro(phosphono)methyl]benzyl}-2-{4-[(methylsulfonyl)methyl]benzyl}malonic acid, dibenzyl ester, and
2-{4-[difluoro(phosphono)methyl]benzyl}-2-{4-[(ethylsulfonyl)methyl]benzyl}malonic acid, dibenzyl ester;
2-[4-(3-(benzyloxy)-2-[(benzyloxy)carbonyl]-2-{4-[difluoro(phosphono)methyl]benzyl}-3-oxopropyl) phenyl]-2,2-difluoroacetic acid;
(4-(2-[4-(aminocarbonyl)benzyl]-3-(benzyloxy)-2-[(benzyloxycarbonyl]-3-oxopropy}phenyl)(difluoro) methylphosphonic acid;
{4-[2-{4-[difluoro(phosphono)methyl]benzyl}-3-isopropoxy-2-(isopropoxymethyl)propyl]phenyl} (difluoro)methyl phosphonic acid;
(4-{3-(benzyloxy)-2-[((benzyloxy)carbonyl]-3-oxo-2-[4-(trifluoromethyl) benzyl]propyl}phenyl)(difluoro) methylphosphonic acid;
(4-{3-(benzyloxy)-2-[(benzyloxy)carbonyl]-3-oxo-2-[4-(trifluoromethoxy) benzyl]propyl}phenyl)(difluoro) methylphosphonic acid;
(4-2-benzyl-3-(benzyloxy)-2-[(benzyloxy)methyl] propylphenyl)(difluoro)methylphosphonic acid;
(4-(3-(benzyloxy)-2-[(benzyloxy)carbonyl]-2-{4-[(dimethylamino)sulfonyl)benzyl]-3-oxopropyl)phenyl] (difluoro)methylphosphonic acid;
(4-{2-{4-[(acetylamino)sulfonyl]benzyl}-3-(benzyloxy)-2-[(benzyloxy)carbonyl]-3-oxopropyl}phenyl)difluoro) methylphosphonic acid;
(4-{3-(benzyloxy)-2-[(benzyloxy)carbonyl]-2-[(1,3-dioxo-1,3-dihydro-2H-isoindol-2-yl)methyl]-3-oxopropyl}phenyl)(difluoro)methylphosphonic acid;
(4-{3-(benzyloxy)-2-[(benzyloxy)carbonyl]-3-oxo-2-[4-(1,2,3-thiadiazol-4-yl)benzyl]propyl}phenyl)(difluoro) methylphosphonic acid;
{4-[(2-{4-[difluoro(phosphono)methyl]benzyl}-1,3-dioxo-2,3-dihydro-1H-inden-2-yl)methyl]phenyl}(difluoro) methylphosphonic acid;
2-[4-(3-(Benzyloxy)-2-[(benzyloxy)methyl]-2-4-[difluoro (phosphono)methyl]benzylpropyl)phenyl]-2,2-difluoroacetic acid;
(4-(2-[4-(aminosulfonyl)benzyl]-3-(benzyloxy)-2-[(benzyloxy)methyl]propyl)phenyl)(difluoro) methylphosphonic acid;
[4-(2-{4-[difluoro(phosphono)methyl]benzyl}-3-oxo-2,3-diphenylpropyl)phenyl](difluoro)methylphosphonic acid;
di{4-[difluoro(phosphono)methyl]benzyl}-bis(2-benzothiazolyl)methane difluoro[4-(3-oxo-2,3-diphenylpropyl)phenyl]methylphosphonic acid;
2-[4-(2-4-[Difluoro(phosphono)methyl]benzyl-3-oxo-2,3-diphenylpropyl)phenoxy]-2,2-difluoroacetic acid;
(4-{2-{4-[difluoro(phosphono)methyl]benzyl}-3-(3-fluorophenyl)-2-[4-(methylsulfanyl)phenyl]-3-oxopropyl}phenyl)(difluoro)methyl phosphonic acid;
(4-{2-{4-[difluoro(phosphono)methyl]benzyl}-3-(3-fluoro-4-methoxyphenyl)-2-[4-(methylsulfonyl)phenyl]-3-oxopropyl}phenyl)(difluoro)methylphosphonic acid;
(4-{2-[4-(aminosulfonyl)benzyl]-3-oxo-2,3-diphenylpropyl}phenyl) (difluoro)methylphosphonic acid;

(4-{2-{4-[difluoro(phosphono)methyl]benzyl}-3-[4-(methylsulfanyl)phenyl]-3-oxo-2-phenylpropyl}phenyl)(difluoro)methylphosphonic acid;

[4-(2-benzyl-3-oxo-2,3-diphenylpropyl)phenyl](difluoro)methylphosphonic acid;

(4-{2-Benzotriazol-1-yl-3-[4-(difluorophosphonomethyl)phenyl]-2-phenyl-propyl}phenyl)-difluoromethylphosphonic acid;

2-(4-(2-{4-[Difluoro(phosphono)methyl]benzyl)-3-oxo-2,3-diphenylpropyl)phenyl}-2,2-difluoroacetic acid;

4-(2-{4-[Difluoro(phosphono)methyl]benzyl}-3- oxo-2,3diphenylpropyl)benzoic acid;

(4-{2-{4-[difluoro(phosphono)methyl]benzyl}-3-(4-fluorophenyl)-2-[4-(methylsulfanyl)phenyl]-3-oxopropyl}phenyl)(difluoro)methylphosphonic acid;

(4-{2-Benzotriazol-1-yl-2-(3,4-difluorophenyl)-3-[4-(difluorophosphonomethyl)phenyl]propyl}phenyl)difluoromethylphosphonic acid;

{4-[2-Benzotriazol-1-yl-3-(4-bromophenyl)-2-phenylpropyl]phenyl}-difluoromethylphosphonic acid;

(4-{2-{4-[difluoro(phosphono)methyl]benzyl}-2-[4-(methylsulfanyl)phenyl]-3-oxo-3-phenylpropyl}phenyl)(difluoro)methylphosphonic acid;

{4-[2-[4-(1,2-difluoro-1-phosphonoethyl)benzyl]-2,3-bis(4-fluorophenyl)-3-oxopropyl]phenyl}(difluoro)methylphosphonic acid;

[4-(2-4-[2-(tert-butoxy)-1,1-difluoro-2-oxoethoxy]benzyl-3-oxo-2,3-diphenylpropyl)phenyl](difluoro)methylphosphonic acid.

14. A compound in accordance with Table 1 or Table 2:

TABLE 1

| | Example | Method |
|---|---|---|
| 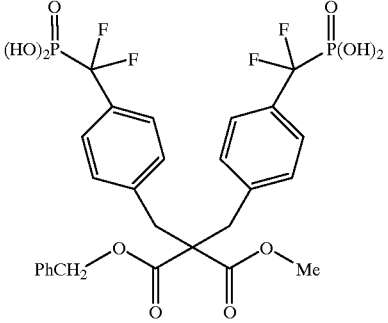 | 1 | A |
| 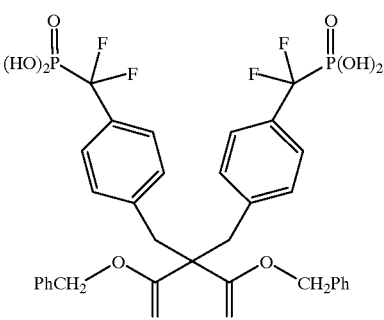 | 2 | A |
| 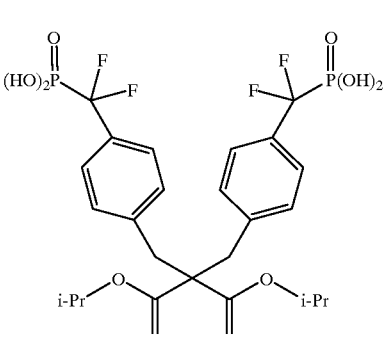 | 3 | A |

TABLE 1-continued

| | Example | Method |
|---|---|---|
| (structure) | 4 | B |
| (structure) | 5 | B |
| (structure) | 6 | C |
| (structure) | 7 | D |

TABLE 1-continued

| Structure | Example | Method |
|---|---|---|
| (HO)₂P(O)CF₂–[C₆H₄]–CH₂–C(CO₂CH₂Ph)₂–CH₂–[C₆H₄]–CH₂P(O)(OH)₂ | 8 | D |
| (HO)₂P(O)CF₂–[C₆H₄]–CH₂–C(CO₂CH₂Ph)₂–CH₂–[C₆H₄]–CO₂H | 9 | D |
| (HO)₂P(O)CF₂–[C₆H₄]–CH₂–C(CO₂CH₂Ph)₂–CH₂–[C₆H₅] | 10 | D |
| (HO)₂P(O)CF₂–[C₆H₄]–CH₂–C(CH₂OCH₂Ph)₂–CH₂–[C₆H₄]–CF₂P(O)(OH)₂ | 11 | E |

TABLE 1-continued

| Structure | Example | Method |
|---|---|---|
| [Bis(difluoromethylenephosphonic acid) compound with bis(hydroxymethyl) linker on two para-benzyl groups] | 12 | E |
| [(Difluoromethylenephosphonic acid)-benzyl / (4-methylsulfonyl)benzyl malonate dibenzyl ester] | 13 | D |
| [(Difluoromethylenephosphonic acid)-benzyl / (4-methylsulfonylmethyl)benzyl malonate dibenzyl ester] | 14 | D |
| [(Difluoromethylenephosphonic acid)-benzyl / (4-ethylsulfonylmethyl)benzyl malonate dibenzyl ester] | 15 | D |

TABLE 1-continued
| | Example | Method |
|---|---|---|
| 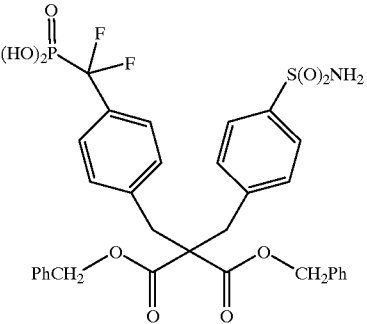 | 16 | D |
| 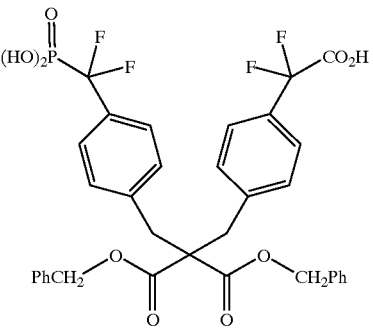 | 17 | D |
| 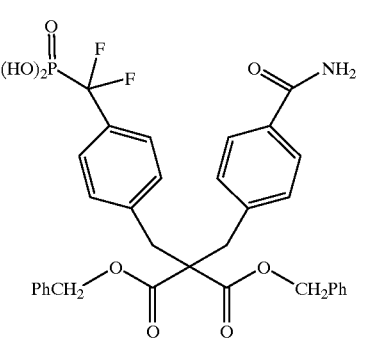 | 18 | D |
| 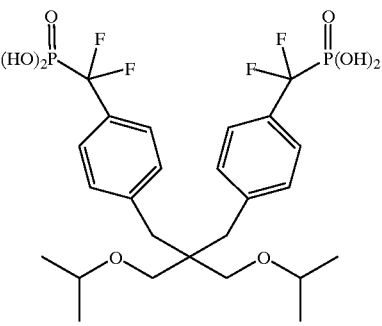 | 19 | E |

TABLE 1-continued
| | Example | Method |
|---|---|---|
| 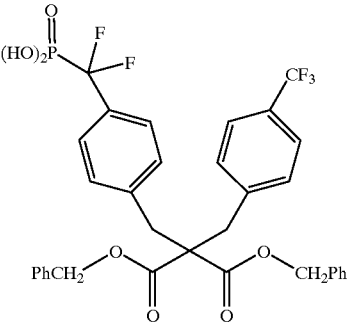 | 20 | D |
| 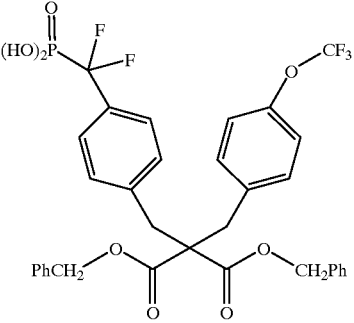 | 21 | D |
| 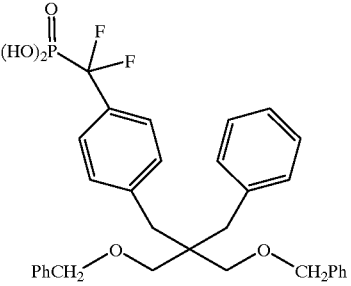 | 22 | D & E |
| 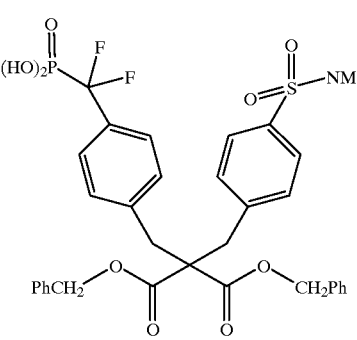 | 23 | D |

TABLE 1-continued
| | Example | Method |
|---|---|---|
| 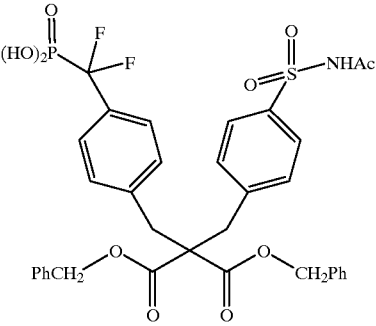 | 24 | D |
| 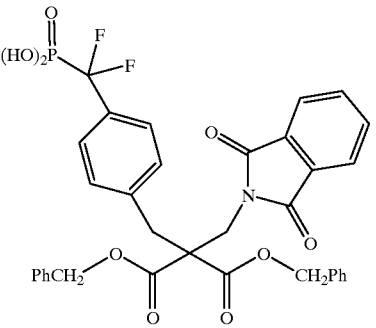 | 25 | D |
| 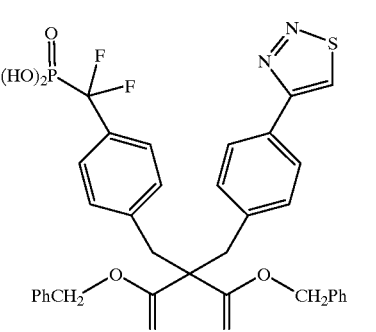 | 26 | D |
| 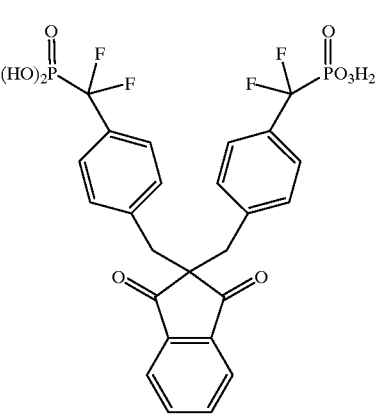 | 27 | F |

TABLE 1-continued

| Example | Method |
|---|---|
| 28 | J |
| 29 | |
| 30 | F |
| 31 | K |

TABLE 1-continued

| | Example | Method |
|---|---|---|
| (structure) | 32 | F |
| (structure) | 33 | F |
| (structure) | 34 | F |
| (structure) | 35 | F |

TABLE 1-continued
| | Example | Method |
|---|---|---|
| | 36 | F |
| | 37 | F |
| | 38 | L |
TABLE 2
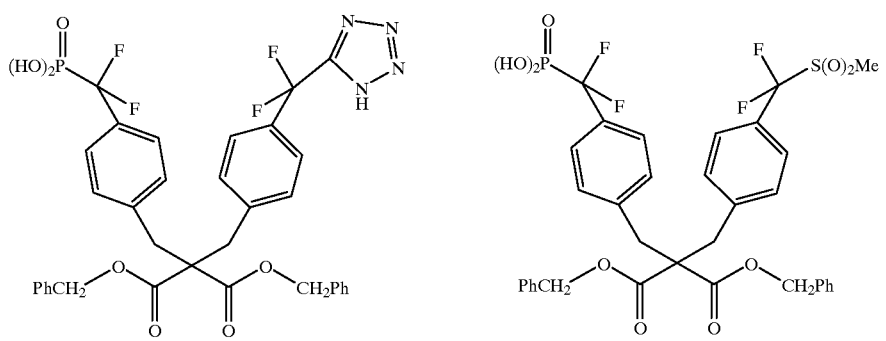

TABLE 2-continued
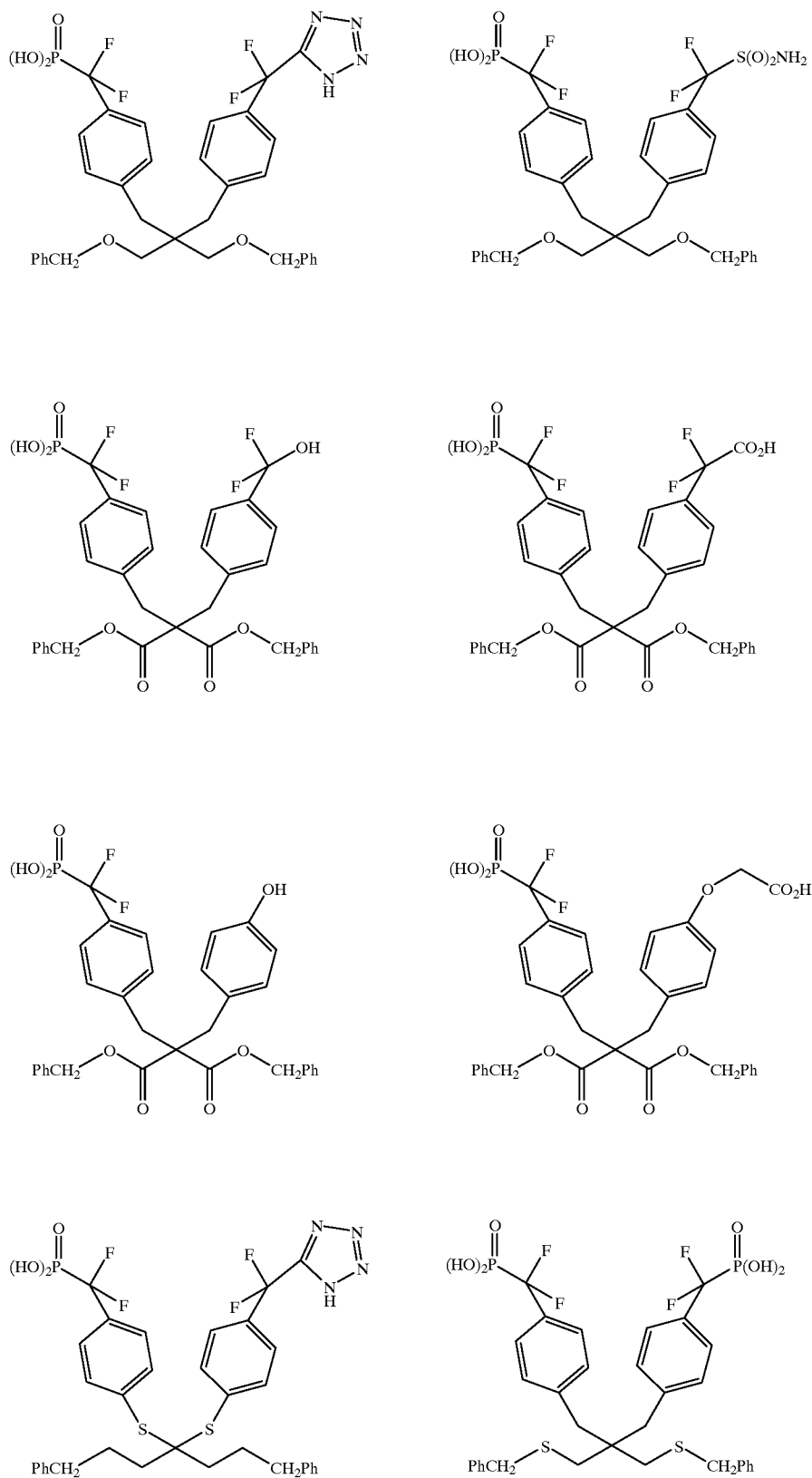

TABLE 2-continued
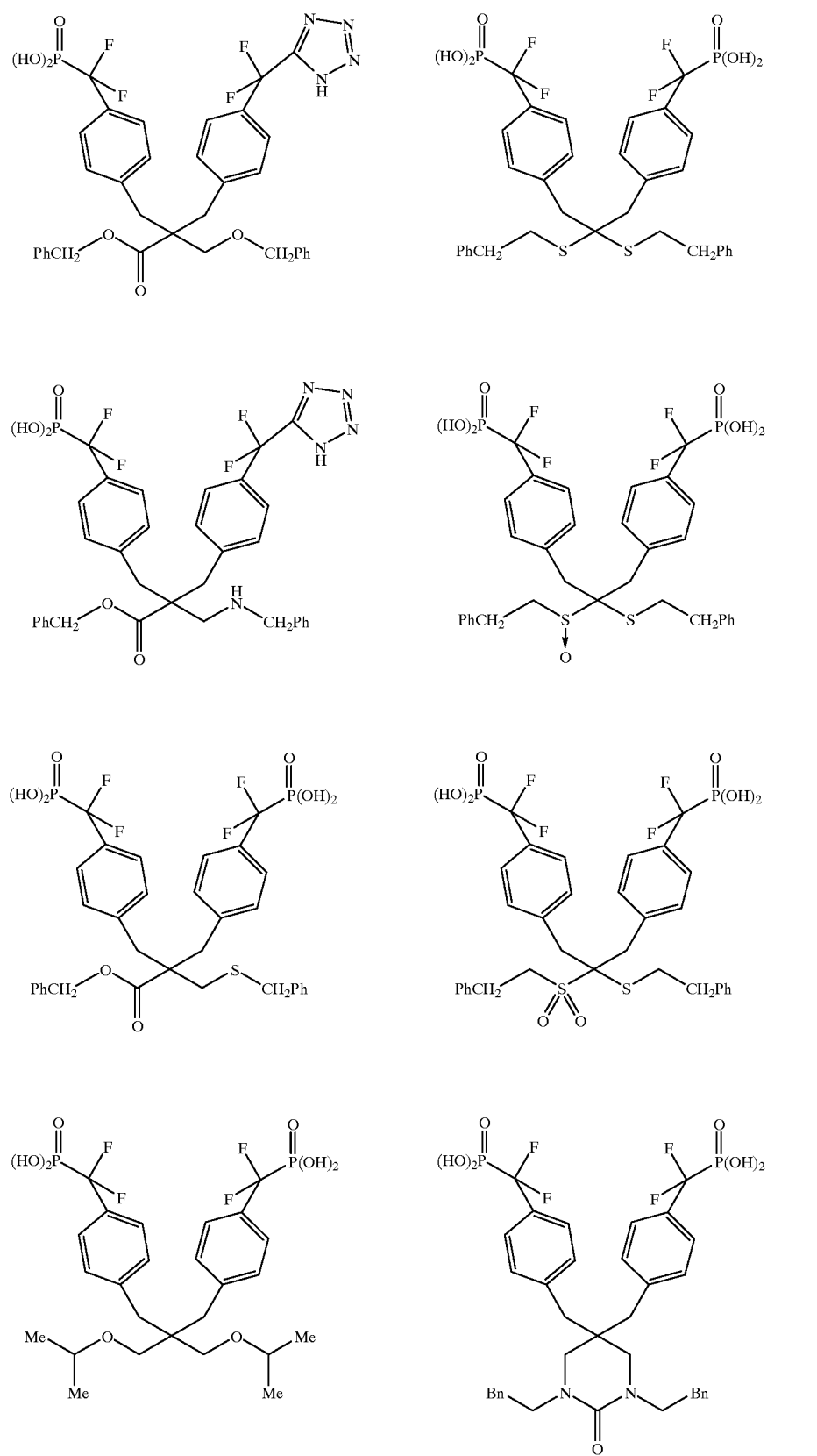

TABLE 2-continued
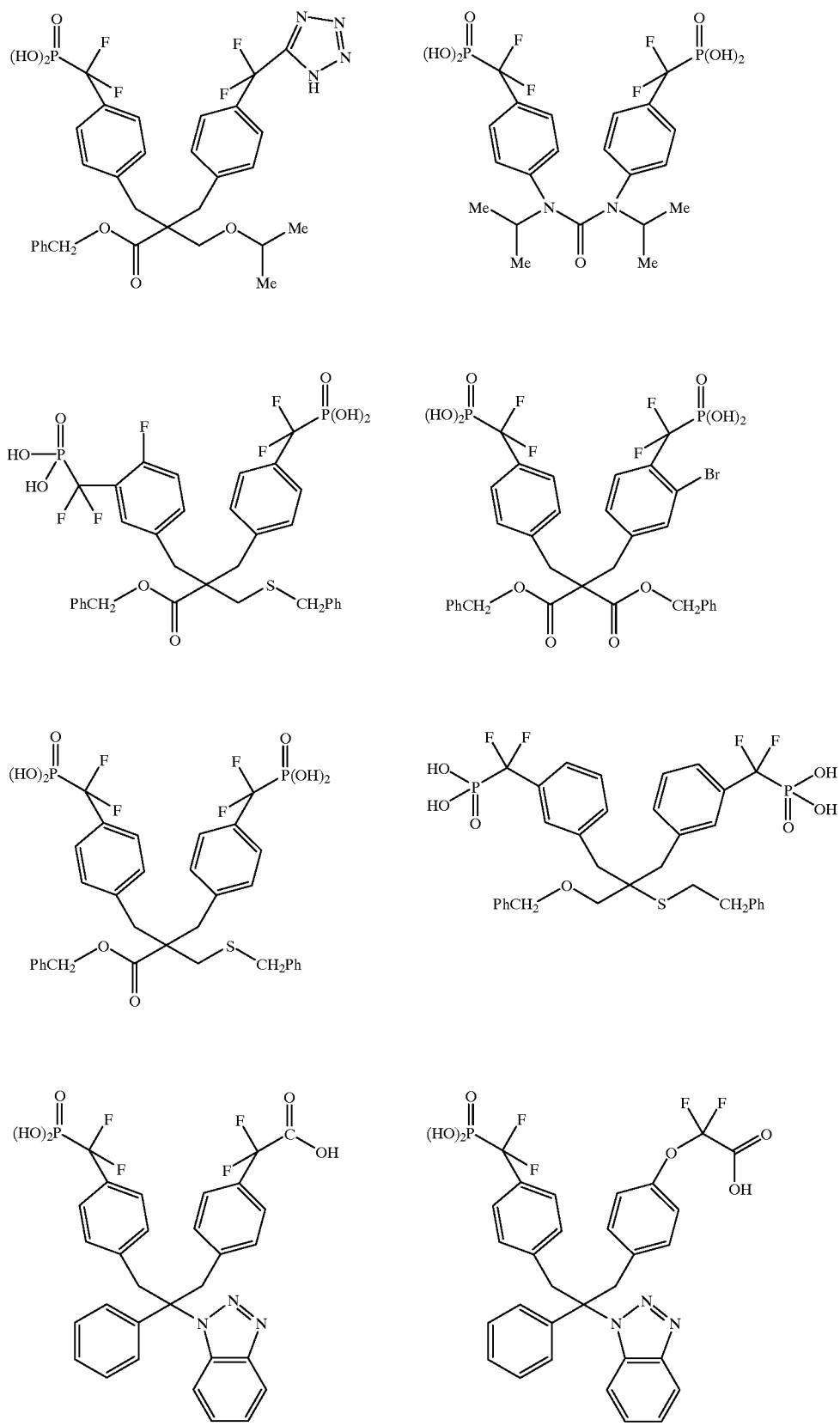

TABLE 2-continued
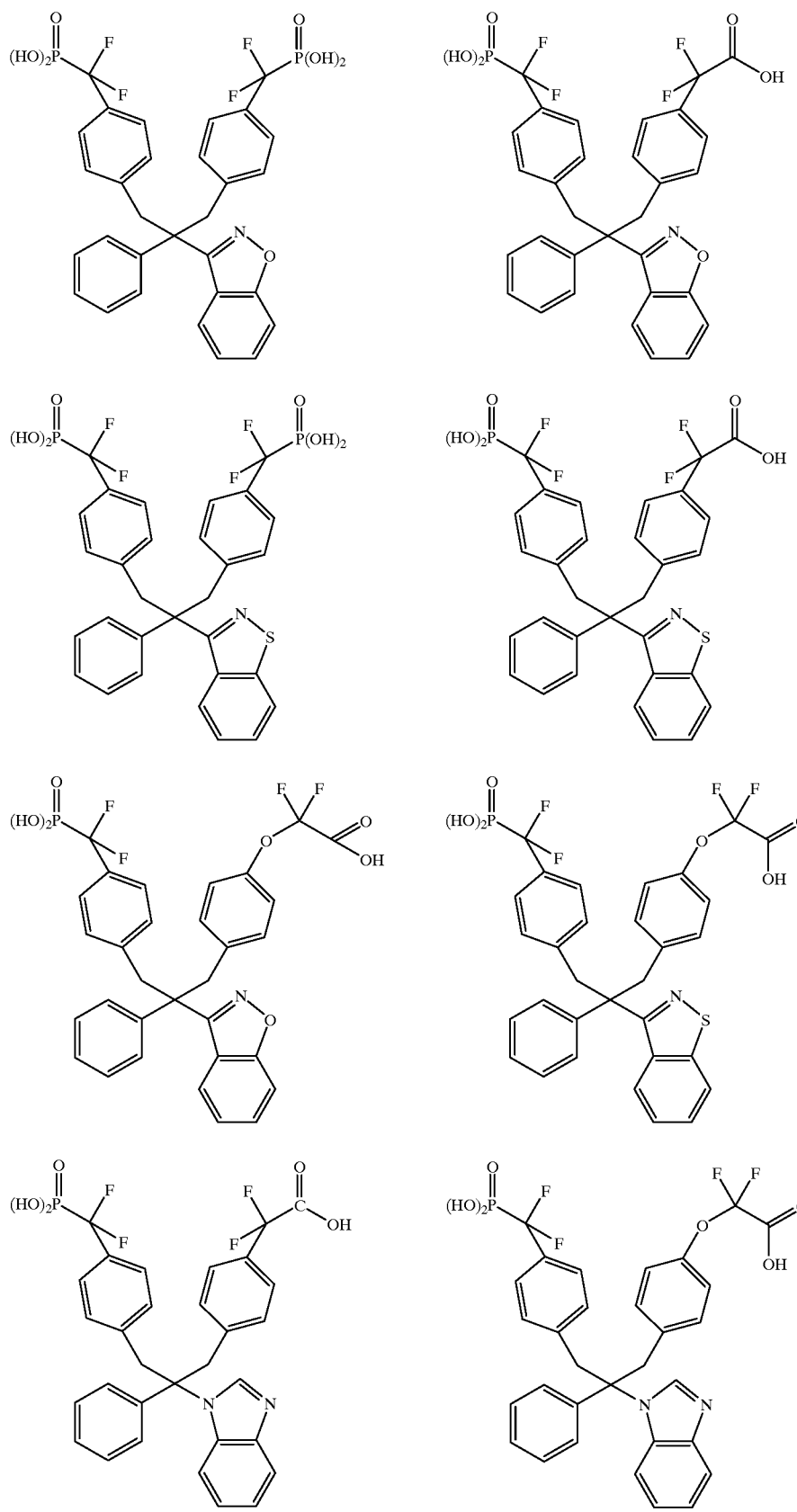

TABLE 2-continued
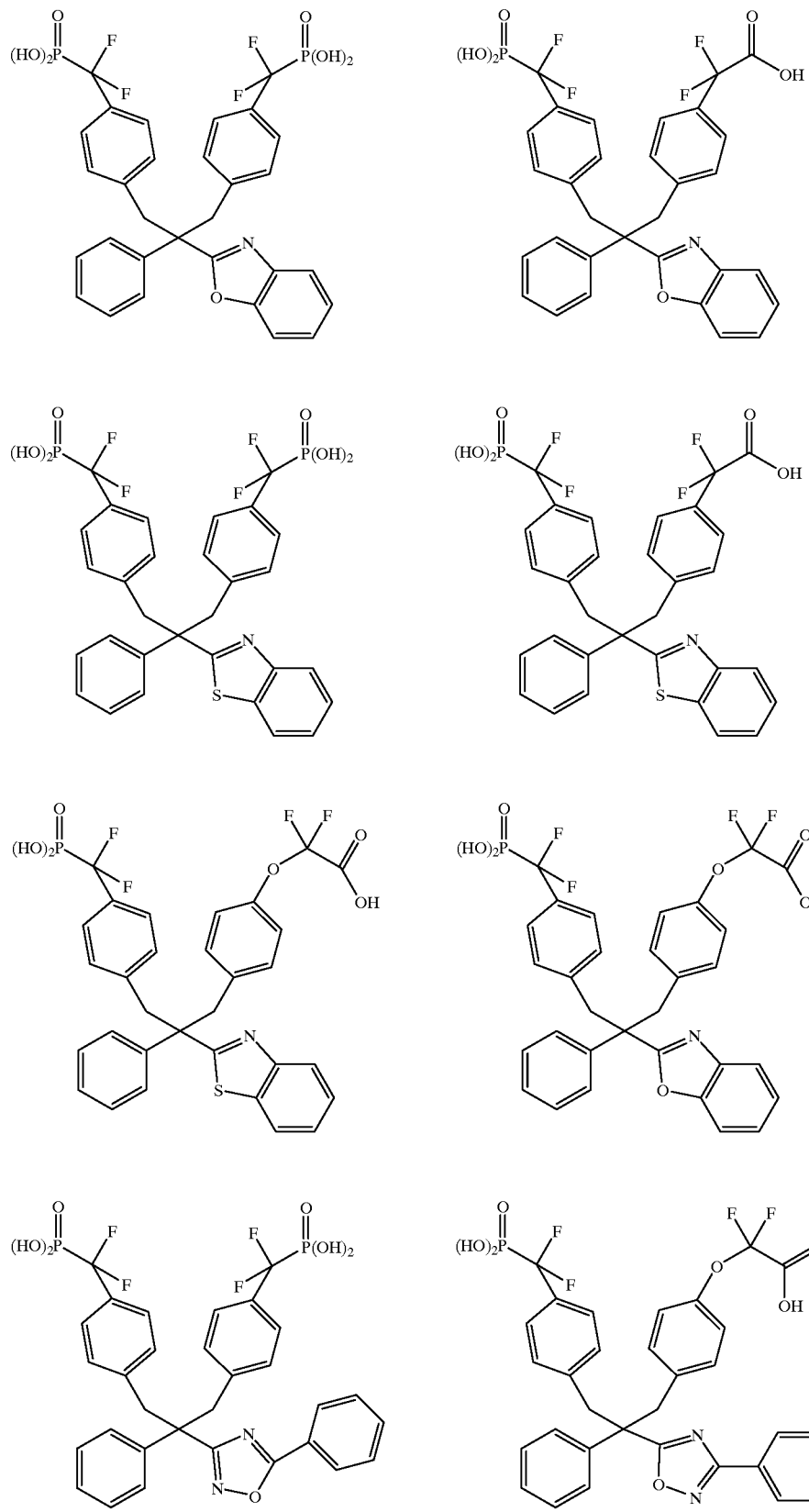

TABLE 2-continued

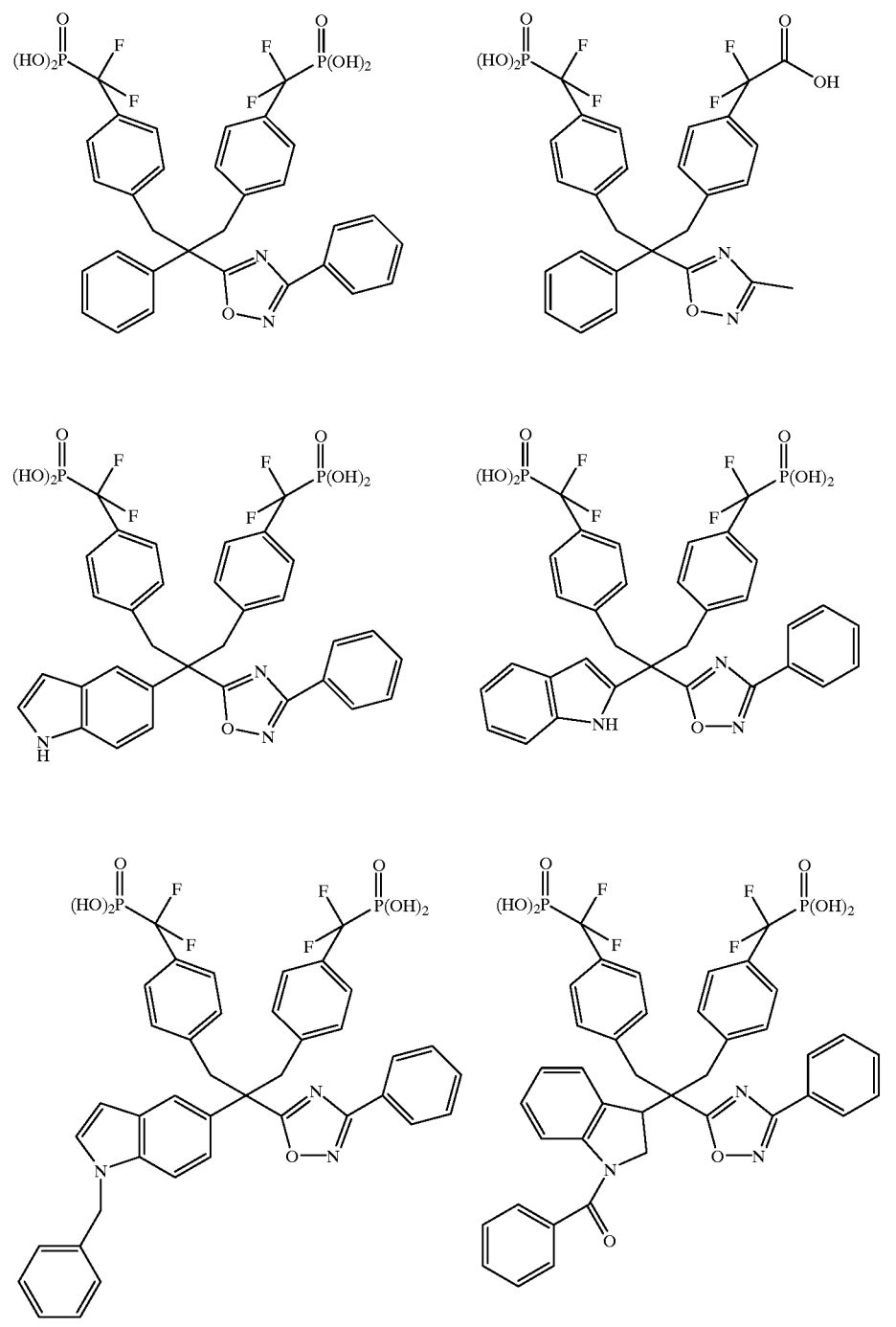

15. A pharmaceutical composition which is comprised of a compound in accordance with claim 1 in combination with a pharmaceutically acceptable carrier.

16. A pharmaceutical composition in accordance with claim 15 further comprised of a second anti-diabetic or anti-obesity effective compound.

17. A method of treating or preventing diabetes in a mammalian patient in need of such treatment comprising administering to said patient an anti-diabetic effective amount of a compound in accordance with claim 1.

18. A method of treating or preventing obesity in a mammalian patient in need of such treatment comprising administering to said patient an effective amount of a compound in accordance with claim 1.

19. A method in accordance with claim 17 further comprising administering to said patient a second anti-diabetic compound in an amount effective to treat or prevent diabetes.

20. A method in accordance with claim 18 further comprising administering to said patient a second anti-obesity compound in an amount effective to treat or prevent obesity.

21. A pharmaceutical composition in accordance with claim 15 further comprising an HMG-CoA reductase inhibitor.

22. A method in accordance with claim 17, further comprising administering to said patient an effective amount of an HMG-CoA reductase inhibitor.

23. A method for treating or preventing atherosclerosis in a mammalian patient in need of such treatment comprising administering to said patient an effective amount of a compound of claim 1 and an effective amount of an HMG-CoA reductase inhibitor.

* * * * *